(12) United States Patent
Rising et al.

(10) Patent No.: US 11,524,984 B2
(45) Date of Patent: Dec. 13, 2022

(54) ENGINEERED SPIDER SILK PROTEINS AND USES THEREOF

(71) Applicant: SPIBER TECHNOLOGIES AB, Stockholm (SE)

(72) Inventors: Anna Rising, Uppsala (SE); Jan Johansson, Stockholm (SE); Marlene Andersson, Uppsala (SE)

(73) Assignee: SPIBER TECHNOLOGIES AB, Stockholm (SE)

( * ) Notice: Subject to any disclaimer, the term of this patent is extended or adjusted under 35 U.S.C. 154(b) by 164 days.

(21) Appl. No.: 16/314,501

(22) PCT Filed: Jun. 29, 2017

(86) PCT No.: PCT/EP2017/066119
§ 371 (c)(1),
(2) Date: Dec. 31, 2018

(87) PCT Pub. No.: WO2018/002216
PCT Pub. Date: Jan. 4, 2018

(65) Prior Publication Data
US 2019/0248847 A1    Aug. 15, 2019

(30) Foreign Application Priority Data

Jul. 1, 2016   (EP) .................................... 16177521

(51) Int. Cl.
*C07K 14/435*      (2006.01)
*B33Y 70/00*       (2020.01)
*C12N 5/00*        (2006.01)
*A61K 38/00*       (2006.01)

(52) U.S. Cl.
CPC ........ *C07K 14/43518* (2013.01); *B33Y 70/00* (2014.12); *C12N 5/0018* (2013.01); *C12N 5/0062* (2013.01); *C12N 2513/00* (2013.01); *C12N 2533/50* (2013.01)

(58) Field of Classification Search
CPC ........................... C07K 14/43518; D01F 4/02
See application file for complete search history.

(56) References Cited

U.S. PATENT DOCUMENTS

| | | | | |
|---|---|---|---|---|
| 10,662,230 B2 * | 5/2020 | Hedhammar | ........ | C12N 5/0068 |
| 2007/0260039 A1 * | 11/2007 | Karatzas | .......... | C07K 14/43518 530/324 |
| 2014/0287433 A1 * | 9/2014 | Weingart | ........... | G01N 33/5432 435/7.4 |
| 2015/0119554 A1 * | 4/2015 | Hedhammar | .......... | C07K 14/78 530/353 |
| 2018/0282380 A1 * | 10/2018 | Kittleson | ............. | C07K 14/395 |

FOREIGN PATENT DOCUMENTS

| | | | |
|---|---|---|---|
| EP | 2644619 | 10/2013 | |
| JP | 2013/96037 A | 5/2013 | |
| WO | WO 03/057720 A2 | 7/2003 | |
| WO | WO 03/057727 A1 | 7/2003 | |
| WO | WO2007/078239 | 7/2007 | |
| WO | WO 2010/123450 | 10/2010 | |
| WO | WO 2012/055854 A1 | 5/2012 | |
| WO | WO 2013/164404 A1 | 11/2013 | |
| WO | WO 2015/036619 A1 | 3/2015 | |
| WO | WO 2015/042164 | 3/2015 | |
| WO | WO-2015042164 A2 * | 3/2015 | ............. C12P 21/00 |
| WO | WO 2017/081239 A1 | 5/2017 | |

OTHER PUBLICATIONS

Garb et al. (2005) Modular evolution of egg case silk genes across orb-weaving spider superfamilies, Proc. Natl. Acad. Sci. USA., vol. 102, pp. 11379-11384.*
Garb et al. (2010) Untangling spider silk evolution with spidroin terminal domains, BMC Evol. Biol., vol. 10, pp. 243-243.*
Eisoldt et al. (2011) Decoding the secrets of spider silk, Materialstoday, vol. 4, No. 3, pp. 80-86.*
Adrianos et al, "Nephila clavipes Flagelliform silk-like GGX motifs contribute to extensibility and spacer motifs contribute to strength in synthetic spider silk fibers," Biomacromolecules, 2013, 14:1751-1760.
Albertson et al, "Effects of different post-spin stretching conditions on the mechanical properties of synthetic spider silk fibers," J. Mech. Behav. Biomed. Mater., 2014, 29:225-234, (2014).
Copeland et al, "Development of a Process for the Spinning of Synthetic Spider Silk," ACS Biomaterials Science and Engineering, 2015, 1:577-584.
Heidebrecht et al, "Biomimetic fibers made of recombinant spidroins with the same toughness as natural spider silk," Adv Mater, 2015, 27:2189-2194.

(Continued)

*Primary Examiner* — Manjunath N Rao
*Assistant Examiner* — Samuel W Liu
(74) *Attorney, Agent, or Firm* — Birch, Stewart, Kolasch & Birch, LLP

(57) ABSTRACT

A recombinant spider silk protein, consisting of no more than 800 amino acids, comprising a set of domains arranged according to the formula (NT)-REP-CT, wherein: the optional NT-domain, if present, comprises a sequence of 100 to 160 amino-acid residues derived from the N-terminal domain of a spider silk protein; the REP-domain comprises a sequence of 30 to 600 amino acid residues derived from the repetitive segment of a spider silk protein; and the CT-domain comprises a sequence of 70 to 120 amino acid residues derived from the C-terminal domain of a spider silk protein selected from: a sequence of 72 to 110 amino acid residues derived from the C-terminal domain of a spider silk protein, wherein the sequence comprises at least 7 residues independently selected from K, R, E and D; a sequence having at least 85% identity to SEQ ID NO: 15 or any one of SEQ ID NOs: 62-65 or 67-73; and a sequence having at least 70% identity to SEQ ID NOs: 64 or any one of SEQ ID NOs: 62-65 or 67-73, wherein the sequence comprises at least 7 residues independently selected from K, R, E and D.

21 Claims, 21 Drawing Sheets
Specification includes a Sequence Listing.

(56) References Cited

OTHER PUBLICATIONS

PCT International Search Report and Written Opinion in International Appln. No. PCT/EP2017/066119, dated Sep. 10, 2017, 10 pages.
Plaza et al, "Relationship between microstructure and mechanical properties in spider silk fibers: identification of two regimes in the microstructural changes," Soft Matter, 2012, 8:6015-6026.
Rising et al, "N-Terminal Nonrepetitive Domain Common to Dragline, Flagelliform, and Cylindriform Spider Silk Proteins," Biomacromolecules, 2006, 7:3120-3124.
Rising et al, "Spider silk proteins: recent advances in recombinant production, structure-function relationships and biomedical applications," Cell. Mol. Life Sci., 2011, 68:169-184.
Shen & Murphy, "Solvent effects on self-assembly of beta-amyloid peptide," Biophys J. Aug. 1995, 69(2):640-51.
Teulé et al., "Modifications of spider silk sequences in an attempt to control the mechanical properties of the synthetic fibers," J Mater Sci., 2007, 42:8974-8985.
Anderson, M., et al, "Carbonic Anhydrase Generates CO2 and H+ That Drive Spider Silk Formation Via Opposite Effects on the Terminal Domains," PLOS Biology, Aug. 2014, vol. 12, issue 8, pp. 1-14.
Gao, Z., et al. "Structural Characterization of Minor Ampullate Spidroin Domains and Their Distinct Roles in Fibroin Solubility and Fiber Formation," PLOS One, Feb. 2013, vol. 8, issue 2, pp. 1-11.
Hagn, F., et al. "A conserved spider silk domain acts a molecular switch that controls fibre assembly." Nature, May 13, 2010, vol. 465, pp. 239-242.
Hagn, F., et al., "A conserved spider silk domain acts as a molecular switch that controls fibre assembly." Nature, May 13, 2010, vol. 465, pp. 1-2 (abstract).
Lazaris, A., et al., "Spider Silk Fibers Spun from Soluble Recombinant Silk Produced in Mammalian Cells," Science, Jan. 18, 2002, vol. 295, pp. 472-476.
Tokareva, O., et al, "Recombinant DNA production of spider silk proteins," Microbial Biotechnofogy, Nov. 2013, Thermatic Issue on Biomaterials, vol. 6, pp. 651-663.

\* cited by examiner

Fig 1

ENGINEERED SPIDER SILK PROTEINS AND USES THEREOF

This application is a National Stage application under 35 U.S.C. § 371 of International Application No. PCT/EP2017/066119, having an International Filing Date of Jun. 29, 2017, which claims the benefit of European Application Serial No. 16177521.8 filed Jul. 1, 2016. This disclosure of the prior application is considered part of (and is incorporated by reference in) the disclosure of this application.

TECHNICAL FIELD

The present invention relates to the field of engineered spider silk proteins, and methods for producing fibers of such proteins.

BACKGROUND TO THE INVENTION

Spider silk is composed of spidroins that are produced in abdominal glands. Most spiders produce up to 7 different types of silk in different glands, which are used for specific purposes and have different mechanical properties. Two of the toughest silks produced by orbweavers include the dragline silk (from the major ampullate gland) and the minor ampullate silk (from the minor ampullate gland). The majority of spidroins, including major ampullate spidroins (MaSps) and minor ampullate spidroins (MiSps), share a common architecture of a non-repetitive N-terminal domain (NT), an extensive repetitive region (REP) and a non-repetitive C-terminal domain (CT). Since spiders are territorial and produce small amounts of silk, any industrial application of spider silk requires the production of recombinant spidroins and the generation of artificial spider silk fibers. Spidroins can be produced in for example bacteria, yeast and insect cells but the recombinant proteins obtained so far are most often quite different from their natural counterparts with one or both of the terminal domains lacking, or the repeat region is engineered from iterated consensus repeats. Moreover, the produced spidroins have been obtained in too poor yields for the process to be scalable and/or have low solubility in water, probably owing in part to their inherent high tendency to self-assemble, but use of suboptimal spidroin constructs likely contribute to previous shortcomings in terms of production levels and solubility. Surprisingly, even when solvents such as hexafluoroisopropanol (HFIP) and formic acid are used, the solubility of the recombinant spidroins is far from the extreme solubility of spidroins in the native dope, which displays a protein concentration of 30-50% w/w, i.e. 300-500 mg/ml.

Progress in the analyses of the conditions in the spider silk glands and spinning ducts has unraveled that pH is gradually lowered from 7.6 to ≤5.7 along the gland. The changes in conditions lead to specific conformational changes in the terminal domains, which result in fiber formation via a lock and trigger mechanism. During storage in the silk gland, at neutral pH, the NT is monomeric and highly soluble, which may contribute to the solubility of the entire spidroin. More important for the present application is the fact that when pH is lowered in the spinning duct, NT forms stable dimers, which locks the spidroins into large networks. The effects of pH on CT are not settled, and different effects have been observed. In one study (Andersson et al, PLoS Biol 12(8): e1001921. doi:10.1371/journal.pbio.1001921) decrease in pH resulted in that CT got destabilized, unfolded and turned into β-sheet amyloid-like fibrils. The structural conversion of CT is hypothesized to trigger the transition of the repetitive region into β-sheet conformation, in analogy with the nucleation phenomenon seen in amyloid fibril formation. Dehydration of the spinning dope likely takes place along the duct of the silk gland and shear forces generated along the narrowing duct affect the spidroin terminal domains. Molecular dynamics simulations indicate that shear forces play a significant role also in the structural conversion of the repetitive region.

Engineered recombinant spider silk proteins have been described in WO2007/078239. Methods for producing polymers of spider silk proteins are described in WO2010/123450.

Given the shortcomings of the known engineered spider silk proteins and the methods of producing polymers from them, there is a need in the art for improved engineered spider silk proteins.

Thus, an object of the present invention is the provision of improved engineered spider silk proteins, in particular having high solubility in water, allowing scalable production, and being able to polymerize in a biomimetic fashion to form truly spider silk-like and useful fibers. Another object of the present invention is the provision of improved methods for producing fibers of engineered spider silk proteins, resulting in fibers having improved and useful mechanical properties, in particular as compared to known fibers in as-spun state.

Definitions

The terms spidroins and spider silk proteins are used interchangeably throughout the description and may refer to both native and recombinant proteins, dependent on the context.

The term minispidroin refers to an engineered variant of a spidroin, bearing a much shorter repetitive region than native spidroins.

Sequence identity expressed in percentage (or synonymously % identity) is defined as the value determined by comparing two optimally aligned sequences over a comparison window, wherein a portion of the sequence in the comparison window may comprise additions or deletions (i.e., gaps) as compared to the reference sequence (which does not comprise additions or deletions) for optimal alignment of the two sequences. The percentage is calculated by determining the number of positions at which identical amino acid residue occurs in both sequences to yield the number of matched positions, dividing the number of matched positions by the total number of positions in the window of comparison and multiplying the result by 100 to yield the percentage of sequence identity. Unless indicated otherwise, the comparison window is the entire length of the sequence being referred to. In this context, optimal alignment is the alignment produced by the BLASTP algorithm as implemented online by the US National Center for Biotechnology Information (see The NCBI Handbook [Internet], Chapter 16, the most recent version on the date of filing), with the following input parameters: Word length=3, Matrix=BLOSUM62, Gap cost=11, Gap extension cost=1.

The term % similarity, as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

The terms soluble and solution in the present context have the meaning that the protein in question is dissolved in a solvent with no visible aggregates and does not precipitate from the solvent at 60 000 g.

All the Genbank accession numbers cited herein refer to entries as in the most recent version of the Genbank database on the date of filing.

BRIEF DESCRIPTION OF THE FIGURES

FIG. 1: Alignment of spidroin NT domains listed in Table 2 using ClustalW.

160223_1: Spun into 500 mM NaAc, 200 mM NaCl, pH 5.
160223_2: Spun into 500 mM NaAc, 200 mM NaCl, 15% PEG, pH 5.
160223_4: Post-stretched in 50% methanol and 500 mM NaAc, 200 mM NaCl, pH 5
160223_5: Post-stretched in 30% PEG.

Figure 15:
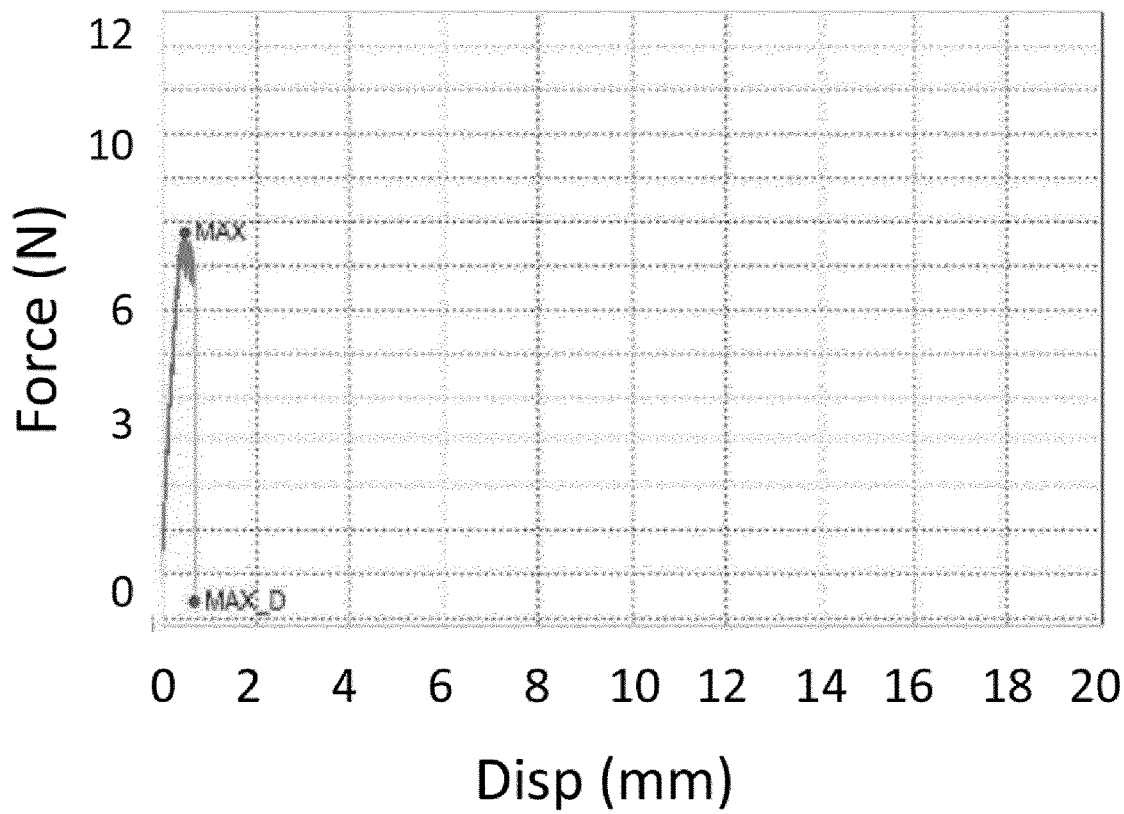

FIG. 15. 160303_4: Force/displacement curve of NT2RepCT fibers spun into 500 mM NaAc, 200 mM NaCl, pH 4.25.

Figure 16:
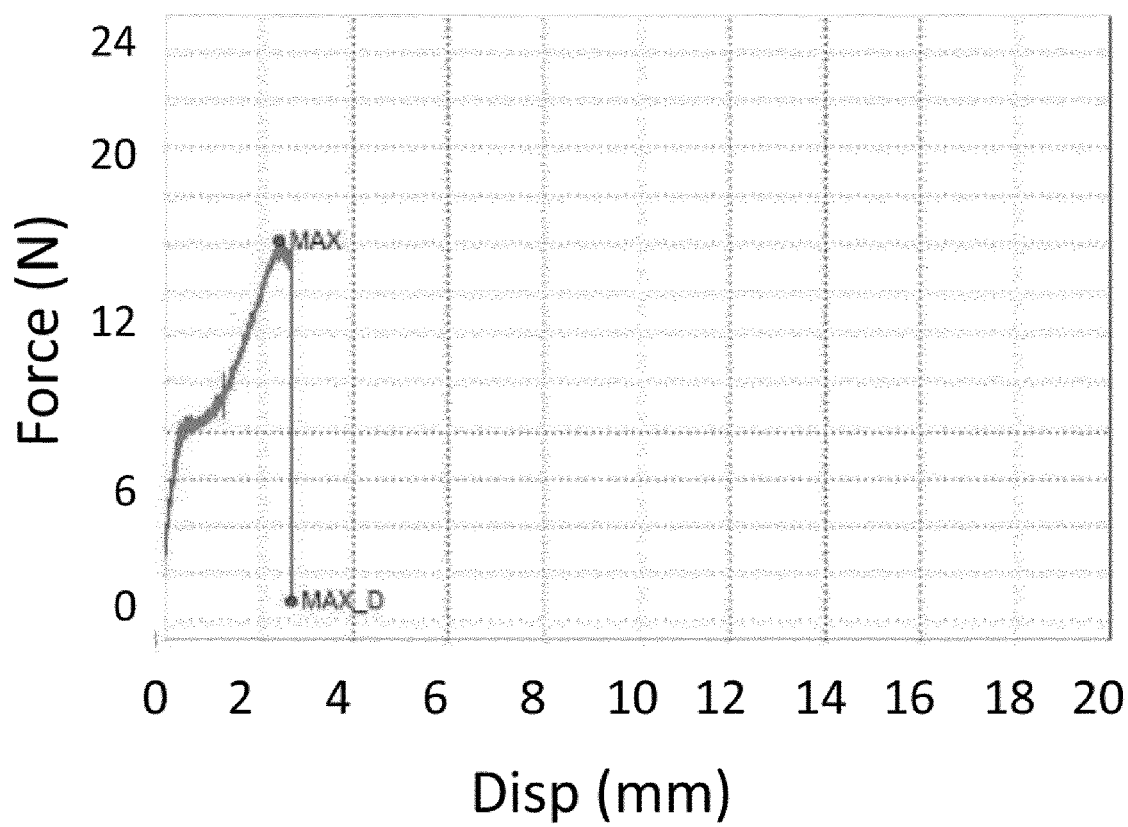

FIG. 16. 160303_5a: Force/displacement curve of NT2RepCT fibers spun into 500 mM NaAc, 200 mM NaCl, pH 5 at room temperature and, subsequently post-stretched in 80% aqueous isopropanol.

Figure 17:
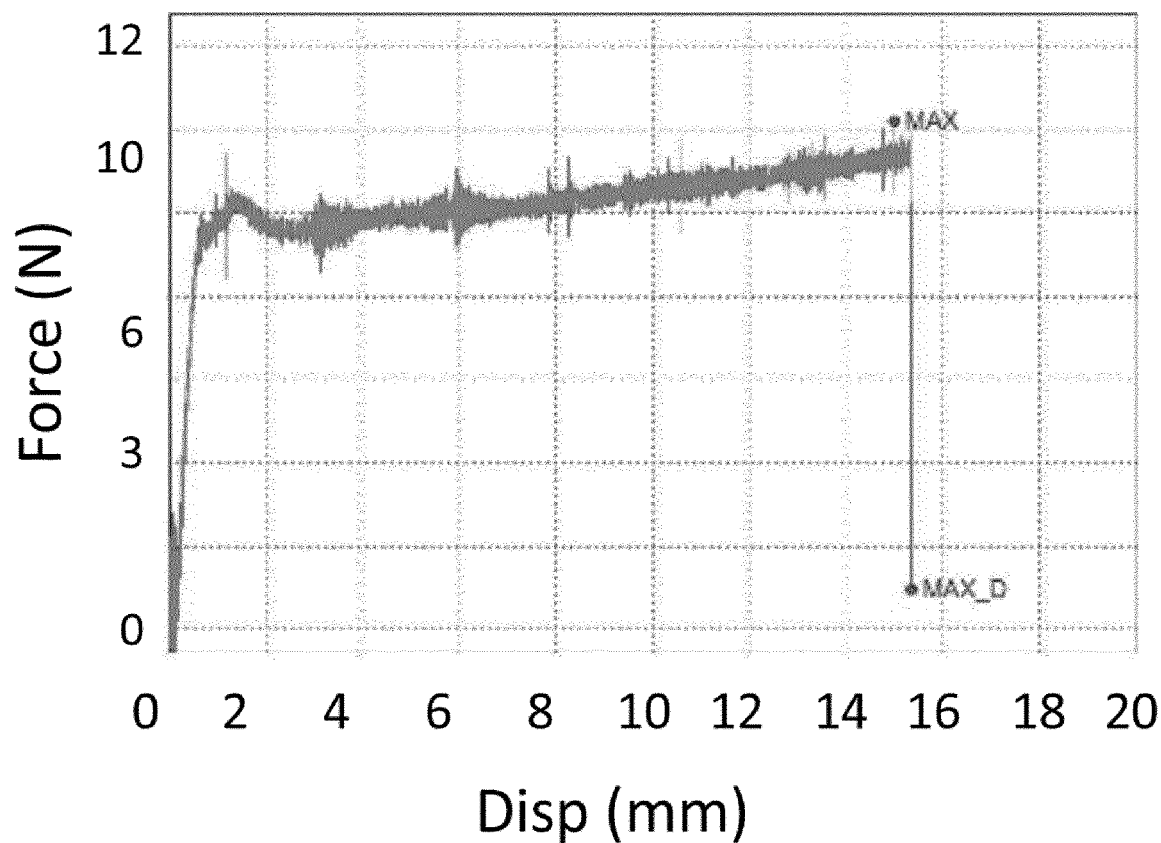

FIG. 17. 160303_5b: Force/displacement curve of NT2RepCT fibers spun into 500 mM NaAc, 200 mM NaCl, pH 5 at room temperature and subsequently dipped in 80% aqueous isopropanol.

Figure 18:
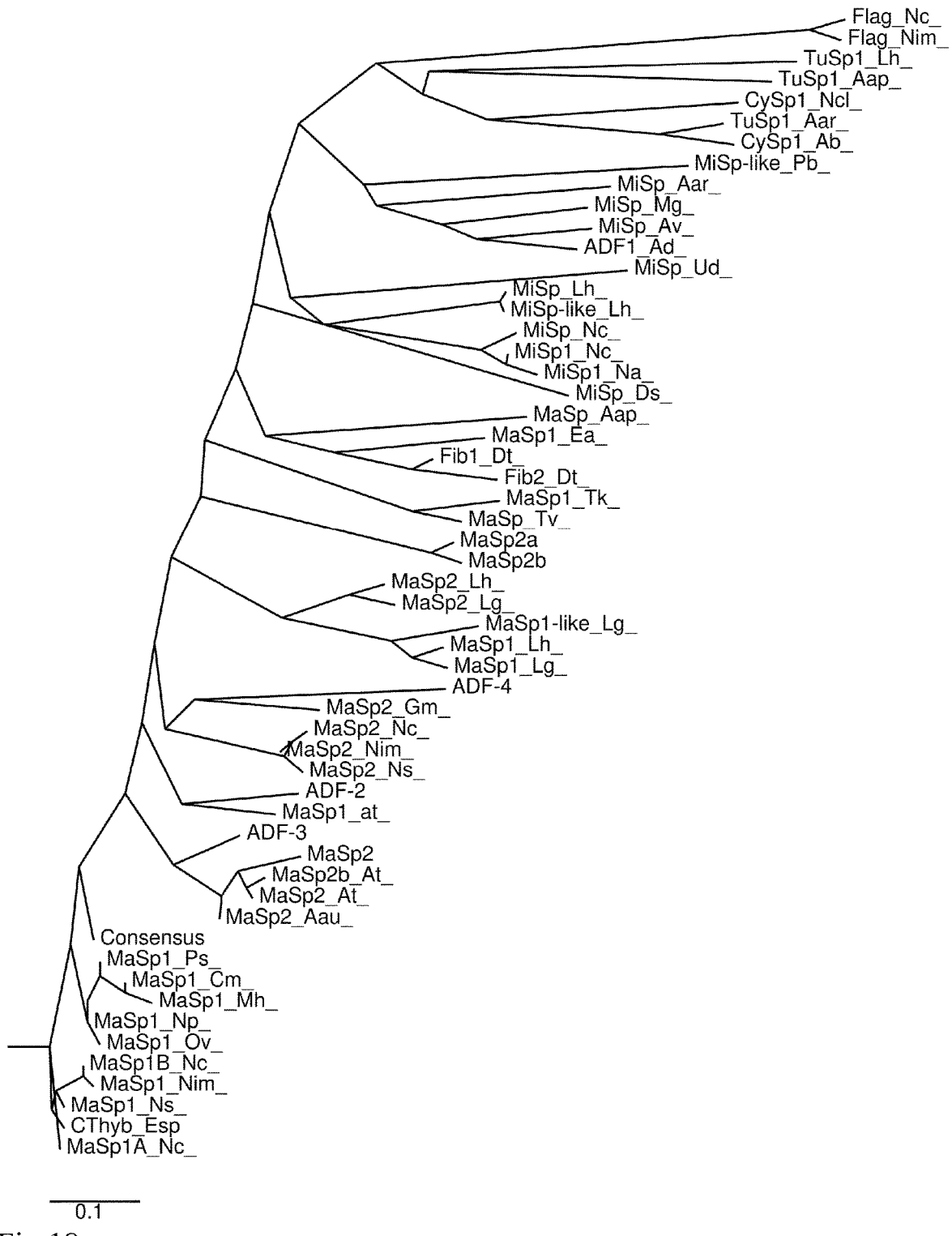

FIG. 18. Phylogenetic tree of the CT-domain sequences in Table 1.

Figure 19:
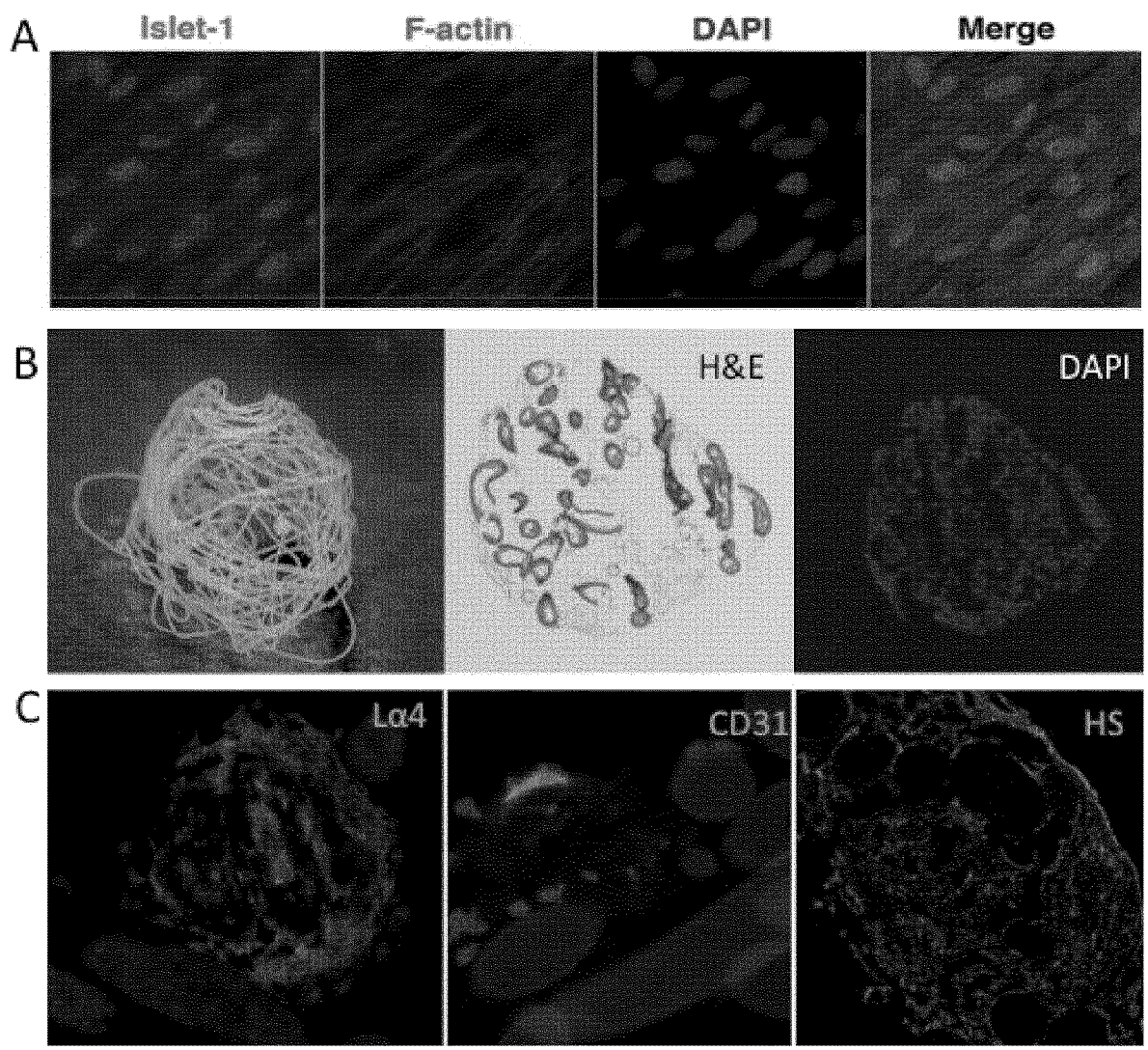

FIG. 19 A). hfcMSCs maintain the expression of Isl1+ and F-actin when expanded on spider silk foam. DAPI stain (blue) shows nuclei. B). Spun fibers can be assembled into ~1 cm Ø balls (left). Fetal cardiac progenitor cells were grown on dense fiber balls, which were sectioned, and stained with haematoxylin and eosin (H&E;middle) and DAPI. C) Cryosectioned cells on spider silk balls show expression of laminin α4, CD31 and heparansulfate.

Figure 20:
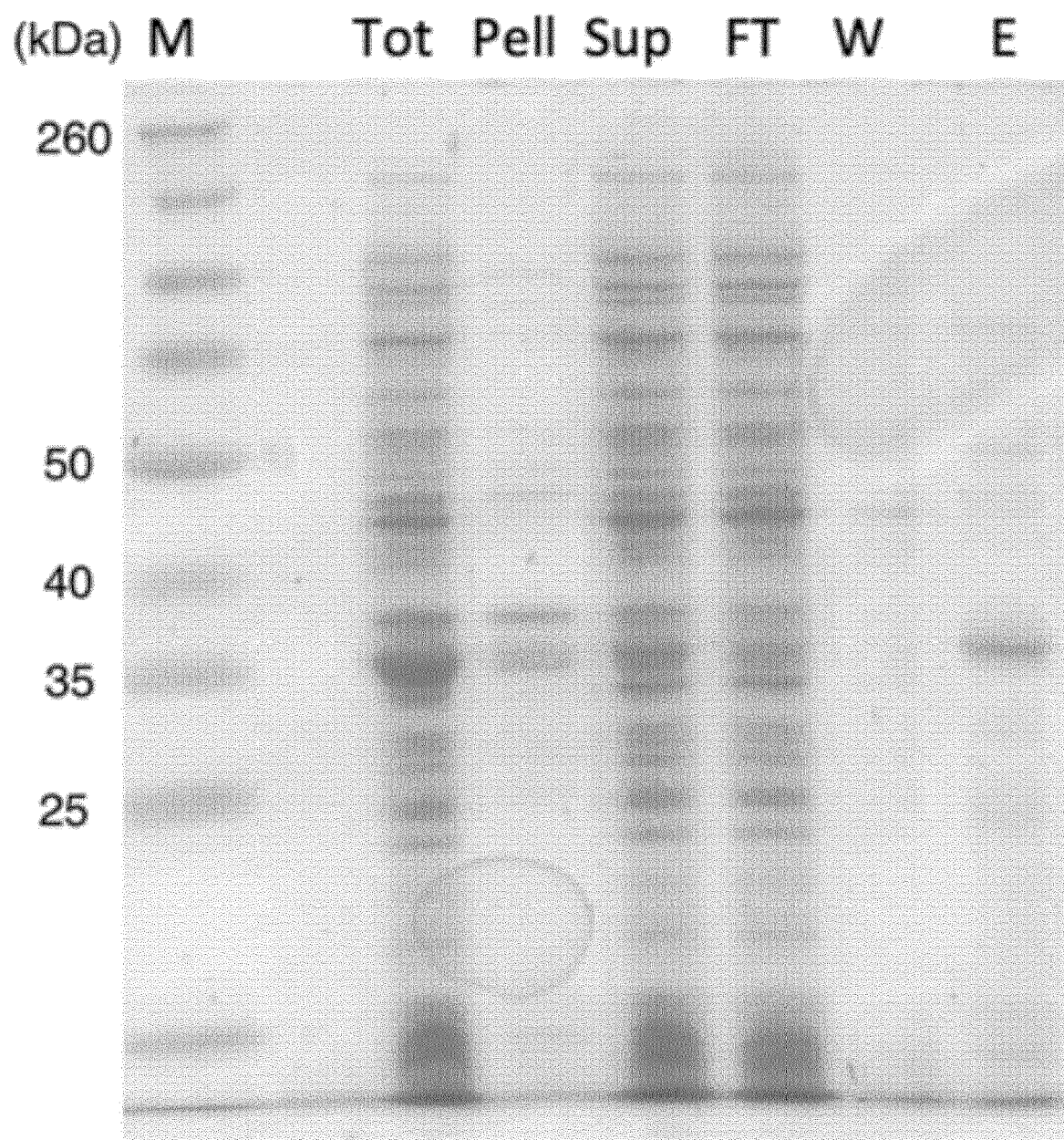

FIG. 20. SDS-PAGE of purified NT2RepCT(MiSp Ds) and different purification steps. M=Spectra Broadrange protein marker (sizes in kilodalton is shown to the left), Tot=total cell lysate, Pell=pellet, Sup=supernatant after centrifugation of whole cell lysate, FT=flow through Ni-NTA column, W=wash, E=target protein NT2RepCT(MiSp Ds) eluted from the Ni-NTA column.

Figure 21:
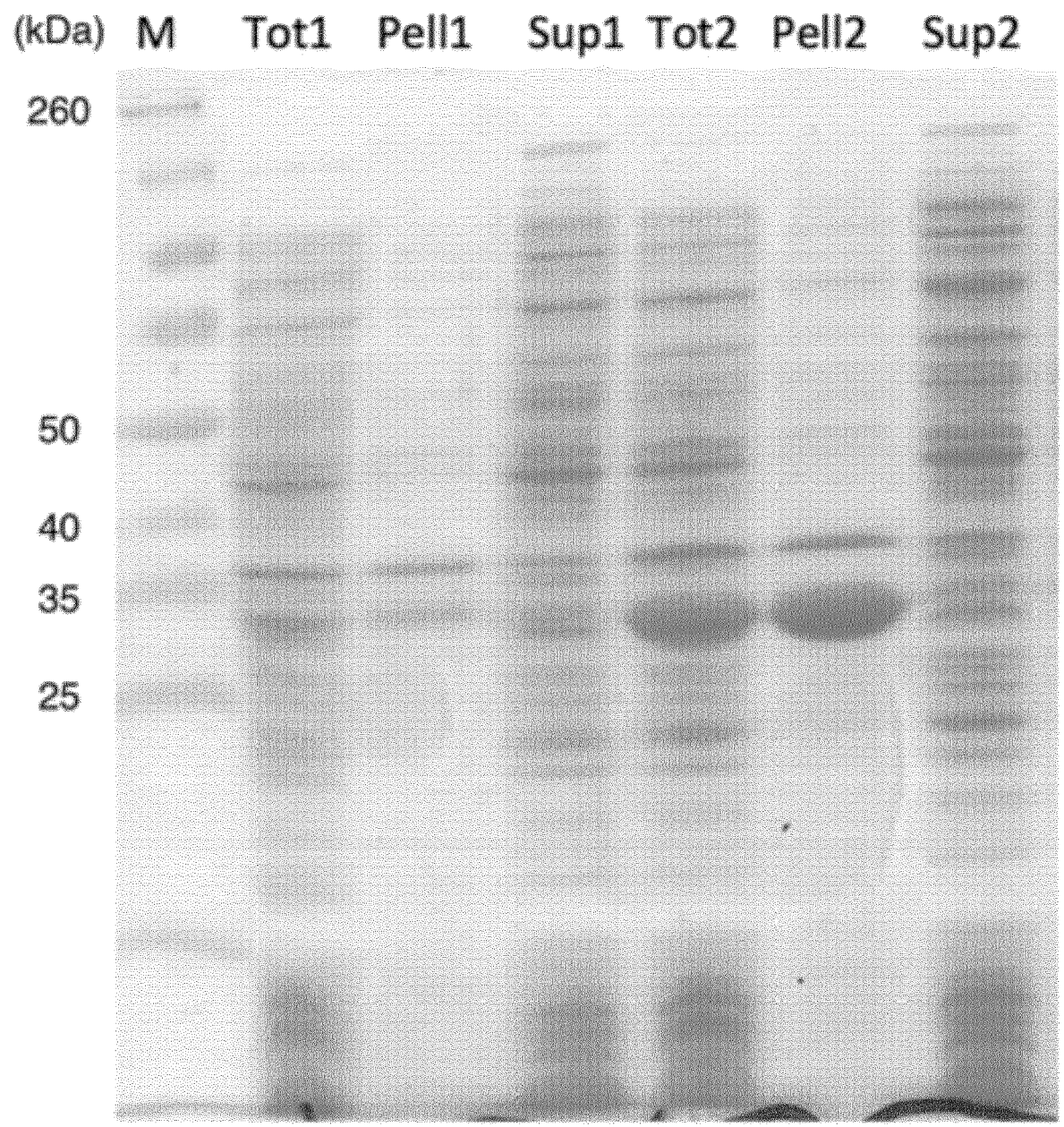

FIG. 21. SDS-PAGE of (1)NT2RepCT(MaSp1 Ea) and (2) NT2RepCT(ADF-4). M=Spectra Broadrange protein marker (sizes in kilodalton is shown to the left), Tot=total cell lysate, Pell=pellet, Sup=supernatant after centrifugation of whole cell lysate.

Figure 22:
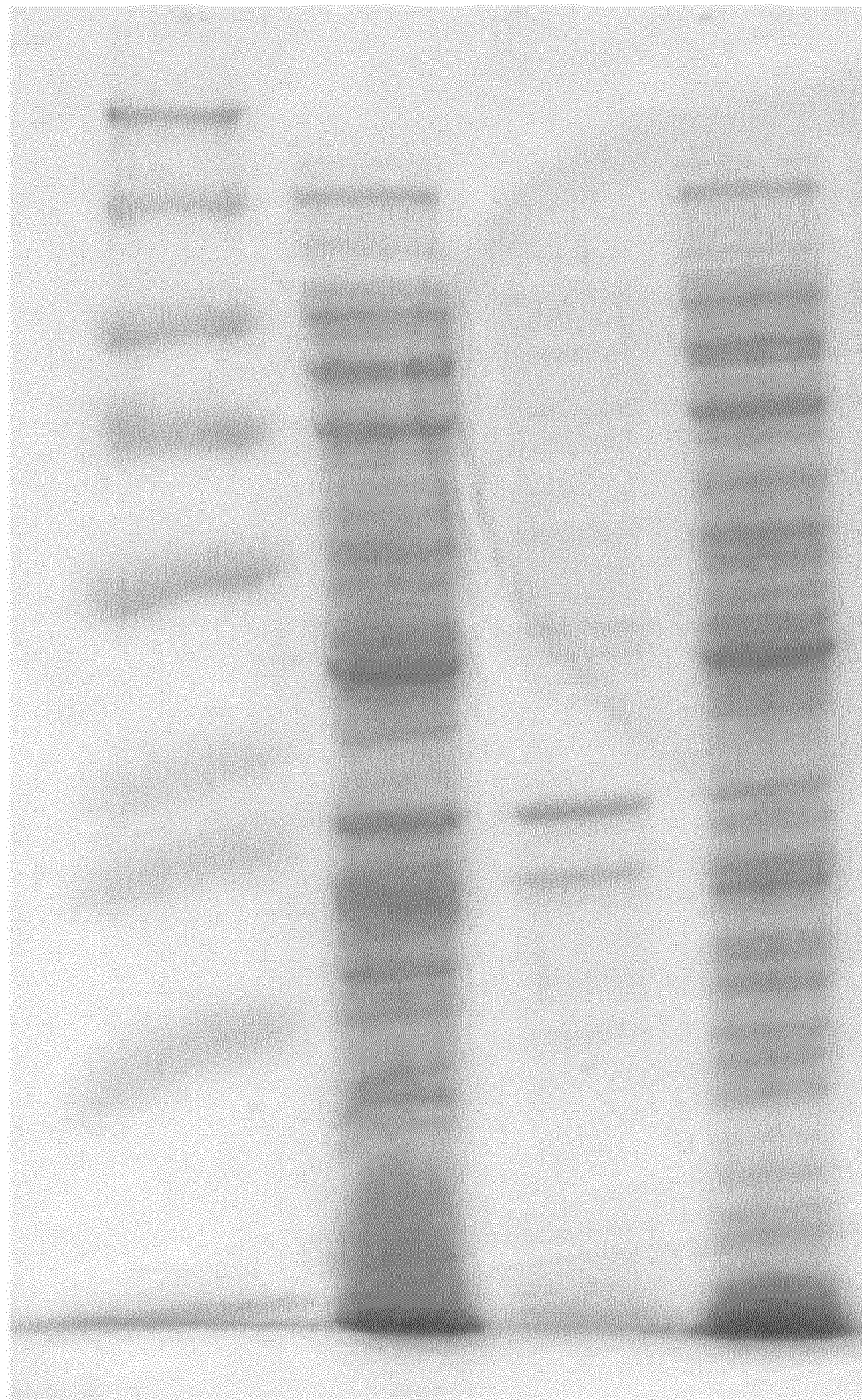

FIG. 22. SDS-PAGE of NT2RepCT(MiSp Lh). M=Spectra Broadrange protein marker (sizes in kilodalton is shown to the left), Tot=total cell lysate, Pell=pellet, Sup=supernatant after centrifugation of whole cell lysate.

SUMMARY OF THE INVENTION

The present invention relates to the following items. The subject matter disclosed in the items below should be regarded disclosed in the same manner as if the subject matter were disclosed in patent claims.

1. A recombinant spider silk protein, consisting of no more than 800 amino acids, comprising a set of domains arranged according to the formula (NT)-REP-CT, wherein:
   a. the optional NT-domain, if present, consists of a sequence of 100 to 160 amino-acid residues derived from the N-terminal domain of a spider silk protein;
   b. the REP-domain consists of a sequence of 30 to 600 amino acid residues derived from the repetitive segment of a spider silk protein;
   c. the CT-domain consists of a sequence of 70 to 120 amino acid residues derived from the C-terminal domain of a spider silk protein, selected from:
      i. a sequence of 72 to 110 amino acid residues derived from the C-terminal domain of a spider silk protein, wherein the sequence comprises at least 7 residues independently selected from K, R, E and D;
      ii. a sequence having at least 81% identity to SEQ ID NO: 64 or any one of SEQ ID NOs: 62-65 or 67-73; and
      iii. a sequence having at least 70% identity to SEQ ID NO: 64 or any one of SEQ ID NOs: 62-65 or 67-73, wherein the sequence comprises at least 7 residues independently selected from K, R, E and D.
2. The recombinant spider silk protein according to any of the preceding items, wherein the CT-domain consists of a sequence of 72 to 110 amino acid residues derived from the C-terminal domain of a spider silk protein, wherein the sequence comprises at least 7 residues independently selected from K, R, E and D
3. The recombinant spider silk protein according to any of the preceding items, wherein the CT-domain consists of a sequence having at least 81%, preferably at least 82%, 83%, 84%, 85%, 86%, 87%, 88% or 89%, more preferably at least 90%, most preferably at least 95% sequence identity to SEQ ID NO: 64 or any one of SEQ ID NOs: 62-65 or 67-73.
4. The recombinant spider silk protein according to any of the preceding items, wherein the CT-domain consists of a sequence having at least 81%, preferably at least 82%, 83%, 84%, 85%, 86%, 87%, 88% or 89%, more preferably at least 90%, most preferably at least 95% sequence identity to SEQ ID NO: 64.
5. The recombinant spider silk protein according to any of the preceding items, wherein the CT-domain consists of a sequence having at least 70%, preferably at least 72%, 75%, 77%, 80%, 83%, 85%, 87% or 89%, more preferably at least 90%, most preferably at least 95% sequence identity to SEQ ID NO: 64, wherein the sequence comprises at least 7 residues independently selected from K, R, E and D.
6. The recombinant spider silk protein according to any of the preceding items, wherein the CT-domain consists of at least 80, preferably at least 90, amino acid residues.
7. The recombinant spider silk protein according to any of the preceding items, wherein the CT-domain consists of less than 110 amino acid residues.
8. The recombinant spider silk protein according to any of the preceding items, wherein the CT-domain consists of 87-97 amino acid residues.
9. The recombinant spider silk protein according to any of the preceding items, wherein the CT-domain sequence does not comprise a C residue at the beginning of helix 4.
10. The recombinant spider silk protein according to any of the preceding items, wherein the CT-domain sequence does not comprise a C residue at a position aligning with the positions 47-55 of SEQ ID NO: 49.
11. The recombinant spider silk protein according to any of the preceding items, wherein the NT-domain is present.
12. The recombinant spider silk protein according to any of the preceding items, wherein the NT-domain is present and consists of a sequence derived from the N-terminal domain of a major ampullate gland spider silk protein.
13. The recombinant spider silk protein according to any of the preceding items, wherein the NT-domain is present and consists of a sequence having at least 50% identity to SEQ ID NO: 2 and/or at least 80% identity to SEQ ID NO: 1 or any individual amino acid sequence in Table 2.
14. The recombinant spider silk protein according to any of the preceding items, wherein the NT-domain is present and consists of a sequence having at least 80% identity to SEQ ID NO: 1.
15. The recombinant spider silk protein according to any of the preceding items, wherein the NT-domain is present and consists of at least 110, preferably at least 120, amino acid residues.
16. The recombinant spider silk protein according to any of the preceding items, wherein the NT-domain is present and consists of at most 160, preferably less than 140 amino acid residues.
17. The recombinant spider silk protein according to any of the preceding items, wherein the NT-domain is present and consists of 130-140 amino acid residues.
18. The recombinant spider silk protein according to any of the preceding items, wherein the REP domain comprises alternating alanine-rich A-segments and glycine-rich G-segments.
19. The recombinant spider silk protein according to any of the preceding items, wherein the REP domain comprises alanine-rich A-segments and glycine-rich G-segments, wherein the sum of the number of A segments and the number of G segments in the REP-domain is 3 to 30, preferably 4-20, more preferably 4-10, most preferably 4-8.
20. The recombinant spider silk protein according to any of the preceding items, wherein the REP domain comprises alanine-rich A-segments and glycine-rich G-segments, wherein each A segment is an amino acid sequence of from 8 to 20 amino acid residues, wherein at least 60%, preferably at least 65%, more preferably at least 70%, most preferably at least 75% of the amino acid residues are Ala.
21. The recombinant spider silk protein according to any of the preceding items, wherein the REP domain comprises alanine-rich A-segments and glycine-rich G-segments, wherein each G segment is an amino acid sequence of from 12 to 40 amino acid residues, wherein at least 30%, preferably at least 35%, most preferably at least 40% of the amino acid residues are Gly.

22. The recombinant spider silk protein according to any of the preceding items, wherein the REP domain comprises alanine-rich A-segments and glycine-rich G-segments, wherein each A segment contains at least one stretch of 5 consecutive, preferably 6 consecutive A residues.
23. The recombinant spider silk protein according to any of the preceding items, wherein the REP domain comprises alanine-rich A-segments and glycine-rich G-segments, wherein each G segment contains at least one, preferably at least two GGX motif(s), where X designates any amino acid.
24. The recombinant spider silk protein according to any of the preceding items, wherein the REP-domain is selected from the group consisting of L(AG)$_n$L, L(AG)$_n$AL, L(GA)$_n$L, L(GA)$_n$GL, LG(AG)$_n$L, wherein n is an integer from 2 to 10;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 30 amino acid residues, preferably 0-25.

25. The recombinant spider silk protein according to item 24, wherein each individual A segment has at least 80% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3; and each individual G segment has at least 80% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3.
26. The recombinant spider silk protein according to any of items 24-25 wherein n is 2 or 4.
27. The recombinant spider silk protein according to item 26, wherein the selected REP domain is LG(AG)$_2$L or LG(AG)$_4$L.
28. The recombinant spider silk protein according to item 27, wherein the selected REP domain is LG(AG)$_2$L.
29. The recombinant spider silk protein according to any of the preceding items, wherein the REP-domain consists of 40-600, preferably 50-500, more preferably 60-400, most preferably 70-300 amino acids.
30. The recombinant spider silk protein according to any of the preceding items, wherein the spider silk protein comprises a set of domains according to the formula NT-L-REP-L-CT, wherein each individual L segment is a linker amino acid sequence of from 1 to 20 amino acid residues.
31. The recombinant spider silk protein according to any of the preceding items, wherein the spider silk protein consists of no more than 600, preferably no more than 500, more preferably no more than 400, yet more preferably no more than 300, most preferably no more than 250 amino-acid residues in total.
32. The recombinant spider silk protein according to any of the preceding items, wherein the protein exhibits highly pH-dependent solubility.
33. The recombinant spider silk protein according to any of the preceding items, wherein the protein exhibits highly pH-dependent solubility defined as least 10 times, preferably 50 times, more preferably 100 times higher solubility in aqueous 20 mM Tris-HCl pH8.0 buffer than in aqueous 500 mM Na-acetate, 200 mM NaCl at pH5.0.
34. The recombinant spider silk protein according to any of the preceding items, wherein the protein is soluble in aqueous 20 mM Tris-HCl pH8.0 buffer and polymerizes in aqueous 500 mM Na-acetate, 200 mM NaCl at pH5.0, at a concentration of 50 mg/ml, preferably at a concentration of 100 mg/ml, more preferably 200 mg/ml, most preferably 300 mg/ml.
35. The recombinant spider silk protein according to any of the preceding items, comprising a sequence having at least 80%, preferably at least 85%, more preferably at least 90%, most preferably at least 95% sequence identity to SEQ ID NO: 11.
36. The recombinant spider silk protein according to any of the preceding items, consisting of a sequence identical to SEQ ID NO: 11.
37. A non-denaturing solution of a spider silk protein according to any of the preceding items, having a protein concentration of said spider silk protein of at least 100 mg/ml, preferably 150 mg/ml, most preferably 200 mg/ml.
38. A polymer of a spider silk protein according to any of items 1-36, preferably a fiber, film, foam, net or mesh.
39. The polymer according to item 38, being a fiber having a length of at least 10 cm, preferably at least 1 m, more preferably at least 5 m, yet more preferably at least 10 m, still more preferably at least 50 m, most preferably at least 100 m.
40. The polymer according to any of items 38-39, being a fiber having diameter≤100 μm, preferably less than 50 μm, more preferably less than 20 μm, most preferably less than 10 μm.
41. The polymer according to any of items 38-40, having toughness of ≤3 MJ/m$^3$, preferably ≤10 MJ/m$^3$, more preferably ≤20 MJ/m$^3$, most preferably ≤40 MJ/m$^3$.
42. A method for producing a polymer of a spider silk protein, comprising the steps of:
   a. providing a first liquid medium comprising a spider silk protein according to any of items 1-36 in solution in said medium at a concentration of at least 100 mg/ml, preferably 200 mg/ml, most preferably 300 mg/ml;
   b. adjusting the properties of the first liquid medium such that it allows polymerisation of said spider silk protein;
   c. allowing the spider silk protein to form polymers; and
   d. isolating the spider silk protein polymers.
43. The method according to item 42, wherein the properties of the first liquid medium are adjusted by extruding the solution of a spider silk protein into a second fluid medium having properties that allow polymerisation of said spider silk protein.
44. The method according to any of items 42-43, wherein the first liquid medium in step (a) has a pH of at least 6.4.

45. The method according to any of items 42-44, wherein the first liquid medium in step (a) has a salt concentration of less than 100 mM.
46. The method according to any of items 42-45, wherein the first liquid medium in step (a) is an aqueous solution comprising less than 10% (v/v) of organic solvents.
47. The method according to any of items 42-46, wherein the properties of the first liquid medium in steps (b)-(d) are adjusted to pH 6.3 or below, in the presence of a sufficient salt concentration for polymerisation of said spider silk protein.
48. The method according to any of items 42-47, wherein the properties of the first liquid medium in steps (b)-(d) are adjusted to at least 100 mM salt concentration and to pH 6.3 or below.
49. The method according to any of items 42-48, wherein the properties of the first liquid medium in steps (b)-(d) are adjusted to having a concentration of an organic solvent sufficient to induce polymerization.
50. The method according to item 42, wherein the second fluid medium has pH 6.3 or below, and a sufficient salt concentration for polymerisation of said spider silk protein.
51. The method according to any of items 42 or 50, wherein the second fluid medium comprises an organic solvent at a concentration sufficient to induce polymerization.
52. The method according to any of items 42 or 50-51, wherein the second fluid medium comprises a hygroscopic polymer, such as PEG.
53. The method according to any of items 42 or 50-52, wherein the extrusion is through a capillary having an opening with a cross-sectional area in the interval 20-50000 $\mu m^2$, preferably 30-30000 $\mu m^2$, more preferably 40-10000 $\mu m^2$, yet more preferably 50-5000 $\mu m^2$, most preferably 70-800 $\mu m^2$.
54. The method according to any of items 42 or 50-52, wherein the extrusion is performed at a linear flow rate of 0.1-500 mm/s, more preferably 0.5-200 mm/s, most preferably 1-100 mm/s.
55. The method according to any one of items 42-54, wherein said polymer is a fiber, film, foam, net or mesh, preferably a fiber, more preferably a polymer according to any of items 38-41.
56. A nucleic acid encoding for a protein according to any of items 1-36.
57. An expression vector comprising a nucleic acid according to item 56 operatively coupled to a promoter.
58. A host cell comprising a nucleic acid according to item 56, or an expression vector according to item 57.
59. A method of producing a recombinant spider silk protein, comprising:
    a. Culturing a host cell according to item 58 in conditions allowing production of the protein;
    b. Isolating said protein from said culture.
60. The method according to any of items 42-55, wherein the polymer is extruded in a 3D-printing apparatus.
61. A use of a spider silk protein according to any of items 1-36, or a polymer according to any of items 38-41, in the manufacture of an implantable material or a cell culture scaffold.
62. A use of a spider silk protein according to any of items 1-36, or a polymer according to any of items 38-41 as an implantable material or a cell culture scaffold.

DETAILED DESCRIPTION

The inventors postulated that a prerequisite that needs to be fulfilled in order to realize biomimetic spinning of artificial spider silk is to obtain spidroins that are pH responsive and display solubility levels in water that equal those of spidroins in the native spinning dope. It struck the inventors that the aqueous solubility and pH responsiveness of NT and CT, respectively, might differ between spidroins from different spider species and silk types. The inventors further hypothesized that a recombinant minispidroin that comprises a highly soluble NT and a likewise very soluble CT would be fully pH sensitive and advantageous from a solubility point-of-view. To test the hypothesis, the inventors designed a minispidroin composed of NT from *E. australis* MaSp1 and CT from *A. ventricosus* MiSp bracketing a short repetitive region from *E. australis* (Example 1), and found that the minispidroin indeed has unprecedented solubility combined with a capability to form useful, and in certain respects, superior fibers in a biomimetic, pH-dependent manner (Examples 2-10), compared to prior art minispidroins (comparative Example 11).

Further experiments show that a minispidroin comprising CT from *A. ventricosus* MiSp coupled to a short repetitive region from *E. australis* (Example 12) also is able to form fibers in a pH-dependent manner never previously seen with minispidroins not comprising an NT-domain.

Yet further studies on an engineered minispidroin with twice as long repetitive region than in Example 1 showed that advantages of combining highly soluble and pH-sensitive NT and CT are not limited to minispidroins with very short repetitive regions (Example 13).

Designed Spider Silk Proteins

In a first aspect of the present invention, there is provided a recombinant spider silk protein, preferably consisting of no more than 800 amino acids, comprising a set of domains arranged according to the formula (NT)-REP-CT, wherein:
    a. the optional NT-domain, if present, consists of a sequence of 100 to 160 amino-acid residues derived from the N-terminal domain of a spider silk protein;
    b. the REP-domain consists of a sequence of 30 to 600 amino acid residues derived from the repetitive segment of a spider silk protein;
    c. the CT-domain consists of a sequence of 70 to 120 amino acid residues derived from the C-terminal domain of a spider silk protein selected from:
        i. a sequence of 72 to 110 amino acid residues derived from the C-terminal domain of a spider silk protein, wherein the sequence comprises at least 7 residues independently selected from K, R, E and D;
        ii. a sequence having at least 81% identity to SEQ ID NO: 15 or any one of SEQ ID NOs: 62-65 or 67-73; and
        iii. a sequence having at least 70% identity to SEQ ID NO: 64 or any one of SEQ ID NOs: 62-65 or 67-73, wherein the sequence comprises at least 7 residues independently selected from K, R, E and D.

Following convention, the formula is read as N-terminus being on the left and the C-terminus on the right side of the formula.

Properties of the CT Domain

The role of the NT domain in physiological spider silk polymerization has been recognized earlier (see e.g. WO2010/123450). The extremely high solubility of the NT domain is thought to contribute to making the extremely high protein concentration possible in the physiological (native) spider silk dope, and it has been recognized that the highly pH-dependent properties of the NT domains is a crucial factor for allowing rapid polymerisation of the dope.

In contrast, most of the CT domains from the major ampullate gland silk (that has been studied most) do not exhibit extreme solubility nor do they exhibit pH-sensitive solubility in the pH 5-7.5 range.

However, the inventors have discovered that certain CT domains derived from other types of silk such as the minor ampullate gland silk do in fact exhibit extreme solubility, which is pH-dependent.

When analyzing primary structure alignments of CTs it struck the inventors that they differ in the number of charged amino acid residues, i.e. the CT from *Euprosthenops australis* MaSp1 contains four charged residues while the *Araneus ventricosus* MiSp CT has seven charged residues. The inventors therefore hypothesized that the number of charges in the CT positively correlates to the solubility of the CT and therefore using CTs with a high number of charged amino acid residues could be beneficial for the solubility of recombinantly produced spidroins. Thus, without wishing to be bound by a particular theory, the inventors believe that residues that are charged in the physiological conditions in the spider silk gland (K, R, E and D) may be important for the solubility and the pH-dependency. Histidine is not regarded as charged in this context, as it is to a significant extent non-charged at the relevant pH in said physiological conditions.

As shown in Table 1 below, the major ampullate gland spider silk CT-domains, which to the extent they have been studied, do not appear to exhibit extreme solubility and/or pH-dependent solubility, have less than 7 of these charged residues. In contrast, most minor ampullate gland spider silk CT-domains have at least 7 of these charged residues. This observation was validated experimentally (see Example 15) by comparing different CT-domains differing in charged residue content either naturally or by genetic engineering.

Thus, the CT-domain sequence may be a sequence of 72 to 110 amino acid residues derived from the C-terminal domain of a spider silk protein, wherein the sequence comprises at least 7 residues independently selected from K, R, E and D.

Preferably, the CT-domain sequence does not comprise a C residue at the beginning of helix 4, as defined according to the NMR structures with PDB id 2MFZ (MiSp CT, *A. ventricosus*) or 2MOM (MiSp *N. antipodiana*). If a structure of a CT domain has not been experimentally determined, a secondary structure prediction algorithm, such as psipred, may be used to define helix 4. Said C residue is a characteristic feature of major ampullate gland CT-domains but is generally missing in minor ampullate gland CT-domains. Preferably, the CT-domain sequence does not comprise a C residue at a position aligning with the positions 47-55 of SEQ ID NO: 49.

The CT-domain may be a sequence having at least 81%, preferably at least 82%, 83%, 84%, 85%, 86%, 87%, 88% or 89%, more preferably at least 90%, most preferably at least 95% sequence identity to any one of SEQ ID NOs: 62-65 or 67-73.

The CT-domain may be a sequence having at least 81%, preferably at least 82%, 83%, 84%, 85%, 86%, 87%, 88% or 89%, more preferably at least 90%, most preferably at least 95% sequence identity to SEQ ID NO: 64.

The CT domain sequence may be a sequence having at least 70%, preferably at least 72%, 75%, 77%, 80%, 83%, 85%, 87% or 89%, more preferably at least 90%, most preferably at least 95% sequence identity to SEQ ID NO: 64, or any one of SEQ ID NOs: 62-65 or 67-73, with the proviso that the sequence comprises at least 7 residues independently selected from K, R, E and D.

TABLE 1

Exemplary spidroin CT domains

| Designation | Species and Spidroin | Genbank accession no | AA sequence | No. charged residues (K/R/E/D) | SEQ ID NO |
|---|---|---|---|---|---|
| MiSp-like(Pb) | MiSp-like protein [*Parawixia bistriata*] | ADG57595.1 | GAGAAAASGATGRVANSLGAMASGGI NALPGVFSNIFSQVSAASGGASGGAVLV QALTEVIALLLHILSSASIGNVSSQGLEGS MAIAQQAIGAYAG | 3 | 19 |
| MaSp1(Tk) | *Tetragnatha kauaiensis* MaSp1 | AF350285 | SLLSSPASNARISSAVSALASGAASGPGY LSSVISNVVSQVSSNSGGLVGCDTLVQA LLEAAAALVHVLASSSGGQVNLNTAGYT SQL | 3 | 20 |
| MaSp2(At) | major ampullate spidroin 2 [*Argiope trifasciata*] | AAZ15372.1 | AAASRLSSPQASSRVSSAVSTLVSSGPTN PASLSNAISSVVSQVSASNPGLSGCDVL VQALLEIVSALVHILGSSSIGQINYAASSQ YAQMVG | 4 | 21 |
| MaSp1A(Nc) | major ampullate spidroin 1 [*Nephila clavipes*] | AAT75312.1 | SAASRLSSPEASSRVSSAVSNLVSSGPTN SAALSSTISNVVSQIGASNPGLSGCDVLV QALLEVVSALIHILGSSSIGQVNYGSAGQ ATQIVGQSIYQALG | 5 | 22 |
| MaSp1B(Nc) | major ampullate spidroin 1 [*Nephila clavipes*] | AAT75311.1 | AAASRLSSPQASSRVSSAVSNLVASGPT NSAALSSTISNVVSQIGASNPGLSGCDVL IQALLEVVSALIHILGSSSIGQVNYGSAG QATQIVGQSVYQALG | 4 | 23 |
| MaSp1(Lh) | major ampullate spidroin 1 [*Latrodectus hesperus*] | ABR68856.1 | AAASALAAPATSARISSHASALLSNGPT NPASISNVISNAVSQISSSNPGASACDVL VQALLELVTALLTIIGSSNIGSVNYDSSGQ YAQVVTQSVQNAFA | 4 | 24 |

TABLE 1 -continued

Exemplary spidroin CT domains

| Designation | Species and Spidroin | Genbank accession no | AA sequence | No. charged residues (K/R/E/D) | SEQ ID NO |
|---|---|---|---|---|---|
| MaSp2(Lh) | major ampullate spidroin 2 [*Latrodectus hesperus*] | ABD66603.1 | SAASALSSPTTHARISSHASTLLSSGPTN AAALSNVISNAVSQVSASNPGSSSCDVL VQALLEIITALISILDSSVGQVNYGSSGQ YAQIVGQSMQQAMG | 4 | 25 |
| MaSp1-like(Lg) | major ampullate spidroin 1-like protein [*Latrodectus geometricus*] | AAZ15321.1 | PAASALAAPATSARISSHALTLLSNGPTN PASISNVISNAVSQISSSNPGYSSCDILVQ ALLELVTALLTIIGSSNVNDINYGSSGQYA QMVSQSVQNVFG | 4 | 26 |
| MaSp1(Ea) | major ampullate spidroin 1 [*Euprosthenops australis*] | CAJ00428.1 | NSVSRLSSPSAVSRVSSAVSSLVSNGQV NMAALPNIISNISSSVSASAPGASGCEVI VQALLEVITALVQIVSSSSVGYINPSAVN QITNVVANAMAQVMG | 4 | 27 |
| Flag(Nc) | flagelliform silk protein [*Nephila clavipes*] | AAC38847.1 | PGSPGGAYYPSSRVPDMVNGIMSAMQ GSGFNYQMFGNMLSQYSSGSGTCNPN NVNVLMDALLAALHCLSNHGSSSFAPS PTPAAMSAYSNSVGRMFAY | 4 | 28 |
| Flag(Nim) | flagelliform silk protein [*Nephila inaurata madagascariensis*] | AAF36092.1 | GPGSGGSYYPSSRVPDMVNGIMSAMQ GSGFNYQMFGNMLSQYSSGSGSCNPN NVNVLMDALLAALHCLSNHGSSSFAPS PTPAAMSAYSNSVGRMFAY | 4 | 29 |
| MaSp2(Lg) | major ampullate spidroin 2 [*Latrodectus geometricus*] | AAK30604.1 | SAASALSSPTTHARISSHASTLLSSGPTNS AAISNVISNAVSQVSASNPGSSSCDVLV QALLELITALISIVDSSNIGQVNYGSSGQY AQMVG | 4 | 30 |
| MaSp1(Lg) | major ampullate spidroin 1 [*Latrodectus geometricus*] | AAK30602.1 | AAASALAAPATSARISSHASTLLSNGPTN PASISNVISNAVSQISSSNPGASSCDVLV QALLELVTALLTIIGSSNVGNVNYDSSGQ YAQVVSQSVQNAFV | 4 | 31 |
| ADF1(Ad) | fibroin-1 [*Araneus diadematus*] | | GAVNRLSSAGAASRVSSNVAAIASAGA AALPNVISNIYSGVLSSGVSSSEALIQALL EVISALIHVLGSASIGNVSSVGVNSALNA VQNAVGAYAG | 4 | 32 |
| MaSp1(at) | *Argiope trifasciata* MaSp1 | AF350266 | SRLSSPGAASRVSSAVTSLVSSGGPTNSA ALSNTISNVVSQISSSNPGLSGCDVLVQA LLEIVSALVHILGSANIGQVNSSGVGRSA SIVGQSINQAFS | 5 | 33 |
| MaSp1(Cm) | *Cyrtophora moluccensis* MaSp1 | AY666062 | SHLSSPEASSRVSSAVSNLVSSGSTNSAA LPNTISNVVSQISSSNPGLSGCDVLVQAL LEVVSALIHILGSSSIGQVNYGSAGQATQ IV | 4 | 34 |
| MaSp1(Nim) | *Nephila inaurata madagascariensis* MaSp1 | AF350277 | SRLSSPQASSRVSSAVSNLVASGPTNSA ALSSTISNVSQIGASNPGLSGCDVLIQA LLEVVSALIHILGSSSIGQVNYGSAGQAT Q | 4 | 35 |
| MaSp2 (Aam) | *Argiope amoena* MaSp2 | AY365016 | RLSSPQASSRVSSAVSTLVSSGPTNPASL SNAIGSVVSQVSASNPGLPSCDVLVQAL LEIVSALVHILGSSSIGQINYSASSQYARL VGQSIAQALG | 5 | 36 |
| MaSp2(Aau) | *Argiope aurantia* MaSp2 | AF350263 | SRLSSPQASSRVSSAVSTLVSSGPTNPAA LSNAISSVVSQVSASNPGLSGCDVLVQA LLELVSALVHILGSSSIGQINYAAS | 4 | 37 |

TABLE 1-continued

Exemplary spidroin CT domains

| Designation | Species and Spidroin | Genbank accession no | AA sequence | No. charged residues (K/R/E/D) | SEQ ID NO |
|---|---|---|---|---|---|
| MaSp2(At) | *Argiope trifasciata* MaSp2 | AF350267 | SRLSSPQASSRVSSAVSTLVSSGPTNPAS LSNAISSVVSQVSSSNPGLSGCDVLVQA LLEIVSALVHILGSSSIGQINYAASSQYAQ LVGQSLTQALG | 4 | 38 |
| MaSp2(Gm) | *Gasteracantha mammosa* MaSp2 | AF350272 | SRLSSPQAGARVSSAVSALVASGPTSPA AVSSAISNVASQISASNPGLSGCDVLVQ ALLEIVSALVSILSSASIGQINYGASGQYA AMI | 4 | 39 |
| ADF-2 | *Araneus diadematus* fibroin-2 | ADU47854 | SRLSSPSAAARVSSAVSLVSNGGPTSPA ALSSSISNVVSQISASNPGLSGCDILVQAL LEIISALVHILGSANIGPVNSSSAGQSASI VGQSVYRALS | 5 | 40 |
| ADF-3 | *Araneus diadematus* fibroin-3 | ADU47855 | SRLSSPAASSRVSSAVSSLVSSGPTKHAA LSNTISSVVSQVSASNPGLSGCDVLVQA LLEVVSALVSILGSSSIGQINYGASAQYT QMVGQSVAQALA | 4 | 41 |
| MaSp2a | DsMaSp2a [*Deinopis spinosa*] | ABD61593.1 | SAVSRMSTPGSGSRISNAVSNILSSGVSS SSGLSNAISNISSSISASNPGLSGCDVLVQ VLLEVISALVHILGSASVGQVGSSPQNA QMVAANAVANAFS | 4 | 42 |
| MaSp2b | dsMaSp2b [*Deinopis spinosa*] | ABD61594.1 | SAVSRMSTPGSGSRISNAVSNILSSGVSS SSGLSNVISNLSSSISTSNPGLSGCDVLV QVLLEVISALVHILSSASLGQVGSSPQNA QMVAANAVANAFS | 4 | 43 |
| MiSp(Mg) | minor ampullate spidroin [*Metepeira grandiosa*] | ADM14320.1 | GAVNRLSSAEAASRVSSNVAALASGGP AALANVMGNIYSGVASSGVSSGEALVQ ALLEVISALVHLLSNASIGNVSSAGLGNT MSLVCISTVGAYAG | 5 | 44 |
| MiSp(Lh) | minor ampullate spidroin [*Latrodectus hesperus*] | ADM14322.1 | SAASRLSSPSSSSRISSAASSLATGGVLNS AALPSVVSNMMSQVSASSPGMSSSEV VIQALLELVSSLIHILSSANIGQVDFNSVG NTAAVVGQSLGAALG | 5 | 45 |
| MaSp2(Nc) | major ampullate spidroin 2 [*Nephila clavipes*] | AAT75313.1 | AAASRLASPDSGARVASAVSNLVSSGPT SSAALSSVISNAVSQIGASNPGLSGCDVL IQALLEIVSACVTILSSSIGQVNYGAASQ FAQVVGQSVLSAF | 5 | 46 |
| MaSp2(Nim) | major ampullate spidroin 2 [*Nephila inaurata madagascariensis*] | AAK30607.1 | AAASRLASPDSGARVASAVSNLVSSGPT SSAALSSVISNAVSQIGASNPGLSGCDVL IQALLEIVSACVTILSSSIGQVNYGAA | 5 | 47 |
| MiSp-like(Lh) | minor ampullate spidroin 1-like protein [*Latrodectus hesperus*] | ACB29694.1 | SAASRLSSPSSSSRISSAASSLATGGVLNS AALPSVVSNIMSQVSASSPGMSSSEVVI QALLELVSSLIHILSSANIGQVDFNSVGN TAAVVGQSLGAALG | 5 | 48 |
| Consensus | MaSP consensus (SEQ ID NO: 9 in WO2010/123450 | — | SRLSSPQASSRVSSAVSNLVSSGPTNSAA LSNTISNVVSQISASNPGLSGCDVLVQAL LEVVSALVHILGSSSIGQVNYGSAGQAT QIVGQSVAQALGEF | 5 | 49 |
| MaSp1(Mh) | *Macrothele holsti* MaSp1 | AY666068 | SHLSSPEASSRVSSAVSNLVSGGSTNSAA LPNTISNVVSQISSSNPGLSGCDVLVQAL LEVVSALIHILGSSSIGQVDYGSAGQATQ IVGQSA | 5 | 50 |

TABLE 1 -continued

Exemplary spidroin CT domains

| Designation | Species and Spidroin | Genbank accession no | AA sequence | No. charged residues (K/R/E/D) | SEQ ID NO |
|---|---|---|---|---|---|
| MaSp1(Np) | Nephila pilipes MaSp1 | AY666076 | SRLSSPEASSRVSSAVSNLVSSGPTNSAA LSNTISNVVSQISSSNPGLSGCDVLVQAL LEVVSALIHILGSSSIGQVNYGSAGQATQ IV | 5 | 51 |
| MaSp1(Ov) | Octonoba varians MaSp1 | AY666057 | SRLSSPEASSRVSSAVSNLVSSGPTNSAA LSNTISNVVSQISSSNPGLSGCDVLVQAL LEVVSAPIHILGSSSIGQVNYGSAGQATQ IV | 5 | 52 |
| MaSp1(Ps) | Psechrus sinensis MaSp1 | AY666064 | SRLSSPEASSRVSSAVSNLVSSGPTNSAA LPNTISNVVSQISSSNPGLSGCDVLVQAL LEVVSALIHILGSSSIGQVNYGSAGQATQ IV | 5 | 53 |
| MaSp(Tv) | Tetragnatha versicolor MaSp1 | AF350286 | SRLSSPASNARISSAVSALASGGASSPGY LSSIISNVVSQVSSNNDGLSGCDTVVQA LLEVAAALVHVLASSNIGQVNLNTAGYT SQL | 5 | 54 |
| MaSp2(Ns) | Nephila senegalensis MaSp2 | AF350280 | SRLASPDSGARVASAVSNLVSSGPTSSA ALSSVIXNAVSQIGASNPGLSGCDVLIXA LLEIVSACVTILSSSSIGQVNYGAA | 5 | 55 |
| ADF-4 | Araneus diadematus fibroin-4 | ADU47856 | SVYLRLQPRLEVSSAVSSLVSSGPTNGAA VSGALNSLVSQISASNPGLSGCDALVQA LLELVSALVAILSSASIGQVNVSSVSQSTQ MISQALS | 5 | 56 |
| MaSp(Aap) | major ampullate spidroin [Agelenopsis aperta] | AAT08436.1 | NSVSRLSSPSSSSRVSSAVSGLLPNGNFN LGNLPGIVSNLSSSIASSGLSGCENLVQV LIEVVSALVHILGSANIGNINMNAASSTA AAVGQAIVNGLY | 4 | 57 |
| TuSp1(Aar) | tubuliform spidroin 1 [Argiope argentata] | AAY28932.1 | ASSSGLGSSAASARVSSLANSVASAISSS GGSLSVPTFLNFLSSVGAQVSSSSSLNSS EVTNEVLLEAIAALLQVLNGAQITSVNLR NVPNAQQALVQALSG | 5 | 58 |
| CThyb_Esp | Artificial from WO2010/123450 | | SRLSSPEASSRVSSAVSNLVSSGPTNSAA LSSTISNVVSQIGASNPGLSGCDVLVQAL LEVVSALIHILGSSSIGQVNYGSAGQATQ LVGQSVYQALGEF | 6 | 59 |
| MaSp1(Ns) | Nephila senegalensis major ampullate spidroin 1 (MaSp1) | AF350279 | SRLSSPEASSRVSSAVSNLVSSGPTNSAA LSSTISNVVSQIGASNPGLSGCDVLIQAL LEVVSALVHILGSSSIGQVNYGSAGQAT Q | 5 | 60 |
| Fib2(Dt) | Dolomedes tenebrosus Fib2 | AF350270 | SRLSSPQAASRVSSAVSSLVSNGQVNVA ALPSIISSLSSSISASSTAASDCEVLVQVLL EIVSALVQIVSSANVGYINPEASGSLNAV GSALAAAMG | 6 | 61 |
| MiSp(Ud) | MiSp [Uloborus diyersus] | ABD61597.1 | AASNRIVSAPAVNRMSAASSTLVSNGA FNVGALGSTISDMAAQIQAGSQGLSSA EATVQALLEVISVLTHMLSSANIGYVDFS RVGDSASAVSQSMAYAG | 8 | 62 |
| CySp1(Ab) | egg case silk protein 1 [Argiope bruennichi] | BAE86855.1 | VSSSGLGSSAATARVSSLANSFASAISSS GGSLSVPTFLNLLSSVGAQVSSSSSLSSLE VTNEVLLEAIAALLQVINGGSITSVDLRY VPNAQQDLVNALSG | 7 | 63 |
| MiSp(Ay) | minor ampul late spidroin [Araneus yentricosus] | AFV31615.1 | GAVNRLSSAEAASRVSSNIAAIASGGAS ALPSVISNIYSGVVASGVSSNEALIQALLE LLSALVHVLSSASIGNVSSVGVDSTLNVV QDSVGQYVG | 7 | 64 |

TABLE 1 -continued

Exemplary spidroin CT domains

| Designation | Species and Spidroin | Genbank accession no | AA sequence | No. charged residues (K/R/E/D) | SEQ ID NO |
|---|---|---|---|---|---|
| MiSp1(Nc) | minor ampullate silk protein MiSp1 [Nephila clavipes] | AAC14589.1 | STTSRLSSAEASSRISSAASTLVSGGYLNT AALPSVISDLFAQVGASSPGVSDSEVLIQ VLLEIVSSLIHILSSSSVGQVDFSSVGSSA AAVGQSMQVVMG | 8 | 65 |
| Fib1(Dt) | Dolomedes tenebrosus Fib1 | AF350269 | SRLSSPEAASRVSSAVSSLVSNGQVNVD ALPSIISNLSSSISASATTASDCEVLVQVLL EVVSALVQIVCS | 7 | 66 |
| TuSp1(Aap) | tubuliform spidroin 1 [Agelenopsis aperta] | ADM14323.1 | SSETGLSSASASSRVNSLASSVASAIASG QALSADSFAKSLLIQASQIQSSAPSFKAD DVVHESLLEGISALIQVINSSYGSPLSLSN AQTVNAGLVNYFLV | 9 | 67 |
| CySp1(Ncl) | cylindrical silk protein 1 [Nephila clayata] | BAE54450.1 | LSSSGLSSASASARVGSLAQSLASALSTS RGTLSLSTFLNLLSPISSEIRANTSLDGTQ ATVEALLEALAALLQVINGAQITDVNVSS VPSVNAALASALVA | 8 | 68 |
| TuSp1(Lh) | egg case fibroin [Latrodectus hesperus] | ADV40181.1 | LSPAGLASTAATSRINDIAQSLSSTLSSGS QLAPDNVLPGLIQLSSSIQSGNPDLDPA GVLIESLLEYTSALLALLQNAQITTYDAAT LPAFNTALVNYLVPLV | 8 | 69 |
| MiSp(Aar) | minor ampullate spidroin [Argiope argentata] | AFM29836.1 | SVSRLSSAEAVSRVSSNIGAIASGGASAL PGVISNIFSGVSASAGSYEEAVIQSLLEVL SALLHILSNSSIGYVGADGLTDSLAVVQQ AMGPVVG | 8 | 70 |
| MiSp1(Na) | minor ampullate fibroin 1 [Nephila antipodiana] | ABC72645.1 | STTSRLSTAEASSRISTAASTLVSGGYLNT AALPSVIADLFAQVGASSPGVSDSEVLIQ VLLEIVSSLIHILSSSSVGQVDFSSVGSSA AAVGQSMQVVMG | 8 | 71 |
| MiSp(Nc) | minor ampullate silk protein [Nephila clavipes] | AAC14590.1 | STTSRLSSAEACSRISAAASTLVSGSLNTA ALPSVISDLFAQVSASSPGVSGNEVLIQV LLEIVSSLIHILSSSSVGQVDFSSVGSSAA AVGQSMQVVMG | 7 | 72 |
| MiSp(Ds) | Deinopis spinosa MiSp | ABD61589 | ASTSRLASGQATDRVKDVVSTLVSNGIN GDALSNAISNVMTQVNAAVPGLSFCER LIQVLLEIVAALVHILSSSNVGSIDYGSTSR TAIGVSNALASAVAGAF | 11 | 73 |

The CT domain typically consists of from 70 to 120 amino acid residues. It is preferred that the CT domain contains at least 70, or more than 80, preferably more than 90, amino acid residues. It is also preferred that the CT domain contains at most 120, or less than 110 amino acid residues, more preferably less than 100 residues. A typical preferred CT domain contains approximately 87-97 amino acid residues.

Properties of the REP Domain

It is contemplated that the specific sequence or organization of the REP domain is not critical to the present invention as long as the REP-domain is capable of polymerization, and that a wide variety of spider silk REP-domains would be suitable for the present protein. In Rising et al. (Cell. Mol. Life Sci. (2011) 68:169-184), several REP-domains used in the art in recombinant spidroins are discussed, and it is contemplated that a REP-domain based on teachings therein would be useful in the present context.

In general terms, the REP domain has a repetitive character, preferably alternating between alanine-rich stretches (A-segments) and glycine-rich stretches (G-segments).

The REP domain of the present invention may comprise alanine-rich A-segments and glycine-rich G-segments, wherein the sum of the number of A segments and the number of G segments in the REP-domain is 3 to 30, preferably 4-20, more preferably 4-10, most preferably 4-8.

The REP domain may comprise alanine-rich A-segments and glycine-rich G-segments, wherein each A segment is an amino acid sequence of from 8 to 20 amino acid residues, wherein at least 60%, preferably at least 65%, more preferably at least 70%, most preferably at least 75% of the amino acid residues are Ala.

The REP domain may comprise alanine-rich A-segments and glycine-rich G-segments, wherein each G segment is an amino acid sequence of from 12 to 40 amino acid residues, wherein at least 30%, preferably at least 35%, most preferably at least 40% of the amino acid residues are Gly.

The REP domain may comprise alanine-rich A-segments and glycine-rich G-segments, wherein each A segment contains at least one stretch of 5 consecutive, preferably 6 consecutive A residues. The REP domain may comprise alanine-rich A-segments and glycine-rich G-segments, wherein each G segment contains at least one, preferably at least two GGX motif(s), where X designates any amino acid.

The REP-domain may comprise 40-600, preferably 50-500, more preferably 60-400, most preferably 70-300 amino acids.

The REP domain generally contains more than 30, such as more than 70, and less than 600, preferably less than 300, such as less than 240, amino acid residues, and can itself be divided into several L (linker) segments, A (alanine-rich) segments and G (glycine-rich) segments, as will be explained in more detail below. Typically, said linker segments, which are optional, are located at the REP domain terminals, while the remaining segments are in turn alanine-rich and glycine-rich. Thus, the REP domain can generally have either of the following structures, wherein n is an integer:

$L(AG)_nL$, such as $LA_1G_1A_2G_2A_3G_3A_4G_4A_5G_5L$;
$L(AG)_nAL$, such as $LA_1G_1A_2G_2A_3G_3A_4G_4A_5G_5A_6L$;
$L(GA)_nL$, such as $LG_1A_1G_2A_2G_3A_3G_4A_4G_5A_5L$; or
$L(GA)_nGL$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, preferably from 4 to 8, more preferred from 4 to 6, i.e. n=4, n=5 or n=6.

The alanine content of the REP domain according to the invention may be above 20%, preferably above 25%, more preferably above 30%, and below 50%, preferably below 40%, more preferably below 35%. This is advantageous, since it is contemplated that a higher alanine content provides a stiffer and/or stronger and/or less extendible fiber.

The REP domain is preferably void of proline residues, i.e. there are no Pro residues in the REP domain.

Now turning to the segments that constitute the REP domain according to the invention, it shall be emphasized that each segment is individual, i.e. any two A segments, any two G segments or any two L segments of a specific REP domain may be identical or may not be identical. Thus, it is not a general feature of the invention that each type of segment is identical within a specific REP domain. Rather, the following disclosure provides the skilled person with guidelines how to design individual segments and gather them into a REP domain, which is a part of a functional spider silk protein according to the invention.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

Each A segment may contain 13-15 amino acid residues, including 10-15 alanine residues and 0-3 non-alanine residues as described above. More preferably, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 3. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO: 3. Each sequence of this group corresponds to a segment of expressed, non-natural spider silk proteins according to the invention, which proteins have capacity to form silk fibers under appropriate conditions. Thus, in certain embodiments according to the invention, each individual A segment is identical to an amino acid sequence selected from the above-mentioned amino acid segments. Without wishing to be bound by any particular theory, it is envisaged that A segments according to the invention form helical structures or beta sheets.

Throughout this description, alternative embodiments according to the invention fulfil, instead of the specified percentage of identity, the corresponding percentage of similarity.

Other alternative embodiments fulfil the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically, the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 3. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO: 3. Each sequence of this group corresponds to a segment of expressed, non-natural spider silk proteins according to the invention, which proteins have capacity to form silk fibers under appropriate conditions. Thus, each individual G segment may preferably be identical to an amino acid sequence selected from the above-mentioned amino acid segments.

The first two amino acid residues of each G segment according to the invention are preferably not -Gln-Gln-.

There are the three subtypes of the G segment according to the invention. This classification is based upon careful analysis of the *Euprosthenops australis* MaSp1 protein sequence (WO 2007/078239), and the information has been employed and verified in the construction of non-natural spider silk proteins.

The first subtype of the G segment according to the invention is represented by the amino acid one letter consensus sequence GQG(G/S)QGG(Q/Y)GG (L/Q)GQG-GYGQGA GSS (SEQ ID NO: 4). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 3. The first two amino acid residues of each G segment of this first subtype according to the invention are preferably not -Gln-Gln-.

The second subtype of the G segment according to the invention is represented by the amino acid one letter consensus sequence GQGGQGQG(G/R)Y GQG(A/S)G(S/G)S (SEQ ID NO: 5). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 3; and amino acid residues 187-203 of SEQ ID NO: 3.

The third subtype of the G segment according to the invention is represented by the amino acid one letter consensus sequence G(R/Q)GQG(G/R)YGQG (A/S/V)GGN (SEQ ID NO: 6). This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 3; and amino acid residues 219-232 of SEQ ID NO: 3.

Thus, each individual G segment preferably has at least 80%, more preferably 90%, yet more preferably 95%, most preferably 100% identity to an amino acid sequence selected from SEQ ID NO: 4, SEQ ID NO: 5 and SEQ ID NO: 6.

It is preferred that the alternating sequence of A and G segments of the REP domain, every second G segment is of the first subtype, while the remaining G segments are of the third subtype, e.g. $A_1G_{short}A_2G_{long}A_3G_{short}A_4G_{long}A_5G_{short}$ . . . .

Alternatively, it is preferred that the REP domain, one G segment of the second subtype interrupts the G segment regularity via an insertion, e.g. $A_1G_{short}A_2G_{long}A_3G_{mid}A_4G_{short}A_5G_{long}$ . . . .

Each individual L segment represents an optional linker amino acid sequence, which may contain from 0 to 30 amino acid residues, preferably 0-25 amino-acid residues, such as from 0 to 10 amino acid residues. While this segment is optional and not functionally critical for the spider silk protein, its presence still allows for fully functional spider silk proteins, forming spider silk fibers according to the invention. There are also linker amino acid sequences present in the repetitive part (SEQ ID NO: 3) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP domain can be represented by the amino acid one letter consensus sequences ASASAAASAASTVANSVS (SEQ ID NO: 7) and ASAASAAA (SEQ ID NO: 8), which are rich in alanine. In fact, the second sequence can be considered to be an A segment according to the invention, while the first sequence has a high degree of similarity to A segments according to the invention. Another example of a linker segment according the invention has the one letter amino acid sequence GSAMGQGS (SEQ ID NO: 9), which is rich in glycine and has a high degree of similarity to G segments according to the invention. Another example of a linker segment is SASAG (SEQ ID NO: 10). Yet further example of a linker segment is VTSGGYGYGTSAAAGAGVAAGSYA (part of SEQ ID NO: 11) derived from *A. ventricosus* MiSP CT protein, see Example 1.

Representative L segments are amino acid residues 1-6 and 1093-1110 of SEQ ID NO: 3; and amino acid residues 138-142 of SEQ ID NO: 3, but the skilled person in the art will readily recognize that there are many suitable alternative amino acid sequences for these segments. In the REP domain according to the invention, one of the L segments may contain 0 amino acids, i.e. one of the L segments is void. In the REP domain according to the invention, both L segments may contain 0 amino acids, i.e. both L segments are void. Thus, these embodiments of the REP domains according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP domains are suitable for use with any CT domain as defined above.

It is preferable that n is 2 or 4. The selected REP domain is preferably $LG(AG)_2L$ or $LG(AG)_4L$. Most preferably, the selected REP domain is $LG(AG)_2L$.

The spider silk protein may comprise a set of domains according to the formula NTL-REP-L-CT, wherein each individual L segment is a linker amino acid sequence of from 1 to 30, preferably 1-25 amino acid residues.

It is preferable that the REP domain consists of a sequence of 30-600, more preferably 50-500, most preferably 70 to 300 amino acid residues.

Properties of the Optional NT Domain

It is preferable that the optional NT domain is present. Needless to say, the following definitions of NT are only relevant in situations where the NT domain is actually present.

The NT domain has a high degree of similarity to the N-terminal amino acid sequence of spider silk proteins. As shown in FIG. 1, this amino acid sequence is well conserved among various species and spider silk proteins, including MaSp1 and MaSp2. In FIG. 1, the following spidroin NT domains are aligned, denoted with GenBank accession entries where applicable:

TABLE 2

Exemplary spidroin NT domains

| Designation | Species and spidroin protein | GenBank acc. no. | SEQ ID NO: |
| --- | --- | --- | --- |
| Ea MaSp1 | *Euprosthenops australis* MaSp 1 | AM259067 | 80 |
| Lg MaSp1 | *Latrodectus geometricus* MaSp 1 | ABY67420 | 81 |
| Lh MaSp1 | *Latrodectus hesperus* MaSp 1 | ABY67414 | 82 |
| Nc MaSp1 | *Nephila clavipes* MaSp 1 | ACF19411 | 83 |
| At MaSp2 | *Argiope trifasciata* MaSp 2 | AAZ15371 | 84 |
| Lg MaSp2 | *Latrodectus geometricus* MaSp 2 | ABY67417 | 85 |
| Lh MaSp2 | *Latrodectus hesperus* MaSp 2 | ABR68855 | 86 |
| Nim MaSp2 | *Nephila inaurata madagascariensis* MaSp 2 | AAZ15322 | 87 |
| Nc MaSp2 | *Nephila clavipes* MaSp 2 | ACF19413 | 88 |
| Ab CySp1 | *Argiope bruennichi* cylindriform spidroin 1 | BAE86855 | 89 |
| Ncl CySp1 | *Nephila clavata* cylindriform spidroin 1 | BAE54451 | 90 |
| Lh TuSp1 | *Latrodectus hesperus* tubuliform spidroin | ABD24296 | 91 |
| Nc Flag | *Nephila clavipes* flagelliform silk protein | AF027972 | 92 |
| Nim Flag | *Nephila inaurata madagascariensis* flagelliform silk protein | AF218623 (translated) | 93 |

Only the part corresponding to the N-terminal fragment is shown for each sequence, omitting the signal peptide. Nc flag and Nlm flag are translated and edited according to Rising A. et al. Biomacromolecules 7, 3120-3124 (2006)).

It is not critical which specific NT domain is present in spider silk proteins according to the invention. Thus, the NT domain according to the invention can be selected from any of the amino acid sequences shown in Table 2 or sequences with a high degree of similarity. A wide variety of N-terminal sequences can be used in the spider silk protein according to the invention. Based on the homologous sequences of FIG. 1, the following sequence constitutes a consensus NT amino acid sequence:

(SEQ ID NO: 2)
QANTPWSSPNLADAFINSF(M/L)SA(A/I)SSSGAFSADQLDDMSTIG (D/N/Q)TLMSAMD(N/S/K)MGRSG(K/R)STKSKLQALNMAFASSMA

EIAAAESGG(G/Q)SVGVKTNAISDALSSAFYQTTGSVNPQFV(N/S)

EIRSLI(G/N)M(F/L)(A/S)QASANEV.

The sequence of the NT domain according to the invention may have at least 50% identity, preferably at least 60% identity, to the consensus amino acid sequence SEQ ID NO: 2, which is based on the amino acid sequences of FIG. 1. Preferably, the sequence of the NT domain according to the invention has at least 65% identity, more preferably at least 70% identity, to the consensus amino acid sequence SEQ ID NO: 2. More preferably, the NT domain according to the invention has furthermore 70%, most preferably 80%, similarity to the consensus amino acid sequence SEQ ID NO: 2.

A representative NT domain according to the invention is the *Euprosthenops australis* sequence SEQ ID NO: 1. Preferably, the NT domain has at least 80% identity to SEQ ID NO: 1 or any individual amino acid sequence in Table 2. More preferably, the NT domain has at least 90%, such as at least 95% identity, to SEQ ID NO: 1 or any individual amino acid sequence in Table 2. Most preferably, the NT domain is identical to SEQ ID NO: 1 or any individual amino acid sequence in Table 2, in particular to Ea MaSp1.

The NT domain contains from 100 to 160 amino acid residues. It is preferred that the NT domain contains at least 100, or more than 110, preferably more than 120, amino acid residues. It is also preferred that the NT domain contains at most 160, or less than 140 amino acid residues. A most preferred NT domain contains approximately 130-140 amino acid residues.

When the N-terminal part of the spider silk protein contains two or more domains (NT) derived from the N-terminal domain of a spider silk protein, it may also contain one or more linker peptides. The linker peptide(s) may be arranged between two NT domains and provide a spacer.

Properties and Features of the Chimeric Spider Silk Protein

Preferably, the recombinant spider silk protein exhibits highly pH-dependent solubility, more preferably highly pH-dependent solubility defined as least 10 times, preferably 50 times, more preferably 100 times higher solubility in aqueous 20 mM Tris-HCl pH8.0 buffer than in aqueous 500 mM Na-acetate, 200 mM NaCl at pH5.0.

Preferably, the recombinant spider silk protein is soluble in aqueous 20 mM Tris-HCl pH8.0 buffer at a concentration of 100 mg/ml, more preferably 200 mg/ml, most preferably 300 mg/ml, and polymerizes in aqueous 500 mM Na-acetate, 200 mM NaCl at pH5.0.

Preferably, the protein according to the first aspect comprises a sequence having at least 80%, preferably at least 85%, more preferably at least 90%, yet more preferably at least 95% sequence identity to SEQ ID NO: 11. Most preferably, the recombinant spider silk protein of the first aspect consists of a sequence identical to SEQ ID NO: 11.

Preferably, the spider silk protein comprises no more than 600, preferably no more than 500, more preferably no more than 400, yet more preferably no more than 300, most preferably no more than 250 amino-acid residues in total. Smaller proteins are generally easier to produce recombinantly in high quantities.

Solutions of Chimeric Spider Silk Proteins

In a second aspect of the present invention, there is provided a non-denaturing solution of a spider silk protein according to any of the preceding claims, having a protein concentration of said spider silk protein of at least 100 mg/ml, preferably 150 mg/ml, most preferably 200 mg/ml. Needless to say, the non-denaturing solvent has a composition that does not lead to polymerization of said protein, notably with regards to pH, salt concentration and organic solvents. For instance, the solvent may be aqueous 20 mM Tris-HCl pH 8.0 buffer or the like. Preferably, the pH is 6.4 or above, such at 7.0 or above, preferably 7.5-8.5.

Polymers of Chimeric Spider Silk Proteins

In a third aspect, there is provided a polymer of a spider silk protein according to the first aspect. Said polymer may e.g. be a fiber, film, foam, net or mesh, preferably a fiber.

Said polymer may be a fiber having length of at least 10 cm, preferably at least 1 m, more preferably at least 5 m, yet more preferably at least 10 m, still more preferably at least 50 m, most preferably at least 100 m.

The diameter of the fiber may be 100 µm, preferably less than 50 µm, more preferably less than 20 µm, most preferably less than 10 µm.

The polymer may have toughness of $\geq 3$ MJ/m$^3$, preferably $\geq 10$ MJ/m$^3$, more preferably $\geq 20$ MJ/m$^3$, most preferably $\geq 40$ MJ/m$^3$. Preferably, the toughness refers to polymer that is as-spun. i.e. not subjected to post-stretching or similar after-treatment.

Methods for Producing a Polymer of Spider Silk Protein

In a fourth aspect, there is provided a method for producing a polymer of a spider silk protein, comprising the steps of:
 a. providing a first liquid medium comprising a spider silk protein according to the first aspect in solution in said medium at a concentration of at least 100 mg/ml, preferably 200 mg/ml, most preferably 300 mg/ml;
 b. adjusting the properties of the first liquid medium such that it allows polymerisation of said spider silk protein;
 c. allowing the spider silk protein to form polymers; and
 d. isolating the spider silk protein polymers.

The properties of the first liquid medium may be adjusted by extruding the solution of a spider silk protein into a second fluid medium having properties that allow polymerisation of said spider silk protein.

The first liquid medium in step (a) preferably has a pH of at least 6.4.

The first liquid medium in step (a) preferably has a salt concentration of less than 100 mM.

The first liquid medium in step (a) is preferably an aqueous solution comprising less than 10% (v/v) of organic solvents.

The properties of the first liquid medium in steps (b)-(d) are preferably adjusted to pH 6.3 or below, in the presence of a sufficient salt concentration for polymerisation of said spider silk protein.

The properties of the first liquid medium in steps (b)-(d) may be adjusted to at least 100 mM salt concentration and to pH 6.3 or below.

The properties of the first liquid medium in steps (b)-(d) may be adjusted to having a concentration of an organic solvent sufficient to induce polymerization.

The second fluid medium may have pH 6.3 or below, and a sufficient salt concentration for polymerisation of said spider silk protein.

The second fluid medium may comprise an organic solvent at a concentration sufficient to induce polymerization.

The second fluid medium may comprise a hygroscopic polymer, such as PEG.

The extrusion may be through a capillary having an opening with a cross-sectional area in the interval 20-50000 µm$^2$, preferably 30-30000 µm$^2$, more preferably 40-10000 µm$^2$, yet more preferably 50-5000 µm$^2$, most preferably 70-800 µm$^2$.

The extrusion may be performed at a linear flow rate of 0.1-500 mm/s, more preferably 0.5-200 mm/s, most preferably 1-100 mm/s.

Preferably, the polymer is extruded in a 3D-printing apparatus to enable formation of a defined pattern.

Said polymer may form a fiber, film, foam, net or mesh, preferably a fiber.

The polymers may also be subjected to further treatments, for instance post-stretching in different aqueous buffers and/or alcohol baths, and/or dehydrating solutions such as polyethylene glycol (PEG).

DNA Sequences, Constructs, Host Cells, Methods of Manufacture

In a fifth aspect, there is provided a nucleic acid encoding for a protein according the first aspect.

In a sixth aspect, there is provided an expression vector comprising a nucleic acid according to the fifth aspect, operatively coupled to a promoter.

In a seventh aspect, there is provided a host cell comprising a nucleic acid according to the fifth aspect, or an expression vector according to the sixth aspect.

In an eighth aspect, there is provided a method of producing a recombinant spider silk protein, comprising:
 a. Culturing a host cell according to the seventh aspect, in conditions allowing production of the protein;
 b. Isolating said protein from said culture.

The spider silk protein according to the invention is typically recombinantly produced using a variety of suitable hosts, such as bacteria, yeast, mammalian cells, plants, insect cells, and transgenic animals. It is preferred that the spider silk protein according to the invention is produced in bacteria.

Uses of Spider Silk Protein

The recombinant spider silk protein and the polymers derived thereof discussed above are useful for any of the known applications for spider silk proteins.

In a ninth aspect, there is provided a use of a spider silk protein according to the first aspect, or a polymer according to the third aspect, in the manufacture of an implantable material or a cell culture scaffold.

In a tenth aspect, there is provided a use of a spider silk protein according to the first aspect, or a polymer according to the third aspect, as an implantable material or a cell culture scaffold.

General Aspects Relevant to Present Disclosure

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

The following examples are not to be regarded as limiting. For further information on the experimental details, the skilled reader is directed to a separate section titled Materials and Methods.

Example 1: Production of a Chimeric Minispidroin NT2RepCT

Figure 2:
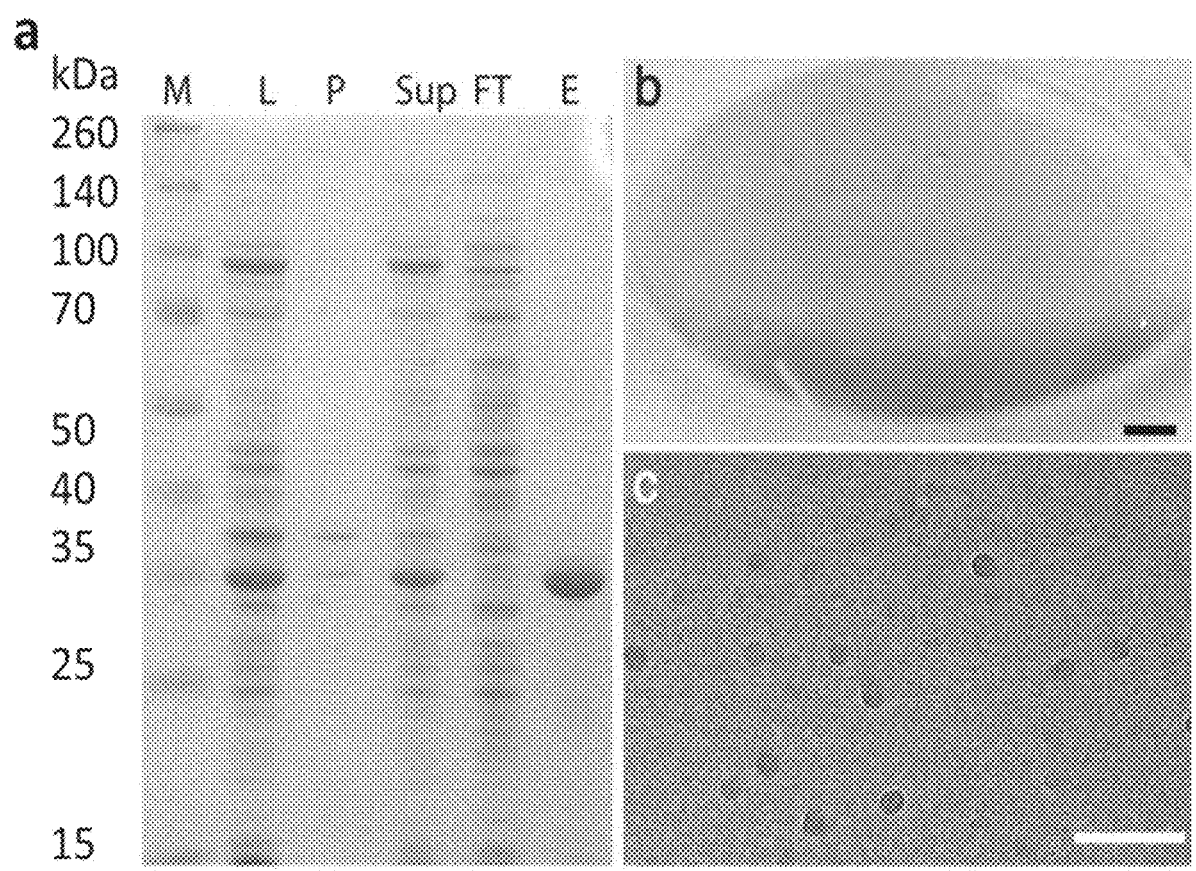
FIG. 2: NT2RepCT has a high expression level and aqueous solubility. (a) SDS-PAGE of purified NT2RepCT and different purification steps. M=Spectra Broadrange protein marker (sizes in kilodalton is shown to the left), L=total cell lysate, P=pellet, Sup=supernatant after centrifugation of whole cell lysate, FT=flow through Ni-NTA column, E=target protein NT2RepCT eluted from the Ni-NTA column. (b) Photograph of gel of NT2RepCT, formed at 300 mg/ml protein concentration. Scale bar 0.1 cm. (c) Cryo-EM of NT2RepCT at 0.001 mg/ml. Scale bar 50 nm.
Figure 6:
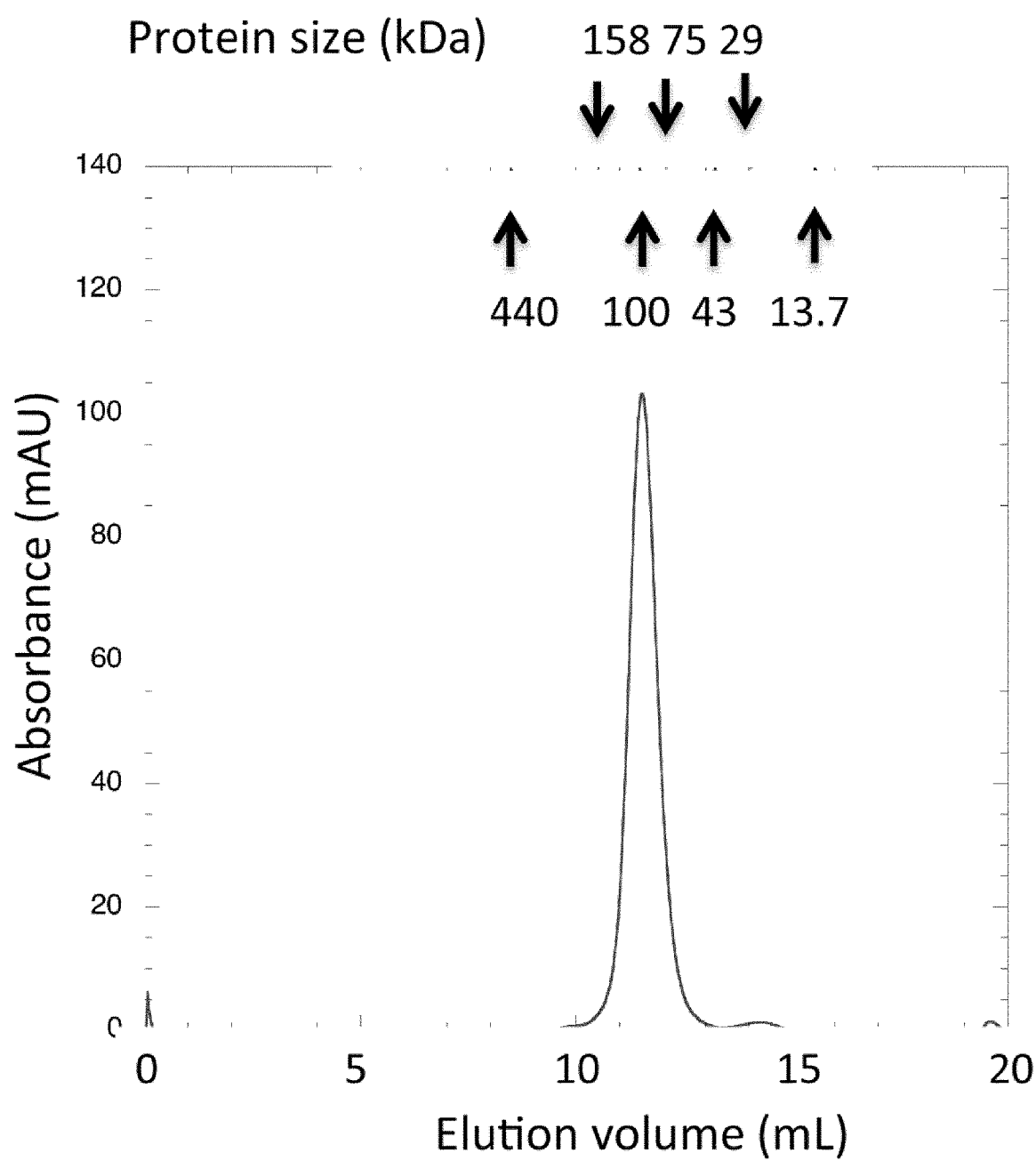
FIG. 6: Size exclusion chromatography of NT2RepCT. The protein sizes above the chromatogram are derived from calibrant proteins.

The inventors designed a minispidroin composed of NT from *E. australis* MaSp1 and CT from *A. ventricosus* MiSp bracketing a short repetitive region from *E. australis*. The chimeric NT2RepCT protein was produced at unprecedented high levels in shake flask *E. coli* cultures and the yield after purification was around 125 mg protein/L cell culture. Nearly all protein was soluble after expression and lysis, and bound efficiently to the Ni-NTA column (FIG. 2A). The eluate contained >95% pure NT2RepCT and the size of the protein on the SDS PAGE gel corresponded well to the expected molecular mass (33 kDa) (FIG. 2A). Size-exclusion chromatography indicated a mass of 100 kDa (FIG. 6), in good agreement with a dimer (due to the constitutive dimeric nature of CT) and a non-globular structure of the repetitive part.

Example 2: Chimeric Minispidroin NT2RepCT Exhibits Extreme Solubility

Figure 7:
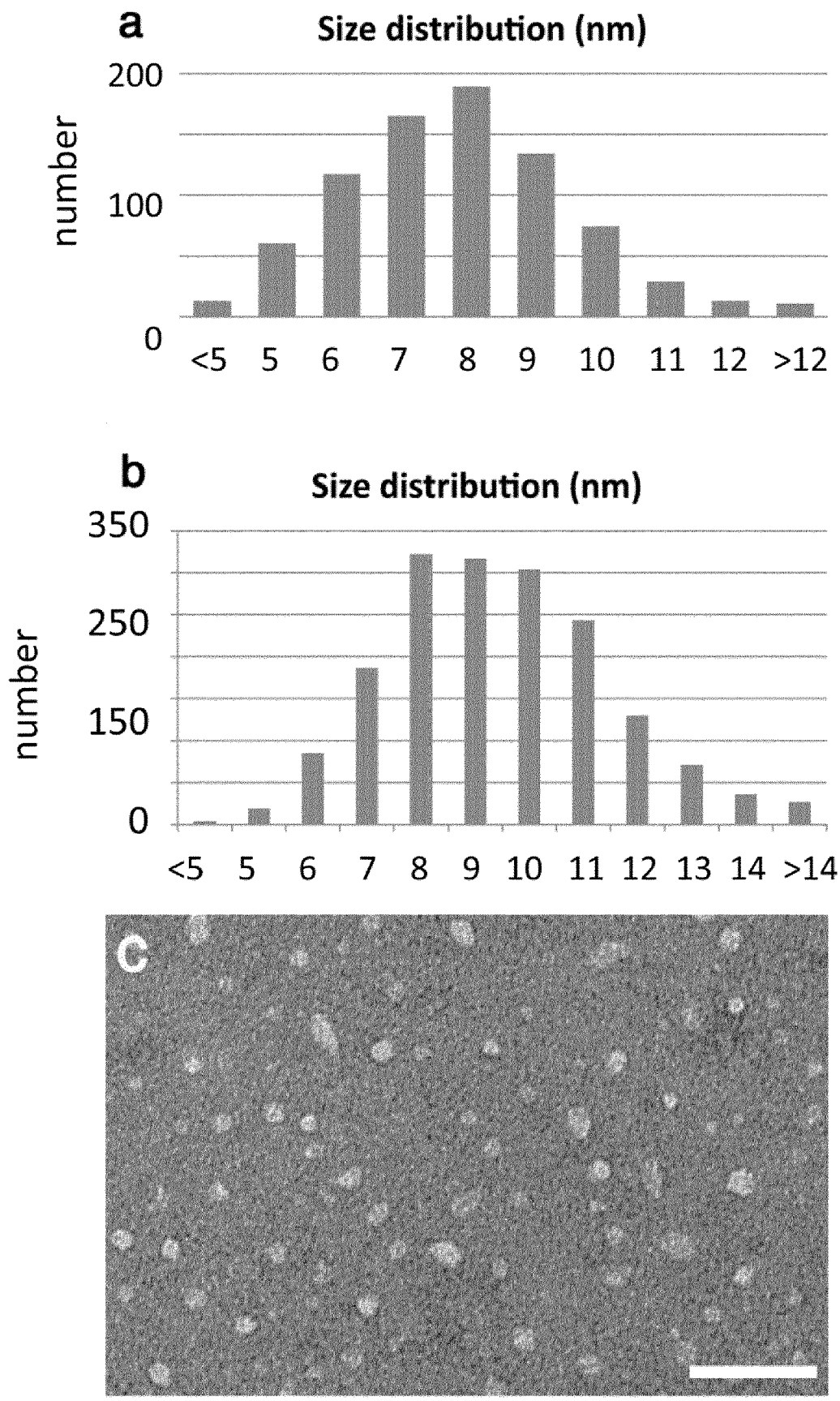
FIG. 7: NT2RepCT micelles studied by electron microscopy. a) Size distribution of micelles using transmission electron microscopy with negative stain. b) Size distribution of micelles using cryo-electron microscopy. c) Transmission electron micrograph of micelles with negative stain. Scale bar 50 nm.

Obtaining spinning dopes of high concentration in water has been a long-standing major goal, but to date, the reported concentrations of artificial spinning dopes have been in the range of 10-30%, even though non-physiological solvents have been used. NT2RepCT of Example 1 far surpassed all expectations in terms of solubility; it could be concentrated to 500 mg/ml in aqueous buffer at pH 8 without precipitation, which equals or even exceeds the protein concentration in the spinning dope of the spider. At such high concentrations, the protein formed a yellow hydrogel (FIG. 2B). Native spider silk dope has been showed to be stored as micelles, 100-200 nm in diameter, probably with the terminal domains in the shell and the repetitive regions shielded in the core. This has also been proposed to be the storage mechanism in silkworm silk glands. The NT2RepCT protein behaves as native silk proteins in this respect and assembles into ~10 nm micelles (FIG. 2C, FIG. 7). The smaller diameter of the micelles composed of recombinant spidroin compared to the micelles in native spider silk dope is expected from the short repetitive region of NT2RepCT. NT2RepCT at 500 mg/ml could be stored at 4° C. for weeks and at −20° C. for months with maintained ability to form fibers (c.f. below). This is surprising, since the reported typical stability of artificial spinning dope solutions is 3-5 days.

Published purification protocols have involved precipitation of the expressed protein with ammonium sulfate, lyophilization, followed by solubilization in HFIP or guanidinium-thiocyanate. The presence of non-aqueous solvents or other denaturants during production will likely prevent formation of native structures and we propose that the high solubility and stability over time of NT2RepCT is related to the presence of natively folded NT and CT, a supposition that is supported by the observation of native-like micellar structures. Moreover, Fourier transform infrared (FTIR) spectroscopy of NT2RepCT protein in solution showed amide I and II band maxima approximately at wavenumber 1545 and 1650 cm$^{-1}$, respectively (FIG. 9), which indicates an alpha helical structure. This is in good agreement with the native five-helix bundle structures of both NT and CT.

Example 3: Biomimetic Spinning of the NT2RepCT Minispidroin

Figure 3:
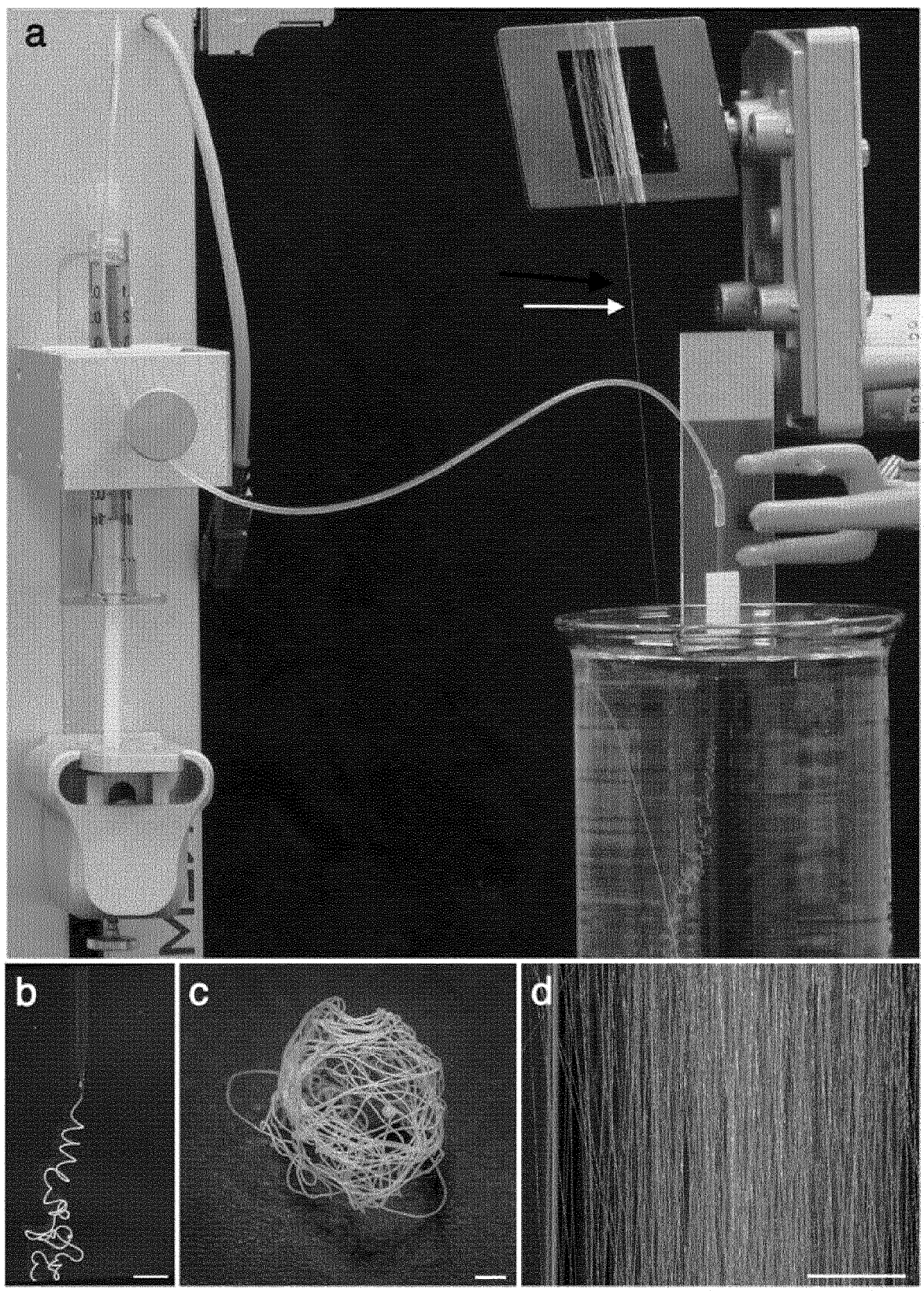
FIG. 3. Biomimetic spinning of artificial spider silk. (a) Highly concentrated NT2RepCT spinning dope in a syringe is pumped through a pulled glass capillary with a tip size of 10-30 µm, with the tip submerged into a low pH aqueous collection bath. Fibers can be pulled up (arrow) from the collection bath and rolled up onto frames. (b) Photo of the fiber as it is spun in the low pH aqueous collection bath. (c) Wet fiber nest in low pH buffer. (d) Fibers rolled up onto a frame. Fiber diameter in b-c approximately 40 µm. Fiber diameter in d 15 µm. Scale bar in (b) 3 mm (c-d) 5 mm.
Figure 8:
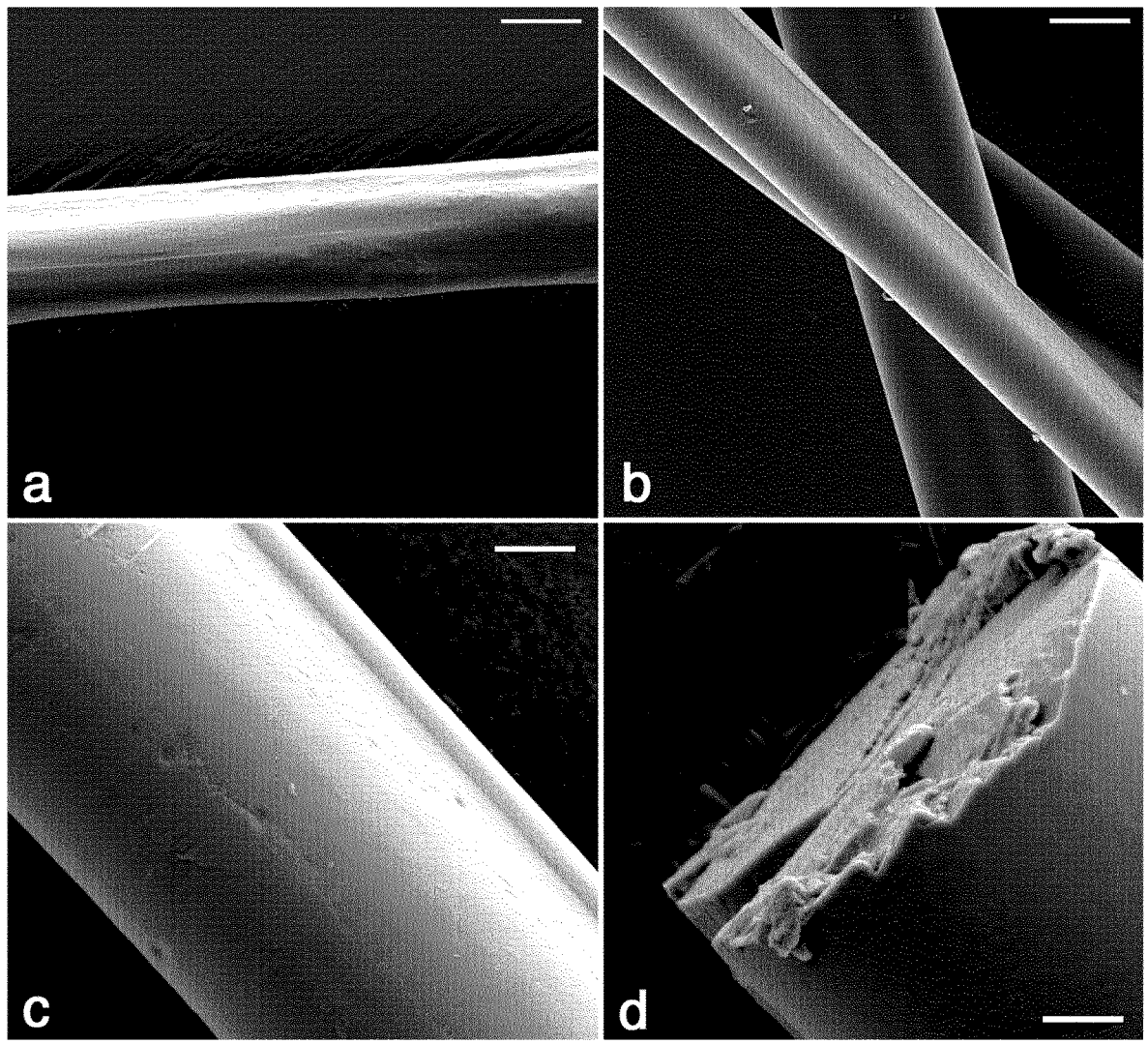
FIG. 8: Scanning electron micrographs of NT2RepCT fibres. (A) As-spun fibre. (B) As-spun fibres collected on a frame. (C) Fibre post-stretched 200% in 500 mM sodium acetate buffer and 200 mM NaCl (pH 5). (D) Fracture surface of a post-stretched fibre to examine the fibre interior core. All fibres were spun in a collection bath with 500 mM sodium acetate buffer and 200 mM NaCl (pH 5). Scale bars are (A-B) 10 µm (C-D) 2 µm.

Another prerequisite that needs to be fulfilled in order to achieve biomimetic spinning is to engineer a spinning device that can mimic the conditions of the spider silk gland. We designed a first-generation simple but efficient spinning device from a thin pulled glass capillary through which the highly-concentrated NT2RepCT dope is pumped into an acidic aqueous buffer collection bath (FIG. 3). This setup generates a drop in pH and allows shear forces to act on the dope as it travels through the tip of the capillary, and results in formation of a continuous solid fiber (FIG. 3A-B). Fibers could easily be reeled onto rotating frames in air at lengths exceeding hundreds of meters (FIG. 3C). The dope concentration interval at which fibers could be spun ranged from 100 to 500 mg/ml. Fibers spun from dopes with concentrations >200 mg/ml were more easily handled and could be spun into a continuous fiber without breaking. As-spun fibers were homogenous as judged by SEM with a diameter of approximately 10-20 μm (FIG. 8). Fibers post-stretched in a low pH bath had slightly decreased diameters compared to as-spun fibers. The fracture surfaces from fibers that were pulled until failure show a compact and homogenous interior core (FIG. 8).

Figure 9:
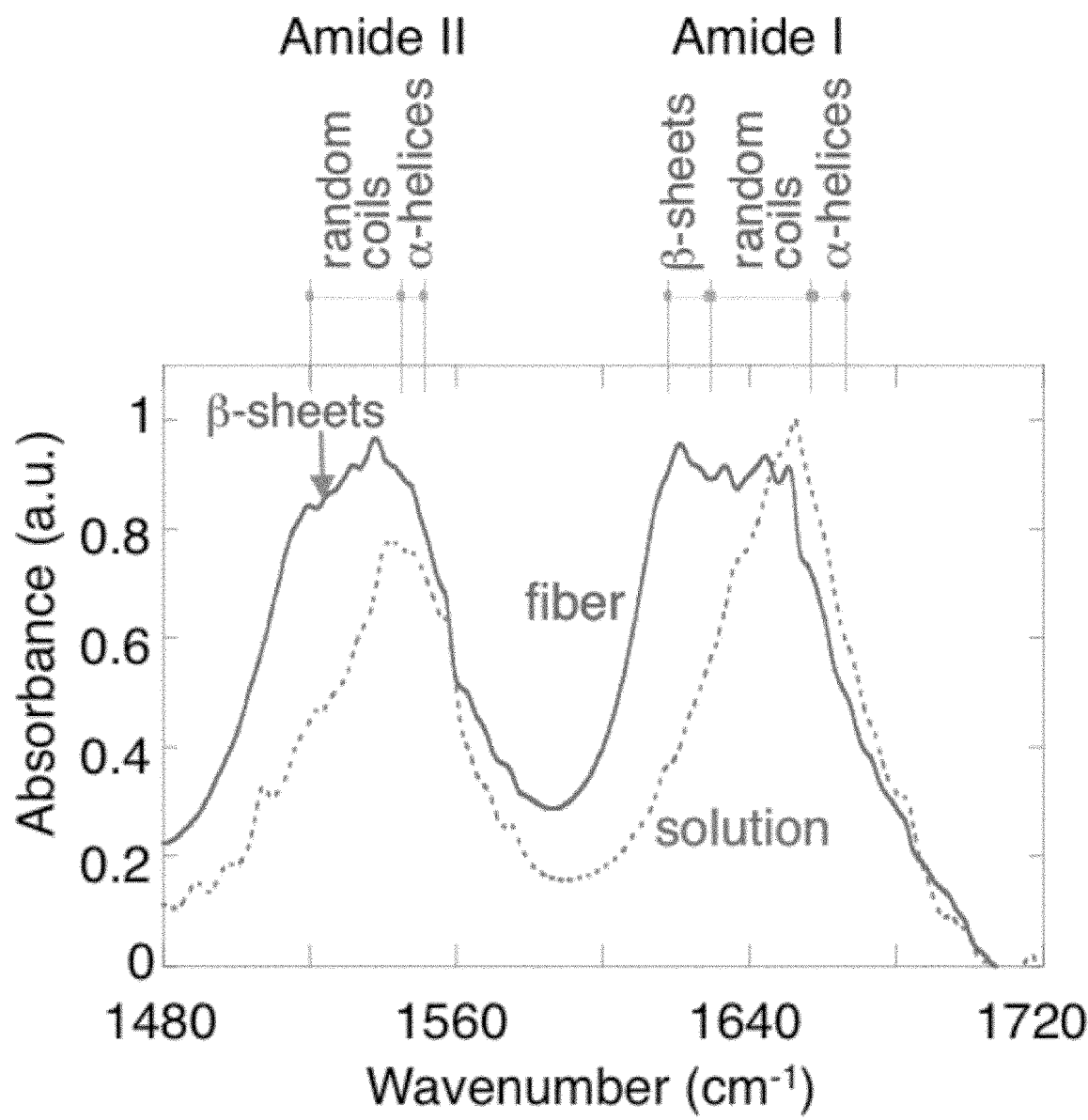
FIG. 9: Fourier Transform Infrared Spectroscopy of NT2RepCT. FTIR spectra of NT2RepCT protein in solution (dotted line) and NT2RepCT fibres (solid line).

Fourier transform infrared spectroscopy (FTIR) analysis of NT2RepCT fibers showed an increase in β-sheet conformation compared to the soluble state, as can be seen by the shift in the amide I and II peak distributions (FIG. 9).

Example 4: Effect of pH on Fiber Spinning

Figure 4:
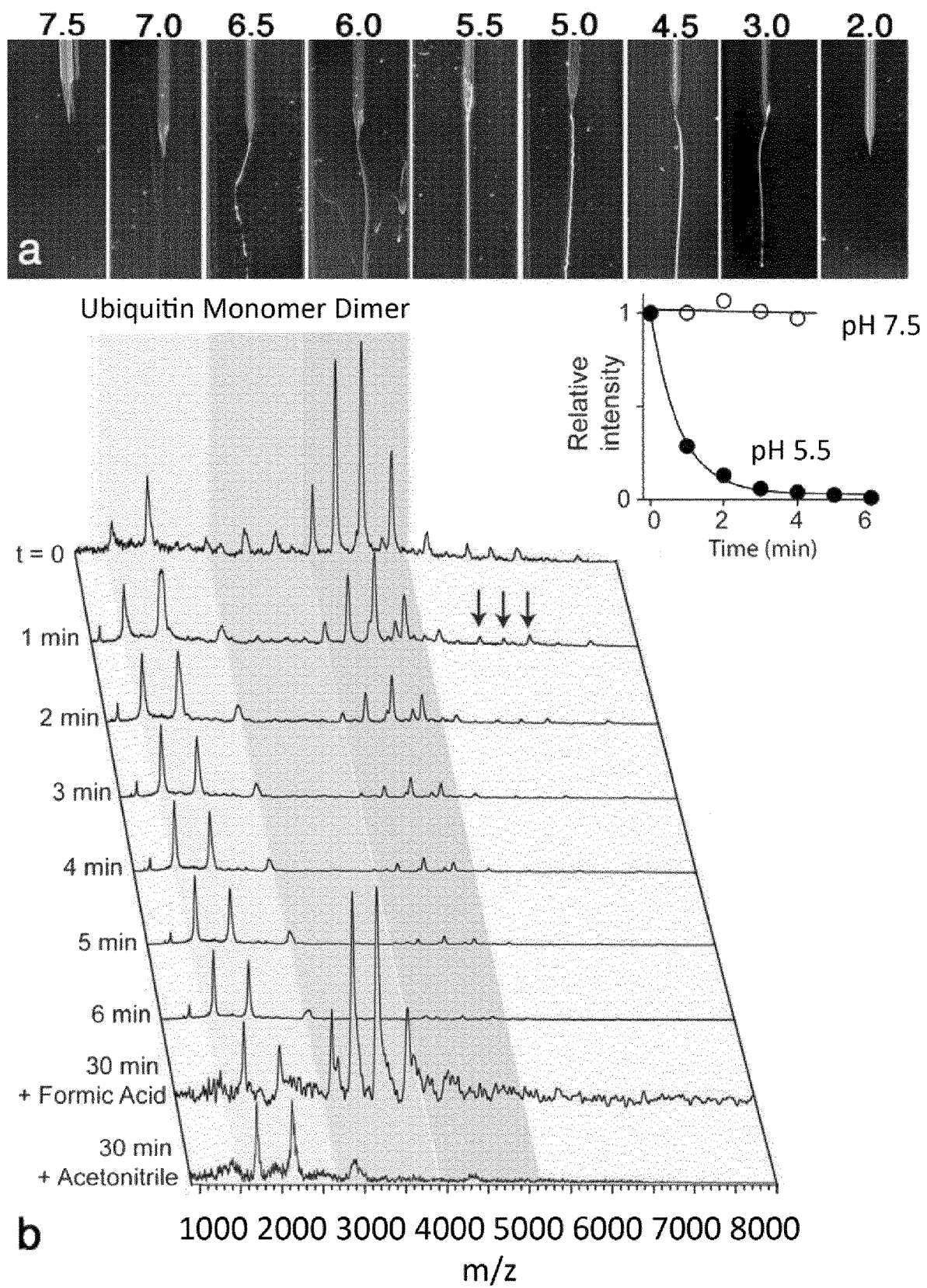
FIG. 4. Characterization of NT2RepCT fibers. (a) Spinning into buffers at different pH values. Continuous fibers that can be pulled up and rolled onto a frame are formed in buffers with 3.0≤pH≤5.5. (b) nESI-MS time-course of NT2RepCT incubated at pH 5.5. Prolonged exposure to low pH induces aggregation of NT2RepCT. Addition of concentrated formic acid to the aggregates releases monomers, but addition of acetonitrile does not. Ubiquitin was used as internal standard to follow the time-dependent signal decrease for the residual NT2RepCT dimer. (c) At pH 7.5, a stable population of native dimers can be detected (open symbols), while incubation at pH 5.5 leads to complete loss of soluble NT2RepCT over the course of a few minutes (Filled symbols).

To further investigate the effect of pH on fiber spinning, the dope was extruded into aqueous baths with pH ranging from 2.0 to 7.5. Discontinuous fiber-like structures were formed when pH of the bath was between 6.0-6.5 (FIG. 4A). Continuous fibers were formed when pH was between 3.0 and 5.5 (FIG. 4A) and the fibers were easily pulled from collection baths and could be reeled onto frames (FIGS. 3 and 4). If the pH of the collection bath was ≤2.5 no fibers could be seen (FIG. 4A).

Example 5: Assembly of NT2RepCT on a Molecular Level

Figure 10:
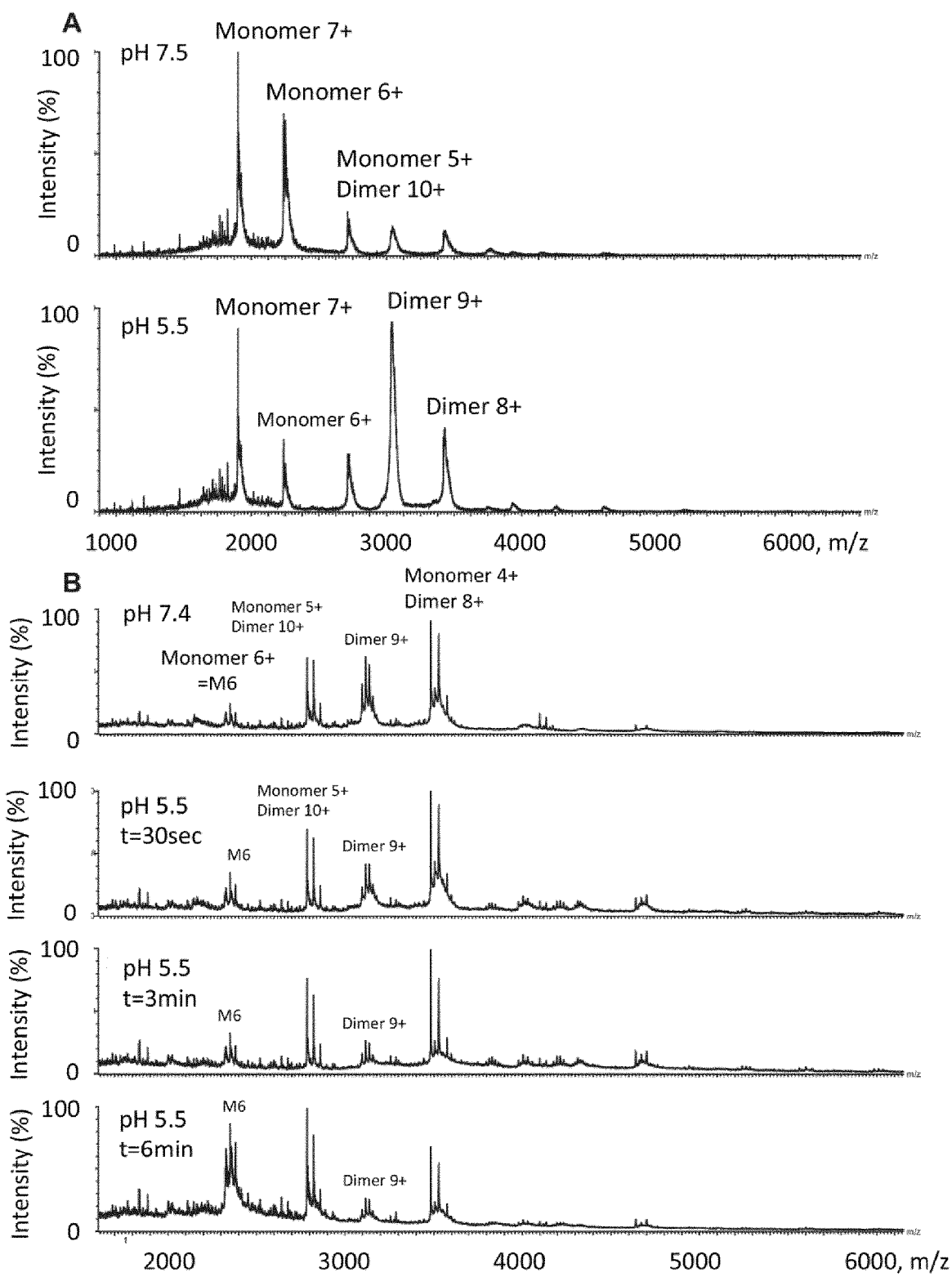
FIG. 10: Effect of pH changes on isolated NT and CT. (A) NT dimerizes at low pH. (B) Low pH induces dimer destabilization of CT and shifts the protein towards higher charge states within the same time scale as observed for NT2RepCT aggregation.

To further investigate the pH-dependent assembly of NT2RepCT at a molecular level, we used nano-electrospray mass spectrometry (nESI-MS). As expected, nESI-MS at pH 7.5 showed the presence of a major molecular species of 66560 Da, which corresponds to the native NT2RepCT dimer. Lowering the pH to approximately 5.5 induces a significant shift in the quarternary structure. Oligomers (mainly tetramers, arrow in FIG. 4B) could be observed up to one minute after the addition of formic acid directly to the sample in the electrospray capillary. Following loss of the higher oligomers, only low-intensity peaks corresponding to dimers could be detected, which further decreased to baseline over the course of five minutes (FIG. 4B). These findings correlate well with the pH-dependent lock and trigger actions of the terminal domains. NT on its own undergoes rapid antiparallel dimerization at low pH (FIG. 10), which has been suggested to lead to cross-linking of the spidroins into an infinite-mer. For CT in isolation on the other hand, exposure to low pH leads to gradual unfolding, as indicated by an increasing amount of monomers, and eventually amyloid-like β-sheet nuclei, indicated by some higher charge states (FIG. 10). In analogy to amyloid-like fibrils (Solvent effects on self-assembly of beta-amyloid peptide. Shen C L, Murphy RM.Biophys J. 1995 August; 69(2):640-51) addition of acetonitrile could not dissolve higher-order oligomers of NT2RepCT, while concentrated formic acid recovered the monomer signal, indicating dissociation of the aggregates through denaturation (FIG. 4B).

Example 6: Mechanical Properties of Spun NT2RepCT Fibers

Figure 5:
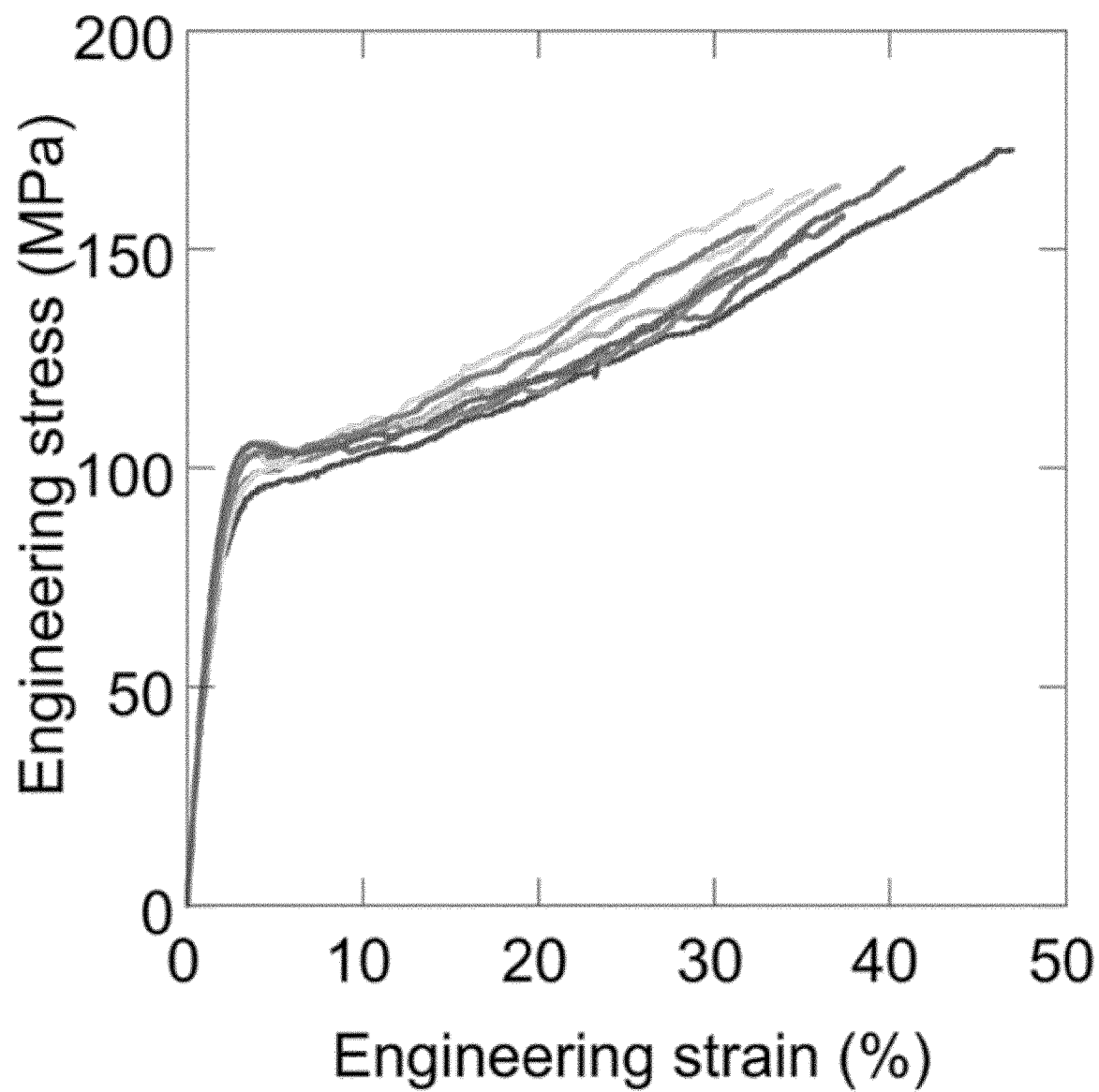
FIG. 5: Tensile properties of NT2RepCT fibers. Engineering stress/strain curves for eight separate NT2RepCT fibers.

The strength and extensibility of native dragline fibers differ a lot between spider species and are also highly dependent on environmental factors like humidity and temperature, but they all display initial elastic behavior up to a yielding point, after which plastic deformation occurs. The behavior of as spun NT2RepCT fibers when exposed to stress is similar to native dragline silk, but with lower tensile strength and higher strain (FIG. 5). NT2RepCT fibers as-spun into a pH 5 aqueous collection bath have a toughness of 45±7 MJ/m$^3$ (FIG. 5, Table 3), approaching the toughness of *A. trifasciata* dragline silk (100±40 MJ/m$^3$)[39] (Table 3). The Young's modulus is around 6 GPa, which is half the value of native *Argiope trifasciata* dragline silk.

droin. NT2RepCT fibers are, to the best of our knowledge, the toughest as-spun fibers so far produced (Table 3).

Example 7: Solubility of Dry Fibers in Different Solvents

Dry fibers are dissolved in dH$_2$O. The inventors studied which aqueous buffers and solvents that dry fibers can be put in without being dissolved.

Spinning fibers was performed in glass capillaries as described in Example 3 Fibers were spun into a collection bath with 500 mM NaAc and 200 mM NaCl, pH 5. As-spun fibers were pulled up from the collection bath and allowed to dry, after which single fibers were dipped into different solutions to check if fibers dissolved or not.

Tested dipping solutions:
1. 200 mM Citric acid, pH 3
2. 500 mM NaAc and 200 mM NaCl, pH 5
3. 1 M NaCl, pH 6.6
4. dH$_2$O
5. 20 mM Hepes/Mes, pH 5.5
6. 20 mM Hepes/Mes, pH 7.5
7. Mes, pH 5.15
8. 20 mM Tris, 100 mM NaCl, pH 8

TABLE 3

Comparison of mechanical properties of native dragline silk from *A. trifasciata* and different as-spun synthetic spider silk fibers

| Material | Native dragline silk *Argiope trifasciata* Ref 1 | NT2RepCT | eADF3 (AQ)$_{12}$NR3 Ref 2 | Synthetic MaSp1 and MaSp2 Ref 3 | Flag/MaSp2 A1S8$_{20}$ Ref 4 | MaSp2 1E Ref 5 | Flag GF Ref 6 |
|---|---|---|---|---|---|---|---|
| Diameter (μm) | ≈3 | 12 ± 2 | 39 ± 6 | 61 ± 2 | 32 ± 16 | 106 ± 5 | 37 ± 1 |
| Extensibility (%) | 17 ± 0.04 | 37 ± 5 | 7 ± 2 | 1.1 ± 0.3 | 3.7 ± 1 | 0.8 ± 0.3 | 1.1 ± 0.9 |
| Strength (MPa) | 890 ± 130 | 162 ± 8 | 54 ± 16 | 33 ± 7 | 28 ± 17 | 14 ± 4 | 19 ± 5 |
| Toughness (MJ m$^{-3}$) | 100 ± 40 | 45 ± 7 | 2 ± 0.8 | 0.2 ± 0.1 | 0.5 ± 0.3 | 0.06 ± 0.03 | 0.12 ± 0.11 |
| Young's modulus (GPa) | 11.6 ± 0.7 | 6 ± 0.8 | 2 ± 0.9 | ≈3 | 0.8 ± 0.5 | 1.7 ± 0.4 | |

Ref 1. Plaza, G. R., Perez-Rigueiro, J., Riekel, C., Perea, G. B., Agullo-Rueda, F., Burghammer, M., Guinea, G. V., Elices, M.. Relationship between microstructure and mechanical properties in spider silk fibers: identification of two regimes in the microstructural changes. *Soft matter* 8, 6015-6026, (2012).
Ref 2. Heidebrecht, A. et al. Biomimetic fibers made of recombinant spidroins with the same toughness as natural spider silk. *Adv Mater* 27, 2189-2194, (2015).
Ref 3. Copeland, C. G., Bell, B. E., Christensen, C. D., Lewis, R. V. Development of a Process for the Spinning of Synthetic Spider Silk. *ACS Biomaterials Science and Engineering* 1, 577-584, (2015).
Ref 4. Teulé F. F., W. A.; Cooper, A. R.; Duncan, J. R.; Lewis R. V. Modifications of spider silk sequences in an attempt to control the mechanical properties of the synthetic fibers. *J Mater Sci* 42, 8974-8985, (2007).
Ref 5. Albertson, A. E., Teule, F., Weber, W., Yarger, J. L. & Lewis, R. V. Effects of different post-spin stretching conditions on the mechanical properties of synthetic spider silk fibers. *J Mech Behav Biomed Mater* 29, 225-234, (2014).
Ref 6. Adrianos, S. L. et al. *Nephila clavipes* Flagelliform silk-like GGX motifs contribute to extensibility and spacer motifs contribute to strength in synthetic spider silk fibers. *Biomacromolecules* 14, 1751-1760, (2013).

Previously published methods to produce artificial spider silk fibers include electrospinning, hand-drawing, spinning through microfluidic devices, and wet spinning, often into coagulation baths of aqueous alcohols. None of these methods have resulted in fibers with mechanical properties equal to those of native spider dragline silk, probably due to a combination of the proteins being denatured in the production and spinning processes and lack of biomimetic conditions. As-spun fibers have maximum tensile stress in the range of 14-55 MPa, and strain levels between 1-7%, resulting in a toughness of up to 2 MJ/m$^3$ (Table 3). To increase mechanical properties of the fibers, different post-spinning treatments are required. The toughest fiber so far published, with maximum stress of 500 MPa and strain of 15±5% was obtained for a native-sized recombinant protein without terminal domains that had been post-stretched 500%, but stress levels of as-spun fibers were not reported. In light of these results, our as-spun fibers have surprisingly good mechanical properties, considering that only about 2% of the native repetitive region is included in the minispi- Fibers were not dissolved in dipping solutions 1-3, but were dissolved in solutions 4-8. It was concluded that a combination of pH and ionic strength are factors that influence the solubility.

Example 8: Spinning of NT2RepCT into Different Collection Baths

To study the influence of the composition and ionic strength of the collection bath on spinning NT2RepCT fibers, additional tests were performed in a setting similar to Example 3, except for the solution in the collection bath.

Tested collection baths:
1. 1000 mM NaAc buffer with 400 mM NaCl, pH 5
2. 500 mM sodium acetate (NaAc) buffer with 200 mM NaCl, pH 5
3. 20 mM NaAc buffer, pH 5
4. 20 mM phosphate buffer, pH 6.2
5. 20 mM tris, 500 mM NaCl, pH 7.2
6. 80% aq. isopropanol 7. 40% aq.isopropanol, 500 mM NaAc, 200 mM NaCl
8. 60% methanol, 40% water
9. 60% aq. methanol, 500 mM NaAc, 200 mM NaCl
10. 33% PEG 6000(Polyethylene glycol 6000)
11. 16.5% PEG 6000, 500 mM NaAc, 200 mM NaCl, pH 5

Figure 11:
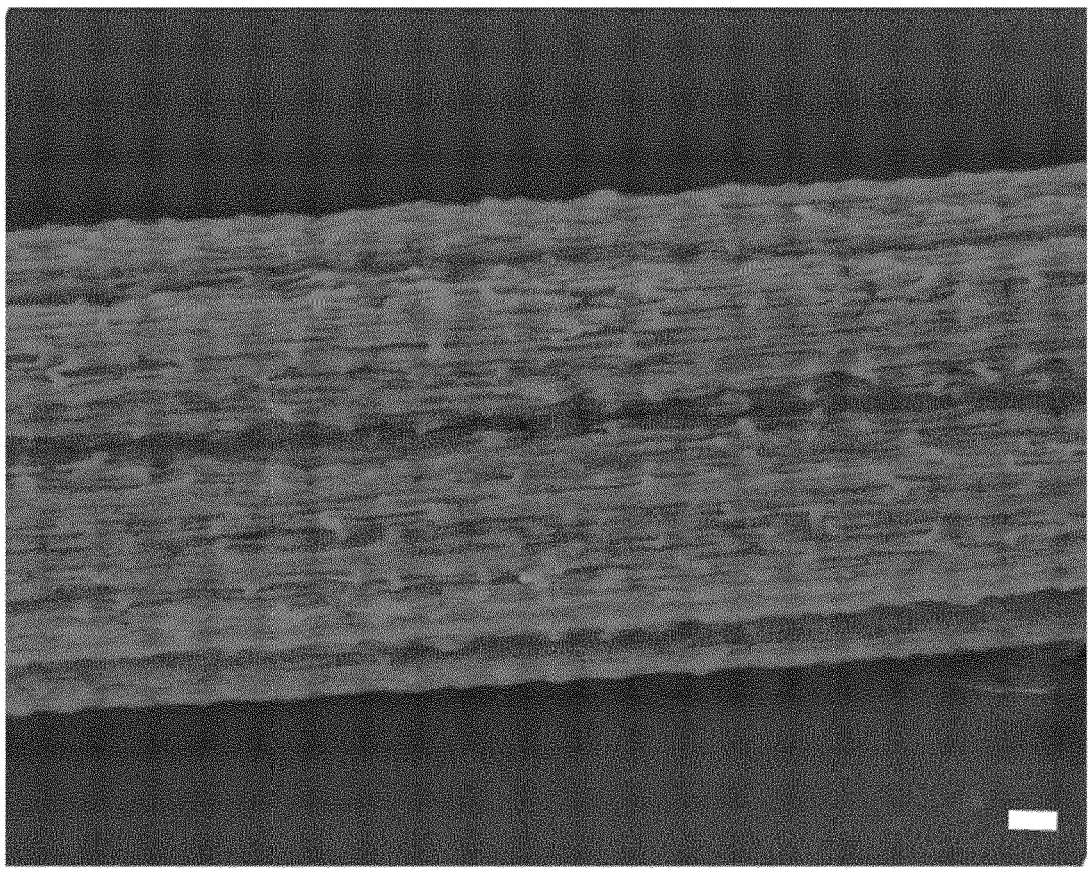
FIG. 11: Scanning electron micrograph of NT2RepCT fiber spun into isopropanol. Scale bar is 5 µm.

Continuous fibers were formed in collection baths 1-2, 6-11. Collection baths 3-5 gave only short fibers that dissolved easily. The PEG fibers looked quite similar to the fibers prepared in sodium acetate buffer, while the isopropanol (FIG. 11) and methanol fibers had a different macroscopic appearance. Isopropanol fibers were less opaque than NaAc fibers. Methanol fibers were fully transparent, and more gel-like.

The fibers that seemed strongest were produced in collection bath 2 (500 mM NaAc, 200 mM NaCl pH 5). The fibers that were easiest to post-stretch in air after spinning (i.e. more extendible) were produced in collection bath 11 (16.5% PEG, 500 mM NaAc buffer, 200 mM NaCl pH 5).

Example 9: Tensile Properties and Secondary Structure of NT2RepCt Fibers Spun in Different Collection Baths, at Different Temperatures, or Post-Stretched in Different Baths Aims
1) To study the influence of the composition of the collection bath on tensile properties of NT2RepCT fibers
2) To study the influence of post-stretching on tensile properties of NT2RepCT fibers Methods
Study 1): NT2RepCT fibers were spun as described in the Example 3, into following different collection baths:
  160223_1: 500 mM NaAc, 200 mM NaCl, pH 5
  160223_2: 500 mM NaAc, 200 mM NaCl, 15% PEG, pH 5
  160303_4: 500 mM NaAc, 200 mM NaCl, pH 4.25
Study 2): NT2RepCT fibers were spun as described in Example 3 into a collection bath with 500 mM NaAc, 200 mM NaCl, pH 5 and were subsequently:
  160223_4: post-stretched in 50% MetOh and 500 mM NaAc, 200 mM NaCl, pH 5;
  160223_5: post-stretched in 30% PEG;
  160303_5a: post-stretched in 80% isopropanol; or
  160303_5b: dipped in 80% isopropanol (without stretching)

Tensile tests (160223 samples) were performed as described in Example 3. Alternatively, (160303 samples) tensile tests were performed using the same procedure as described in Example 3, except for that the tensile tester brand was Shimadzu.

Results
Spinning into a collection bath containing PEG increases the toughness of the fibers, as compared to collection bath with only 500 mM NaAc, 200 mM NaCl, pH 5. However, the NT2RepCT fibers (160223_1) spun into 500 mM NaAc, 200 mM NaCl, pH 5 had a much lower toughness than NT2RepCT fibers from other batches.

Post-stretching in presence of methanol increases the tensile strength of the fibers, while post-stretching in 30% PEG increases the strain of the fibers.

Lowering the pH to 4.25 yields fibers that are much more fragile.

Post-stretching in isopropanol increases the tensile strength, but decreases strain, while only dipping in isopropanol increases the strain.

Example 10: Pilot Study on 3D Printing with NT2RepCT

The study aimed to test printing fiber structures with NT2RepCT protein and printing NT2RepCT gel fibers.

NT2RepCT was expressed, purified and concentrated as described in Example 1.

The spinning setup was as described in Example 3. The pulled glass capillary was then moved around while spinning, to print names and symbols.

For gel experiments, the highly concentrated NT2RepCT protein was kept in a syringe and extruded through a 27 G needle into a petri dish. A gel-structure was printed, after which a low pH buffer (500 mM NaAc, 200 mM NaCl, pH5) was poured in the petri dish.

Figure 12A:
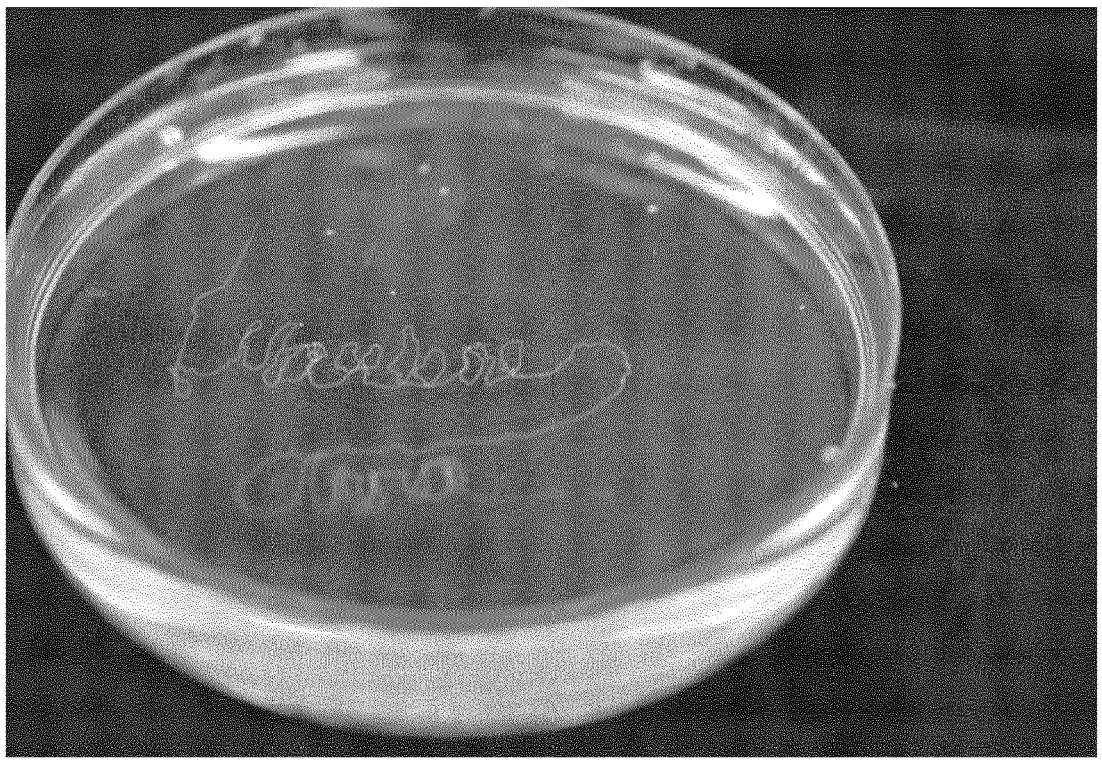
FIG. 12: Pilot experiments on 3D-printing. A. Printed names with NT2RepCT fiber in low pH buffer. B. Printed name with NT2RepCT gel. C. Printed name with NT2RepCT gel, solidified by pouring pH 5 sodium acetate buffer on the printed structure.
Figure 12B:
Figure 12C:

Both studies show the feasibility of printing NT2RepCT using a 3D printer. In both studies, names and symbols could be printed (FIG. 12A-C). A 3D printer could thus print either in dry state, or in a wet state with low pH.

Comparative Example 11: Comparative Examples Fiber Formation

Three different constructs: MaSpCT, NT4rep, 4repCT (all constructs contain parts from MaSp, i.e. no MiSp CT is included) were expressed, purified and fiber formation was performed by using a gentle tilting method in glass tubes, essentially as described by Stark et al 2007, but with addition of lowering of pH to enable studies of the influence of pH on the fiber formation properties of the different minispidorin constructs.

Methods
An over-night culture of the different constructs was prepared by inoculating 20 mL of LB media (with kanamycin) from a glycerol stock. The overnight culture was grown at 30° C., 200 rpm.

5 ml ON culture was added to 500 mL fresh LB media (with kanamycin) and grown at 30° C., 200 rpm until OD 0.9, after which the temperature was lowered to 25° C. and IPTG was added (final concentration 0.3 mM). Expression was continued for four hours, after which the cultures were centrifuged at 5000 rpm, 4° C. for 20 minutes. Pellets were dissolved in 30 ml 20 mM Tris pH 8 and stored at −20° C.

Cells were lysed by adding 600 ul lysozyme while thawing. When cells were thawed, 15 ul DNase and 60 ul (1 M) MgCl2 was added and the samples were incubated on ice for 30 minutes. The lysates were centrifuged at 15000 rpm, 4° C., 30 mins after which the supernatant was loaded onto a Ni-sepharose column for purification. The column was washed with 20 mM Tris pH 8 and 20 mM Tris pH 8, 10 mM imidazole. The protein was eluted with 20 mM Tris, 300 mM imidazole pH 8. Thrombin (1 ug/mg protein) was added to the fusion protein and the samples were dialysed over night at 4° C. towards 20 mM Tris pH 8. The dialysed and cleaved samples were loaded on the Ni-sepharose column and the flowthrough containing the purified protein was collected, after which the protein purity was checked by SDS-PAGE and the protein concentration was measured at 280 nm.

Protein yield for the different constructs were:
  NT4rep: 21 mg from 1 L shake flask culture
  4repCT: 24 mg from 1 L shake flask culture
  MaSpCT: 14 mg from 1 L shake flask culture The protein was concentrated to ≤3 mg/ml, and samples were then diluted in buffers of different pH and salt conditions to 1 mg/ml. Maximum concentration of 4RepCT was 10 mg/ml, then the protein precipitated.

The method used for fiber formation was: gentle tilting in glass tubes (as described by Stark et al 2007).

Three different pHs were tested: pH 7.5, 6.5 and 5.5 ca 10 mM Hepes/Mes. With or without 154 mM NaCl.

Results

MaSpCT forms short fibers (≤5 mm) after ca 3 hours of gentle tilting. pH and salt conditions do not influence neither the rate of fiber formation, nor the size of the fibers.

NT4rep does not form fibers, irrespective of pH or salt conditions

4repCT forms fibers (ca 2 cm long) in all pHs, but fiber formation is slower at pH 5.5. Fiber formation is equally fast at pH 6.5 and 7.5 but fibers are smaller at the lower pH values.

A mix of NT4rep and 4repCT (0.5 mg/ml each) forms long (≤3 cm) fibers, faster at pH 5.5 than at pH 6.5 or 7.5, but much slower than 4repCT alone.

Example 12: Production and Spinning of 2RepCT

2RepCT can be concentrated to >100 mg/ml and is spun into fibers by pumping the protein through a spinning device.

PGB1-2RepCT is expressed and purified as described for NT2RepCT in Example 1. The His-PGB1-tag is removed by cleaving with thrombin over night at 4° C. followed by reverse Immobilized Metal Ion Affinity Chromatography (IMAC) after which 2RepCT is concentrated to 170 mg/ml (performed as described for NT2RepCT).

Round glass capillaries (G1, Narishige) with an outer diameter of 1.0 mm and inner diameter of 0.6 mm are pulled (Micro Electrode Puller, Stoelting co. 51217) to a tip diameter of 25 µm. A 1 ml syringe with Luer Lok tip (BD) is filled with 2RepCT (at 170 mg/ml) and connected to a 27 G steel needle (Braun) with an outer diameter of 0.40 mm. The needle is connected to the pulled glass capillary via polyethylene tubing. A neMESYS low pressure (290N) syringe pump (Cetoni) is used to eject the PGB1-KL4 at a flow rate of 20 µl/min into a collection bath with either 500 mM NaAc 200 mM NaCl pH 5.0 or 50% methanol and 50% NaAc (500 mM), NaCl (200 mM) pH 5 within a 50 mL Falcon tube.

Continuous fibers form instantaneously as the 2RepCT is extruded through the capillary tip into the methanol/low pH collection bath and can be collected in the bottom of the Falcon tube, as well as being pulled up from the collection bath.

In conclusion, the 2RepCT can be produced at high yield and purity under native conditions, responds to pH lowering from 7 to 5, and is highly soluble in aqueous buffer, pH 7-8.

Example 13: Expression and Spinning of a NT2+2RepCT Minispidroin

The DNA sequence of NcoIHisNt2×2RepCtHindIII was according to SEQ ID NO: 17. The amino-acid sequence of the expressed protein was according to SEQ ID NO: 18.

Expression

The expression was done in E. coli BL21 cells. Five ml of an 37° C. overnight cell culture in LB medium (with 70 ug/mL kanamycin) was transfered to 500 ml LB medium (with 70 ug/mL kanamycin) and cultured in shake flasks at 30° C. until $OD_{600}$ was 0.8-1.0. The temperature was then lowered to 20° C., and 150 µl of 1 M IPTG (final concentration 0.3 mM) was added to induce expression. After overnight culture, the cells were harvested by centrifugation at 5,000 rpm, at 4° C. for 15 minutes. Cells from 500 ml culture were resuspended in 30 ml of 20 mM pH 8 Tris buffer and stored at −20° C. overnight.

Lysis and Purification

The cells were thawed and 30 ml cells were divided to two tubes and each tube was filled up to 30 ml with Tris buffer pH 8.0. Next, 600 µl lysozyme was added to each tube which was then incubated on ice for 1.5 h, whereafter 15 µl DNAse and 60 µl 1 M $MgCl_2$ was added and the samples were incubated on ice for one hour. The lysate was then centrifuged at 27,000 g for 30 min at 4° C. The first supernatant (supernatant 1) was loaded on a Ni-NTA column. The pellet was then resuspended in 30 ml Tris buffer pH 8.0, and stored at −20° C. overnight. The next day the pellet was thawed, centrifuged at 27,000 g for 30 min at 4° C., and the second supernatant was collected and loaded on a Ni-NTA column.

The supernatants were loaded on a gravity flow Ni-NTA column. The column was washed with (1) 20 mM Tris pH 8.0, (2) 100 mM NaCl in 20 mM Tris pH 8.0 and (3) with 10 mM imidazole in 20 mM Tris pH 8.0. The proteins were eluted with 300 mM imidazole in 20 mM Tris pH 8.0 The eluate containing the target proteins was dialyzed using a Spectra/Por® dialysis membrane with a 6-8 kDa molecular weight cut-off overnight in cold room against 20 mM Tris, pH 8.0 in order to remove imidazole.

The yields were as follows.

1) 41 mg protein from supernatant 1.

2) 46 mg protein from supernatant 2.

Figure 13:
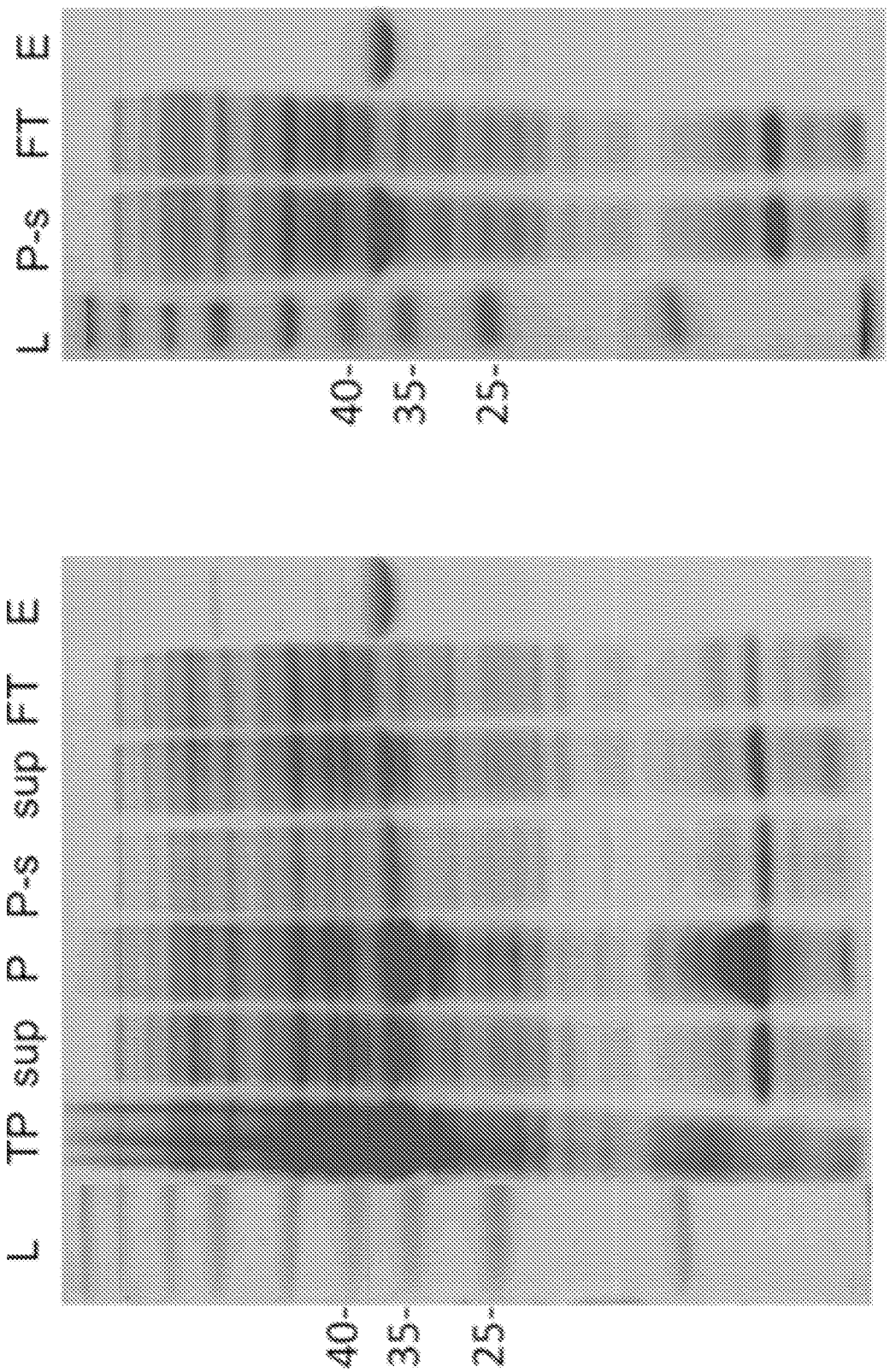
FIG. 13: SDS-PAGE analysis of the purification process of NT2+2RepCT. TP=total protein; Sup=supernatant after lysis; P=pellet after lysis; P-s=supernatant from overnight frozen pellet; FT=flow through (Ni-NTA column); E=protein eluted from column.
Figure 14:
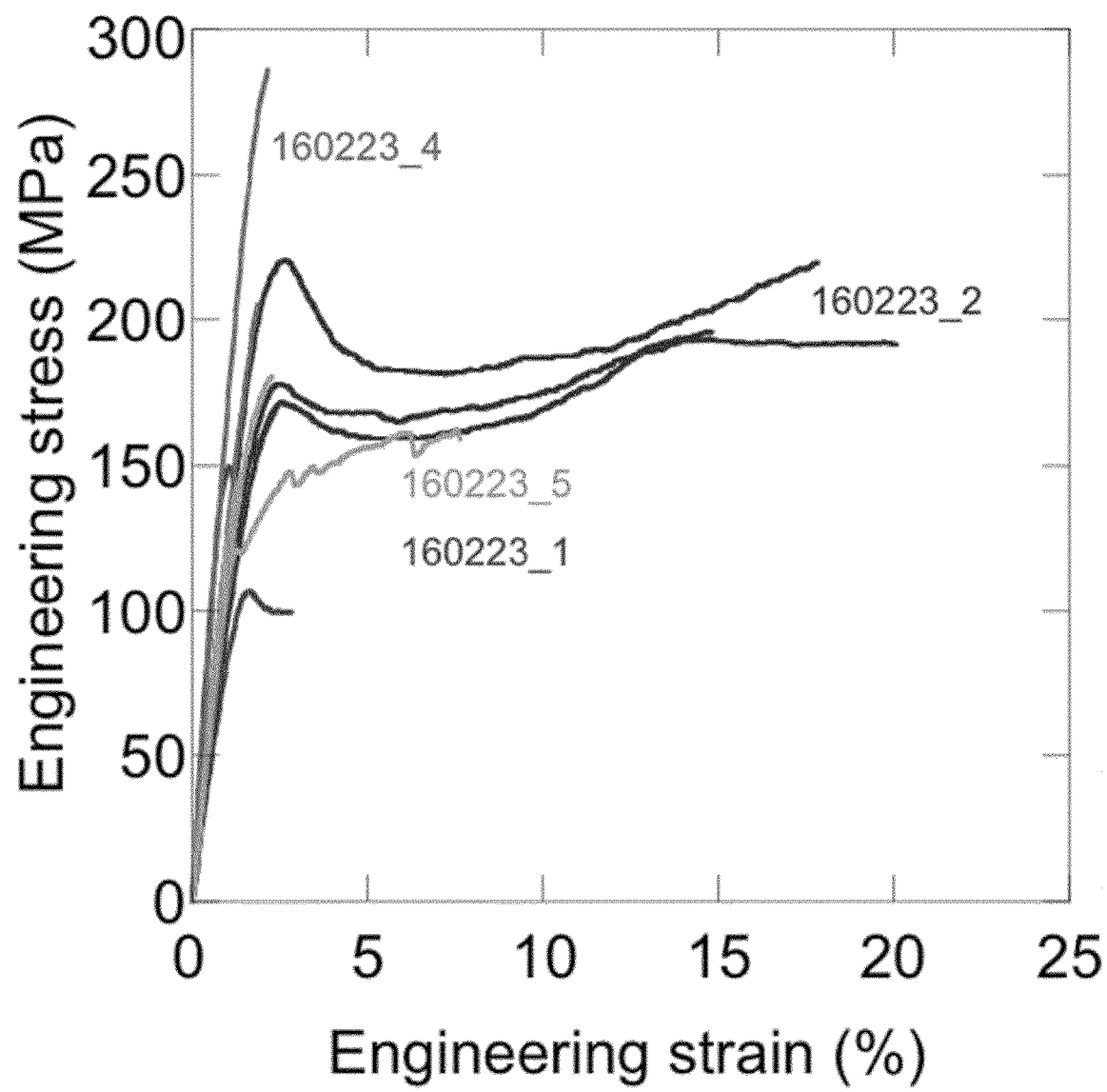
FIG. 14: Stress vs strain curve of NT2RepCT fibers spun into different collection baths, or post-stretched in different baths.

The yield is thus 87 mg from 1 L LB medium shake flask culture. SDS-PAGE analysis of the purification process is shown in FIG. 13.

Concentration and Solubility

The NT2×2RepCT protein could be concentrated to the >300 mg/ml at pH 8.0 in 20 mM Tris.

Fiber Spinning

Fibers were successfully spun as described for NT2RepCT. There were no apparent differences in macrostructure or fiber forming capabilities between NT2RepCT and NT2+2RepCT.

Example 14: Spider Silk as Cell Culture Matrix

Human fetal cardiac mesenchymal stromal cells (hfMSC) were derived from human fetal heart week 6-9 (Månsson-Broberg et al., Wnt/b-Catenin Stimulation and Laminins Support Cardiovascular Cell Progenitor Expansion from Human Fetal Cardiac Mesenchymal Stromal Cells, Stem Cell Reports, 2016).

The cells were seeded onto spider silk matrix in medium consisting of Dulbeccos Modified Eagle Medium F12 (DMEM/F12, Sigma) supplied with 2% fetal bovine serum, 2% B27, Glutamine and Mycozap. Medium was changed two-three times a week.

After 10 days in culture spider silk matrix with cells was snap-frozen and sectioned into 5 µm sections. These were fixed in 4% Formaldehyde in PBS and blocked with 5% rabbit serum in PBS for immunohistochemistry. For Laminin alpha 4 and Ki67 stainings the slides were boiled in citric buffer pH7 (Invitrogen) for antigen retrieval. All primary antibodies were mouse-anti-human and added in block buffer according to: Alpha Smooth muscle actin (αSMA, A2547, Sigma) 1/250, CD31 (M0823, Dako) 1/300, TroponinT (ab8295, Abcam) 1/800, Heparan Sulphate (370255-1, Amsbio) 1/500, Laminin alpha 4 (CL3183, Atlas antibodies) 1/200, Ki67 (MIB1, Dako) 1/75. The slides were incubated in humidity chamber in room temperature over night, washed in PBS and the secondary antibody, rabbit anti mouse (Alexa fluor 488), was added in blockbuffer 1/700. The slides were incubated in humidity chamber in room temperature 90 min, washed and mounted with Dapi.

It was found that the cells readily attach to spider silk and can proliferate, a number of cells express Ki67. The cells express αSMA, Laminin alpha 4 and Heparan Sulphate, indicating formation of an extracellular matrix and basal membrane. In vivo, this could help the cells survive after transplantation, since they are offered anchorage and familiar extra cellular matrix. Anoikis, apoptosis due to loss of anchorage, could thereby be minimized and cell survival after transplantation increased.

Example 15: Effect of the Number of Charged Residues (K/R/E/D) in the C-Terminal Domain on the Solubility of Minispidroins The inventors expressed minispidroins that are identical to NT2RepCT (SEQ ID 11, see Example 1) with the exception of the CT that was exchanged for:
  MiSp Ds CT (SEQ ID NO: 73): Minor ampullate silk protein *Deinopis spinosa*. Genbank accession no. ABD61589, resulting in NT2RepCT (MiSp Ds), SEQ ID NO: 74. This CT contains 11 charged residues.
  MaSp1 Ea CT (SEQ ID NO: 27): Major ampullate spidroin 1 *Euprosthenops australis*. Genbank accession no CAJ00428.1, resulting in NT2RepCT (MaSp1 Ea), SEQ ID NO: 75, containing 4 charged residues in the CT.
  ADF-4 (SEQ ID NO: 56): *Araneus diadematus* fibroin-4. Genbank accession no. ADU47856. resulting in NT2RepCT (ADF-4), SEQ ID NO: 76, containing 5 charged residues in the CT.
  MiSp Lh CT (SEQ ID NO: 45): Minor ampullate spidroin Latrodectus hesperus. Genbank accession no. ADM14322.1, resulting in NT2RepCT (MiSp Lh), SEQ ID NO: 77, containing 5 charged residues in the CT.

The inventors also mutated individually two charged amino acid residues in the CT of NT2RepCT (SEQ ID NO: 11) (R38 and D105, respectively, to alanine) yielding NT2RepCTR38A and NT2RepCTD105A (SEQ ID NOs: 78 and 79, respectively). The substitutions reduce the number of charged residues in the CT domain from 7 to 6.

These six new proteins were expressed as described for NT2RepCT. If the protein was found in sufficient yield in the soluble fraction, the proteins were purified by IMAC chromatography, concentrated and subsequently spun into fibers as described for NT2RepCT.

Results: NT2RepCT (MiSp Ds) could be expressed, was found in the soluble fraction, could be purified and concentrated to >300 mg/ml and spun in the same fashion as NT2RepCT.

NT2RepCT (MaSp1 Ea), NT2RepCT (ADF-4) and NT2RepCT (MiSp Lh) were all found in the insoluble fraction according to SDS PAGE analysis (FIGS. 20-22).

NT2RepCTR38A was expressed at high yields but was mainly found in the insoluble fraction. The NT2RepCTD105A was poorly expressed, and could not be obtained in sufficient amounts for protein concentration and fiber spinning.

Conclusions: the results support the conclusion that at least seven charged residues in the CT are necessary for obtaining NT2RepCT type of minispidroins that are soluble enough for purification, concentration and spinning in aqueous solvents.

MATERIALS AND METHODS

Protein Expression and Purification

The construct NT2RepCT (SEQ ID NO: 11) encodes for a protein according to SEQ ID NO: 11, composed of a 6xHis tag (MGHHHHHHM) and an N-terminal domain based on the *E. australis* MaSp1 sequence:

```
(SHTTPWTNPGLAENFMNSFMQGLSSMPGFTASQLDDMSTIAQSMVQSIQ

SLAAQGRTSPNKLQALNMAFASSMAEIAASEEGGGSLSTKTSSIASAMSN

AFLQTTGVVNQPFINEITQLVSMFAQAGMNDVSA),
``` a repetitive part consisting of two polyalanine/ glycine rich repeat regions from MaSp1 of *E. australis*:
```
(GNSGRGQGGYGQGSGGNAAAAAAAAAAAAAAAGQGGQGGYGRQSQGAGS AAAAAAAAAAAAAAGSGQGGYGGQGQGGYGQSGNS),
```
and a C-terminal domain based on the *A. ventricosus* MiSp sequence, preceded by a linker of 25 amino acids:
```
(VTSGGYGYGTSAAAGAGVAAGSYAGAVNRLSSAEAASRVSSNIAAIASGG

ASALPSVISNIYSGVVASGVSSNEALIQALLELLSALVHVLSSASIGNVSS

VGVDSTLNVVQDSVGQYVG).
```

The construct was cloned into a pT7 plasmid and transformed into BL21 (DE3) *E. coli*. Luria broth media with kanamycin (70 mg/l) was inoculated with a glycerol stock of *E. coli* containing NT2RepCT and grown over night at 37° C. with shaking (200 rpm). The overnight culture was used for a 1/100 inoculation of 500 ml LB media with kanamycin, which was then cultured at 30° C. with shaking (200 rpm) until $OD_{600}$ reached 0.8, after which the temperature was lowered to 20° C. and protein expression was induced by adding isopropylthiogalactoside (IPTG) to a final concentration of 0.3 mM. The cells were cultured over night at 20° C. with shaking (200 rpm) and were then harvested by centrifugation for 20 minutes at 5000 rpm, 4° C. The pellets were resuspended in 20 mM Tris pH 8 and frozen at −20° C., or lysed immediately after resuspension.

Lysis was performed in a cell disrupter (T-S Series Machine, Constant Systems Limited, England) at 30 kPsi, after which the lysate was centrifuged at 27 000 g, at 4° C. for 30 minutes. Supernatants were loaded on a Ni-NTA column and the protein was eluted with 300 mM imidazole. The eluted protein was dialyzed against 20 mM Tris pH 8, at 4° C. over night, using a Spectra/Por dialysis membrane with a 6-8 kDa molecular weight cutoff. SDS-polyacrylamide (12%) gel electrophoresis and Coomassie Brilliant Blue staining was used to determine the purity of the protein. Broad Range Protein Ladder (ThermoFisher Scientific) was used as a size standard.

The protein was concentrated using centrifugal filter units (Vivaspin 20, GE healthcare) with a 10 kDa molecular weight cutoff at 4000 g in rounds of 20 minutes. To determine the protein concentration, 1 µl protein was diluted 400 times in 20 mM Tris and the absorbance at 280 nm was recorded.

Size Exclusion Chromatography

A Superdex 200 HR column (Amersham Biosciences) was used to run 200 µl of purifed protein sample in TBS running buffer (20 mM Tris, 150 mM NaCl and 1 mM EDTA, pH 8.0). The flow rate used was 0.5 ml/min. Molecular mass standards Ribonuclease A (13.7 kDa), Carbonic anhydrase (29 kDa), Ovalbumin (43 kDa), Conalbumin (75 kDa), Aldolase (158 kDa) and Ferritin (440 kDa) were used for calibration.

Mass Spectrometry

For MS analysis, NT2RepCT was reconstituted into 100 mM ammonium acetate, pH 7.5 using biospin buffer exchange columns (Bio-Rad Laboratories). Silk assembly was induced by adding formic acid to a final concentration of 0.02% in a microcentrifuge tube, resulting in a pH of 5.5. As a reference for time-dependent assembly of spidroin, bovine ubiquitin (Sigma) was added to NT2RepCT samples at a final concentration of 0.2 mg/mL prior to the addition of formic acid. Samples were then immediately loaded into in-house produced gold-coated borosilicate capillaries and spectra were acquired continuously at 1 scan/sec for 10 minutes.

For fibril dissolution, either concentrated formic acid or acetonitrile were added to a final concentration of 50% after 30 min incubation of NT2RepCT at pH 5.5. Spectra were acquired on a Synapt G1 T-wave mass ion mobility spectrometer (Waters) operated in ToF mode and equipped with a 32 k quadrupole for high-mass analysis. The settings were: capillary voltage, 1.4 kV; sample cone 20 V; source temperature, 20° C.; trap collision energy, 100 V; transfer collision energy, 10 V; trap DC bias 8 V. Backing pressure was maintained around 7 mbar. Data were analyzed using the MassLynx 4.1 software package (Waters). For each time-point, 60 scans were combined and spectra intensities normalized to the ubiquitin signal. Relative intensities were extracted using mMass and plotted using GraphPad 5.0.

Fiber Spinning

Round glass capillaries (G1, Narishige) with an outer diameter of 1.0 mm and inner diameter of 0.6 mm were pulled (Micro Electrode Puller, Stoelting co. 51217) to a tip diameter of 10-30 µm. A 1 ml syringe with Luer Lok tip (BD) was filled with NT2RepCT of a high concentration (100-500 mg/ml) and connected to a 27 G steel needle (Braun) with an outer diameter of 0.40 mm. The needle was connected to the pulled glass capillary via polyethylene tubing. A neMESYS low pressure (290N) syringe pump (Cetoni) was used to eject the NT2RepCT at a flow rate of 1-20 µl/min into a low pH collection bath consisting of 500 mM sodium acetate buffer and 200 mM NaCl (pH 5). After formation, the fibers were pulled out of the collection bath and put on plastic to dry, or rolled up onto frames. Fibers were post-stretched by holding them between two tweezers in a low pH bath (500 mM NaAc with 200 mM NaCL, pH 5) for a few seconds, after which they were pulled to twice the original length, and put to dry on plastic.

For testing the influence of pH on spinning, different buffer systems and molarities of those buffer systems were used; sodium phosphate (100 mM) for pH>5.5, sodium acetate (100-500 mM) for pH 5.5-4, and citric acid (100-300 mM) for pH<4.

Fourier Transform Infrared (FTIR) Spectroscopy

FTIR analysis was carried out on liquid and solid samples using a Thermo Scientific Nicolet iS5 with iD5 ATR at room temperature. For protein in solution, 254 scans were collected for each spectrum, while for fibers, 16 scans were performed. Three spectra were obtained for each type of sample and averaged for the curves shown.

Tensile Strength Measurements of Fibers

Fiber samples were mounted onto plastic frames with 20 mm gauge length using tape and glue (Loctite® Super Glue Professional). Fibers were visualized under a light microscope (Leica DMI3000 B) using 40× object lens. Three photomicrographs were taken along the length of the fiber, and the diameter was measured from the photomicrographs using Carl Zeiss Zen 2012 to get an average diameter of the individual fiber piece. The sides of the plastic frame were cut off and the specimens were mounted in an Instron 4411 tensile testing machine. Force was measured with a Precisa XT 220 balance (resolution ±1 µN). The length of fiber where it was taut but not subjected to load was determined. Tensile test was performed at a pulling rate of 1 mm/min under nominal environmental conditions 24° C. and 30% relative humidity. All the tensile properties were calculated using KaleidaGraph. For the calculation of true stress and true strain, constant volume of fiber throughout the testing was assumed. The following equations were applied:

$$\sigma_T \sigma_E (1+\varepsilon_E) \quad (1)$$

$$\varepsilon_T = \ln(1+\varepsilon_E) \quad (2)$$

where
$\sigma_T$=true stress
$\sigma_E$=engineering stress
$\varepsilon_T$=true strain
$\varepsilon_E$=engineering strain Scanning Electron Microscopy of Fibers Dry fibers (as-spun or post-stretched in 500 mM NaAc 200 mM NaCl pH 5.0) were put on scanning electron microscopy stubs, coated with gold/palladium for two minutes, and observed and photographed on a Zeiss Supra 35VP scanning electron microscope.

Study of Micellar Structures on TEM and Cryo-EM

NT2RepCT (5 mg/ml) was diluted to 0.001 mg/ml in 20 mM Tris buffer, pH 8.0. Negatively stained grids were prepared by incubating the sample for 30 seconds in a drop of 2% phosphotungstic acid, pH 7.8, blotting excess solution off and letting it dry. For cryo-electron microscopy, 3 µl aliquots of sample were applied to glow-discharged 400-mesh Quantifoil holey carbon grids. The cryo-samples were prepared in a controlled environment, at 16° C. and 100% humidity, using automated Vitrobot (FEI, Eindhoven, The Netherlands). Data was acquired with a JEOL JEM-2100f microscope operated at 200 kV and a nominal magnification of 80000. Images were collected with TVIPS TemCam-F415 4k×4k CCD-camera (Tietz Video and Image Processing Systems GmbH, Gauting, Germany). The size of the micelles was estimated using the image processing program ImageJ.

PGB1-2RepCT

DNA Sequence of PGB1-2RepCT was according to SEQ ID NO: 13 whereas the protein sequence of PGB1-2RepCT was according to SEQ ID NO:14).

The invention claimed is:

1. An aqueous solution of a recombinant spider silk protein having a protein concentration of the recombinant spider silk protein of at least 100 mg/ml, wherein the recombinant spider silk protein consists of no more than 800 amino acids, and comprises a set of domains, wherein:
   a. an optional NT-domain, if present, consists of a sequence of 100 to 160 amino-acid residues derived from a N-terminal domain of a spider silk protein, wherein the NT-domain consists of a sequence having at least 50% sequence identity to SEQ ID NO:2 and/or at least 80% sequence identity to any one of SEQ ID NO:1 and SEQ ID NOs:80-97;
   b. a REP-domain consists of a sequence of 30 to 600 amino acid residues derived from a repetitive segment of a spider silk protein;
   c. a CT-domain consists of a sequence of 70 to 120 amino acid residues derived from a C-terminal domain of a spider silk protein, wherein the amino acid sequence of the CT-domain is selected from the group consisting of:
i. a sequence having at least 81% sequence identity to SEQ ID NO:64 or any one of SEQ ID NOs:62-65 or 67-73; and
ii. a Sequence having at least 80% sequence identity to SEQ ID NO:64 or any one of SEQ ID NOs:62-65 or 67-73, wherein the sequence comprises at least 7 residues independently selected from K, R, E and D; wherein the set of domains is arranged according to the formula (NT)-REP-CT; and wherein said recombinant spider silk protein comprises an amino acid sequence having at least 80% sequence identity to the sequence of SEQ ID NO: 11, SEQ ID NO: 14, or SEQ ID NO: 74.

2. The aqueous solution of the recombinant spider silk protein according to claim 1, wherein said aqueous solution is:
(i) a water solution; or
(ii) a water solution without organic solvents; or
(iii) an aqueous solution comprising less than 10% (v/v) organic solvents.

3. The aqueous solution of the recombinant spider silk protein according to claim 1, wherein said aqueous solution is a water solution.

4. The aqueous solution of the recombinant spider silk protein according to claim 1, wherein said aqueous solution is a water solution without organic solvents.

5. The aqueous solution of the recombinant spider silk protein according to claim 1, wherein said aqueous solution is an aqueous solution comprising less than 10% (v/v) organic solvents.

6. The aqueous solution of the recombinant spider silk protein according to claim 1, wherein said recombinant spider silk protein comprises an amino acid sequence having at least 90% sequence identity to the sequence of SEQ ID NO: 11, SEQ ID NO: 14, or SEQ ID NO: 74.

7. The aqueous solution of the recombinant spider silk protein according to claim 1, wherein said recombinant spider silk protein comprises an amino acid sequence having at least 80% sequence identity to the sequence of SEQ ID NO: 11.

8. The aqueous solution of the recombinant spider silk protein according to claim 7, wherein said recombinant spider silk protein comprises an amino acid sequence having at least 90% sequence identity to the sequence of SEQ ID NO: 11.

9. The aqueous solution of the recombinant spider silk protein according to claim 1, wherein the CT-domain is a sequence having at least 80% sequence identity to SEQ ID NO: 64 or SEQ ID NO: 73, wherein the sequence comprises at least 7 residues independently selected from K, R, E and D.

10. The aqueous solution of the recombinant spider silk protein according to claim 9, wherein the CT-domain is a sequence having at least 80% sequence identity to SEQ ID NO: 64.

11. The aqueous solution of the recombinant spider silk protein according to claim 10, wherein the CT-domain is a sequence having at least 90% sequence identity to SEQ ID NO: 64.

12. A recombinant spider silk protein consisting of no more than 800 amino acids,
wherein said recombinant spider silk protein comprises an amino acid sequence having at least 80% sequence identity to the sequence of SEQ ID NO: 11, SEQ ID NO: 14, or SEQ ID NO: 74; and
wherein said recombinant spider silk protein comprises a CT-domain which consists of a sequence of 70 to 120 amino acid residues derived from a C-terminal domain of a spider silk protein, and which has at least 7 residues independently selected from K, R, E and D.

13. The recombinant spider silk protein according to claim 12, wherein the CT-domain is a sequence having at least 80% sequence identity to SEQ ID NO:64 or any one of SEQ ID NOs: 62-65 or 67-73.

14. The recombinant spider silk protein according to claim 13, wherein the CT-domain is a sequence having at least 80% sequence identity to SEQ ID NO: 64 or SEQ ID NO: 73.

15. The recombinant spider silk protein according to claim 14, wherein the CT-domain is a sequence having at least 80% sequence identity to SEQ ID NO: 64.

16. The recombinant spider silk protein according to claim 15, wherein the CT-domain is a sequence having at least 90% sequence identity to SEQ ID NO: 64.

17. The recombinant spider silk protein according to claim 12, wherein said recombinant spider silk protein comprises an amino acid sequence having at least 90% sequence identity to the sequence of SEQ ID NO: 11, SEQ ID NO: 14, or SEQ ID NO: 74.

18. The recombinant spider silk protein according to claim 17, wherein said recombinant spider silk protein comprises an amino acid sequence having the sequence of SEQ ID NO: 11, SEQ ID NO: 14, or SEQ ID NO: 74.

19. The recombinant spider silk protein according to claim 12, wherein said recombinant spider silk protein comprises an amino acid sequence having at least 80% sequence identity to the sequence of SEQ ID NO: 11.

20. The recombinant spider silk protein according to claim 19, wherein said recombinant spider silk protein comprises an amino acid sequence having at least 90% sequence identity to the sequence of SEQ ID NO: 11.

21. The recombinant spider silk protein according to claim 20, wherein said recombinant spider silk protein comprises an amino acid sequence having the sequence of SEQ ID NO: 11.

* * * * *

SEQUENCE LISTING

```
<160> NUMBER OF SEQ ID NOS: 97

<210> SEQ ID NO 1
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)
```

```
<400> SEQUENCE: 1

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
            85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
            115                 120                 125

Gln Ala Gly Met Asn Asp Val Ser Ala
        130                 135

<210> SEQ ID NO 2
<211> LENGTH: 131
<212> TYPE: PRT
<213> ORGANISM: Artificial Sequence
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
```

```
<220> FEATURE:
<221> NAME/KEY: VARIANT
<222> LOCATION: (124)..(124)
<223> OTHER INFORMATION: Ser

<400> SEQUENCE: 2

Gln Ala Asn Thr Pro Trp Ser Ser Pro Asn Leu Ala Asp Ala Phe Ile
1               5                   10                  15

Asn Ser Phe Met Ser Ala Ala Ser Ser Ser Gly Ala Phe Ser Ala Asp
            20                  25                  30

Gln Leu Asp Asp Met Ser Thr Ile Gly Asp Thr Leu Met Ser Ala Met
        35                  40                  45

Asp Asn Met Gly Arg Ser Gly Lys Ser Thr Lys Ser Lys Leu Gln Ala
50                  55                  60

Leu Asn Met Ala Phe Ala Ser Ser Met Ala Glu Ile Ala Ala Ala Glu
65                  70                  75                  80

Ser Gly Gly Gly Ser Val Gly Val Lys Thr Asn Ala Ile Ser Asp Ala
                85                  90                  95

Leu Ser Ser Ala Phe Tyr Gln Thr Thr Gly Ser Val Asn Pro Gln Phe
            100                 105                 110

Val Asn Glu Ile Arg Ser Leu Ile Gly Met Phe Ala Gln Ala Ser Ala
        115                 120                 125

Asn Glu Val
    130

<210> SEQ ID NO 3
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
```

-continued

```
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
```

-continued

```
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
```

```
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 3

Gln Gly Ala Gly Gly Asn Ala Ala Ala Ala Ala Ala Ala Ala Ala Ala
1               5                   10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala Ala
        35                  40                  45

Ala Ala Ala Ala Ala Ala Ala Gly Arg Gly Gln Gly Gly Tyr Gly
    50                  55                  60

Gln Gly Ser Gly Gly Asn Ala Ala Ala Ala Ala Ala Ala Ala Ala Ala
65                  70                  75                  80

Ala Ala Ser Gly Gln Gly Gly Gln Gly Gly Gln Gly Gly Gln Gly Gln
            85                  90                  95

Gly Gly Tyr Gly Gln Gly Ala Gly Ser Ser Ala Ala Ala Ala Ala Ala
        100                 105                 110

Ala Ala Ala Ala Ala Ala Ala Ala Gly Gln Gly Gln Gly Arg Tyr Gly
    115                 120                 125

Gln Gly Ala Gly Gly Asn Ala Ala Ala Ala Ala Ala Ala Ala Ala Ala
130                 135                 140

Ala Ala Ala Gly Gln Gly Gly Gln Gly Gly Gln Gly Gly Leu Gly Gln
145                 150                 155                 160

Gly Gly Tyr Gly Gln Gly Ala Gly Ser Ser Ala Ala Ala Ala Ala Ala
        165                 170                 175

Ser Ala Ala Ala Ala Ala Ala Gly Arg Gly Gln Gly Gly Tyr Gly Gln
    180                 185                 190

Gly Ala Gly Gly Asn Ala Ala Ala Ala Ala Ala Ala Ala Ala Ala
        195                 200                 205

Ala Ala Ala Gly Gln Gly Gly Gln Gly Gly Tyr Gly Gly Leu Gly Gln
    210                 215                 220

Gly Gly Tyr Gly Gln Gly Ala Gly Ser Ser Ala Ala Ala Ala Ala Ala
225                 230                 235                 240

Ala Ala Ala Ala Ala Ala Ala Gly Gly Gln Gly Gly Gln Gly Gln Gly
            245                 250                 255

Arg Tyr Gly Gln Gly Ala Gly Ser Ser Ala Ala Ala Ala Ala Ala Ala
        260                 265                 270

Ala Ala Ala Ala Ala Ala Ala Gly Gln Gly Gln Gly Gly Tyr Gly Gln
        275                 280                 285

Gly Ala Gly Gly Asn Ala Ala Ala Ala Ala Ala Ala Ala Ala Ala Ala
        290                 295                 300

Ala Ala Gly Gln Gly Gly Gln Gly Gly Gln Gly Gly Leu Gly Gln Gly
305                 310                 315                 320

Gly Tyr Gly Gln Gly Ala Gly Ser Ser Ala Ala Ala Ala Ala Ala Ala
        325                 330                 335

Ala Ala Ala Ala Ala Ala Gly Arg Gly Gln Gly Gly Tyr Gly Gln Gly
    340                 345                 350
```

```
        Ala Gly Gly Asn Ala Ala Ala Ala Ala Ala Ala Glu Ala Ala
                    355                 360                 365

Ala Ala Gly Gln Gly Gly Gln Gly Gly Tyr Gly Gly Leu Gly Gln Gly
            370                 375                 380

Gly Tyr Gly Gln Gly Ala Gly Ser Ser Ala Ala Ala Ala Ala Ala
        385                 390                 395                 400

Ala Ala Ala Ala Ala Gly Arg Gly Gln Gly Gly Tyr Gly Gln Gly
                    405                 410                 415

Ala Gly Gly Asn Ala Ala Ala Ala Ala Ala Ala Ala Ala Ala
                    420                 425                 430

Ala Ala Gly Gln Gly Gly Gln Gly Gly Tyr Gly Gly Leu Gly Gln Gly
                    435                 440                 445

Gly Tyr Gly Gln Gly Ala Gly Ser Ser Ala Ala Ala Ala Ala Ala
        450                 455                 460

Ala Ala Ala Ala Ala Ala Gly Gly Gln Gly Gly Gln Gly Gln Gly Arg
        465                 470                 475                 480

Tyr Gly Gln Gly Ala Gly Ser Ser Ala Ala Ala Ala Ala Ala
                    485                 490                 495

Ala Ala Ala Ala Ala Ala Gly Arg Gly Gln Gly Gly Tyr Gly Gln Gly
                    500                 505                 510

Ser Gly Gly Asn Ala Ala Ala Ala Ala Ala Ala Ala Ala Ala
                    515                 520                 525

Ser Gly Gln Gly Ser Gln Gly Gly Gln Gly Gly Gln Gly Gly Gly
                    530                 535                 540

Tyr Gly Gln Gly Ala Gly Ser Ser Ala Ala Ala Ala Ala Ala Ala
        545                 550                 555                 560

Ala Ala Ala Ala Ala Ser Gly Arg Gly Gln Gly Gly Tyr Gly Gln Gly
                    565                 570                 575

Ala Gly Gly Asn Ala Ala Ala Ala Ala Ala Ala Ala Ala Ala
                    580                 585                 590

Ala Ala Gly Gln Gly Gly Gln Gly Gly Tyr Gly Gly Leu Gly Gln Gly
                    595                 600                 605

Gly Tyr Gly Gln Gly Ala Gly Ser Ser Ala Ala Ala Ala Ala Ala
            610                 615                 620

Ala Ala Ala Ala Ala Gly Gly Gln Gly Gly Gln Gly Gln Gly Gly Tyr
        625                 630                 635                 640

Gly Gln Gly Ala Gly Ser Ser Ala Ala Ala Ala Ala Ala Ala
                    645                 650                 655

Ala Ala Ala Ala Ala Gly Arg Gly Gln Gly Gly Tyr Gly Gln Gly Ser
                    660                 665                 670

Gly Gly Asn Ala Ala Ala Ala Ala Ala Ala Ala Ala Ala Ser
                    675                 680                 685

Gly Gln Gly Gly Gln Gly Gln Gly Gly Gln Gly Gln Gly Gly Tyr
                    690                 695                 700

Gly Gln Gly Ala Gly Ser Ser Ala Ala Ala Ala Ala Ala Ala Ala
        705                 710                 715                 720

Ala Ala Ala Ala Ala Gly Gln Gly Gln Gly Gly Tyr Gly Gln Gly Ala
                    725                 730                 735

Gly Gly Asn Ala Ala Ala Ala Ala Ala Ala Ala Ala Ala Ala
                    740                 745                 750

Gly Gln Gly Gly Gln Gly Gly Gln Gly Gly Leu Gly Gln Gly Gly Tyr
                    755                 760                 765
```

```
Gly Gln Gly Ala Gly Ser Ser Ala Ala Ala Ala Ala Ala Ala Ala
    770             775                 780

Ala Ala Ala Ala Ala Gly Arg Gly Gln Gly Gly Tyr Gly Gln Gly Val
785                 790                 795                 800

Gly Gly Asn Ala Ala Ala Ala Ala Ala Ala Ala Ala Ala Ala Ala
            805                 810                 815

Gly Gln Gly Gly Gln Gly Gly Gln Gly Gly Leu Gly Gln Gly Gly Tyr
                820                 825                 830

Gly Gln Gly Ala Gly Ser Ser Ala Ala Ala Ala Ala Ala Ala Ala
            835                 840                 845

Ala Ala Ala Ala Ala Gly Arg Gly Gln Gly Gly Tyr Gly Gln Gly Ser
850                 855                 860

Gly Gly Asn Ala Ala Ala Ala Ala Ala Ala Ala Ala Ala Ala Ser
865                 870                 875                 880

Gly Gln Gly Ser Gln Gly Gly Gln Gly Gly Gln Gly Gln Gly Gly Tyr
                    885                 890                 895

Gly Gln Gly Ala Gly Ser Ser Ala Ala Ala Ala Ala Ala Ala Ala
                900                 905                 910

Ala Ala Ala Ala Ser Gly Arg Gly Gln Gly Gly Tyr Gly Gln Gly Ala
                915                 920                 925

Gly Gly Asn Ala Ala Ala Ala Ala Ala Ala Ala Ala Ala Ala Ala
            930                 935                 940

Ala Gly Gln Gly Gly Gln Gly Gly Tyr Gly Gly Leu Gly Gln Gly Gly
945                 950                 955                 960

Tyr Gly Gln Gly Ala Gly Ser Ser Ala Ala Ala Ala Ala Ala Ala Ala
                965                 970                 975

Ala Ala Ala Ala Gly Gly Gln Gly Gly Gln Gly Gln Gly Gly Tyr Gly
            980                 985                 990

Gln Gly Ser Gly Gly Ser Ala Ala Ala Ala Ala Ala Ala Ala Ala
        995                 1000                1005

Ala Ala Ala Ala Ala Gly Arg Gly Gln Gly Gly Tyr Gly Gln Gly
    1010                1015                1020

Ser Gly Gly Asn Ala Ala Ala Ala Ala Ala Ala Ala Ala Ala
    1025                1030                1035

Ala Ala Ala Ala Gly Gln Gly Gly Gln Gly Gly Tyr Gly Arg Gln
    1040                1045                1050

Ser Gln Gly Ala Gly Ser Ala Ala Ala Ala Ala Ala Ala Ala
    1055                1060                1065

Ala Ala Ala Ala Ala Gly Ser Gly Gln Gly Gly Tyr Gly Gly Gln
    1070                1075                1080

Gly Gln Gly Gly Tyr Gly Gln Ser Ser Ala Ser Ala Ser Ala Ala
    1085                1090                1095

Ala Ser Ala Ala Ser Thr Val Ala Asn Ser Val Ser
    1100                1105                1110

<210> SEQ ID NO 4
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
```

```
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 4

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 5
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 5

Gly Gln Gly Gly Gln Gly Gln Gly Gly Tyr Gly Gln Gly Ala Gly Ser
1               5                   10                  15

Ser

<210> SEQ ID NO 6
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 6

Gly Arg Gly Gln Gly Gly Tyr Gly Gln Gly Ala Gly Gly Asn
1               5                   10
```

```
<210> SEQ ID NO 7
<211> LENGTH: 18
<212> TYPE: PRT
<213> ORGANISM: Artificial
<220> FEATURE:
<223> OTHER INFORMATION: Consensus sequence

<400> SEQUENCE: 7

Ala Ser Ala Ser Ala Ala Ala Ser Ala Ala Ser Thr Val Ala Asn Ser
1               5                   10                  15

Val Ser

<210> SEQ ID NO 8
<211> LENGTH: 8
<212> TYPE: PRT
<213> ORGANISM: Artificial
<220> FEATURE:
<223> OTHER INFORMATION: Consensus sequence

<400> SEQUENCE: 8

Ala Ser Ala Ala Ser Ala Ala Ala
1               5

<210> SEQ ID NO 9
<211> LENGTH: 8
<212> TYPE: PRT
<213> ORGANISM: Artificial
<220> FEATURE:
<223> OTHER INFORMATION: Consensus sequence

<400> SEQUENCE: 9

Gly Ser Ala Met Gly Gln Gly Ser
1               5

<210> SEQ ID NO 10
<211> LENGTH: 5
<212> TYPE: PRT
<213> ORGANISM: Artificial
<220> FEATURE:
<223> OTHER INFORMATION: Consensus sequence

<400> SEQUENCE: 10

Ser Ala Ser Ala Gly
1               5

<210> SEQ ID NO 11
<211> LENGTH: 346
<212> TYPE: PRT
<213> ORGANISM: Artificial
<220> FEATURE:
<223> OTHER INFORMATION: Chimeric protein

<400> SEQUENCE: 11

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Ala Phe Ala Ser
65                  70                  75                  80
```

Ser Met Ala Glu Ile Ala Ala Ser Glu Glu Gly Gly Ser Leu Ser
            85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
            130                 135                 140

Ser Gly Arg Gly Gln Gly Tyr Gly Gln Ser Gly Gly Asn Ala
145                 150                 155                 160

Ala Ala Ala Ala Ala Ala Ala Ala Ala Ala Ala Gly Gln
            165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Gly Ser Gly
            195                 200                 205

Gln Gly Gly Tyr Gly Gly Gln Gly Gln Gly Gly Tyr Gly Gln Ser Gly
            210                 215                 220

Asn Ser Val Thr Ser Gly Gly Tyr Gly Tyr Gly Thr Ser Ala Ala Ala
225                 230                 235                 240

Gly Ala Gly Val Ala Ala Gly Ser Tyr Ala Gly Ala Val Asn Arg Leu
            245                 250                 255

Ser Ser Ala Glu Ala Ala Ser Arg Val Ser Ser Asn Ile Ala Ala Ile
            260                 265                 270

Ala Ser Gly Gly Ala Ser Ala Leu Pro Ser Val Ile Ser Asn Ile Tyr
            275                 280                 285

Ser Gly Val Val Ala Ser Gly Val Ser Ser Asn Glu Ala Leu Ile Gln
            290                 295                 300

Ala Leu Leu Glu Leu Leu Ser Ala Leu Val His Val Leu Ser Ser Ala
305                 310                 315                 320

Ser Ile Gly Asn Val Ser Ser Val Gly Val Asp Ser Thr Leu Asn Val
            325                 330                 335

Val Gln Asp Ser Val Gly Gln Tyr Val Gly
            340                 345

<210> SEQ ID NO 12
<211> LENGTH: 1052
<212> TYPE: DNA
<213> ORGANISM: Artificial
<220> FEATURE:
<223> OTHER INFORMATION: Chimeric construct

<400> SEQUENCE: 12
ccatgggcca tcatcatcat catcatatga gccataccac cccgtggacc aacccgggcc      60
tggcggaaaa ctttatgaac agctttatgc agggcctgag cagcatgccg ggctttaccg     120
cgagccagct ggatgatatg agcaccattg cgcagagcat ggtgcagagc attcagagcc     180
tggcggcgca gggccgtacc agcccgaaca aactgcaggc gctgaacatg cgtttgcga     240 gcagcatggc ggaaattgcg gcgagcgaag aaggcggcgg cagcctgagc accaaaacca     300
gcagcattgc gagcgcgatg agcaacgcgt tcctgcagac caccggcgtg gtgaaccagc     360
cgtttattaa cgaaattacc cagctggtga gcatgtttgc gcaggcgggc atgaacgatg     420
tgagcgcggg gaattcggga cgaggtcaag gaggatatgg tcaaggttct ggaggtaatg     480
ctgctgccgc agccgctgcc gccgccgccg ccgctgcagc agccggacag ggaggtcaag     540

```
gtggatatgg tagacaaagc caaggtgctg gttccgctgc tgctgctgct gctgctgctg      600
ccgctgctgc tgctgcagga tctggacaag gtggatacgg tggacaaggt caaggaggtt      660
atggtcagag tgggaattcg gttacatctg gaggttacgg atatggaacc agtgcagctg      720
caggagctgg agttgcagca ggttcatatg caggtgctgt caatcgcttg tctagtgctg      780
aagctgccag tagagtatcc tctaatattg cagctattgc atctggtggt gcttccgccc      840
tccccagtgt tatttcaaat atttactcag gtgtcgttgc ttctggtgtt tcttctaatg      900
aagctctgat tcaagctctg ttggaactcc tttccgcact tgttcatgtt ttaagcagtg      960
cctctatcgg taatgttagc tcagtaggag tagatagtac attgaatgtt gttcaggatt     1020
cagtaggcca atatgtaggt taatgaaagc tt                                   1052

<210> SEQ ID NO 13
<211> LENGTH: 848
<212> TYPE: DNA
<213> ORGANISM: Artificial
<220> FEATURE:
<223> OTHER INFORMATION: Chimeric construct

<400> SEQUENCE: 13
ccatgggcca tcatcatcat catcatatgg ggaattcgat gcagtacaaa ctgatcatcg       60
acggtaaaac cctgaaaggt gaaaccacca ccgaagctgt tgacgctgct gctgctgaaa      120
aattcttcaa acagtacgct aacgacgacg gtatcgacgg tgaatggacc tacgacgacg      180
ctaccaaaac cttcaccgtt accgaattag tacctagagg atcagggaat tcgggacgag      240
gtcaaggagg atatggtcaa ggttctggag gtaatgctgc tgccgcagcc gctgccgccg      300
ccgccgccgc tgcagcagcc ggacagggag gtcaaggtgg atatggtaga caaagccaag      360
gtgctggttc cgctgctgct gctgctgctg ctgctgccgc tgctgctgct gcaggatctg      420
gacaaggtgg atacggtgga caaggtcaag gaggttatgg tcagagtggg accggtgtta      480
catctggagg ttacggatat ggaaccagtg cagctgcagg agctggagtt gcagcaggta      540
gttacgcagg tgctgtcaat cgcttgtcta gtgctgaagc tgccagtaga gtatcctcta      600
atattgcagc tattgcatct ggtggtgctt ccgccctccc cagtgttatt tcaaatattt      660
actcaggtgt cgttgcttct ggtgtttctt ctaatgaagc tctgattcaa gctctgttgg      720
aactcctttc cgcacttgtt catgttttaa gcagtgcctc tatcggtaat gttagctcag      780
taggagtaga tagtacattg aatgttgttc aggattcagt aggccaatat gtaggttaat      840
gaaagctt                                                              848

<210> SEQ ID NO 14
<211> LENGTH: 278
<212> TYPE: PRT
<213> ORGANISM: Artificial
<220> FEATURE:
<223> OTHER INFORMATION: Chimeric protein

<400> SEQUENCE: 14

Met Gly His His His His His His Met Gly Asn Ser Met Gln Tyr Lys
1               5                   10                  15

Leu Ile Ile Asp Gly Lys Thr Leu Lys Gly Glu Thr Thr Thr Glu Ala
            20                  25                  30

Val Asp Ala Ala Ala Ala Glu Lys Phe Phe Lys Gln Tyr Ala Asn Asp
        35                  40                  45

Asp Gly Ile Asp Gly Glu Trp Thr Tyr Asp Asp Ala Thr Lys Thr Phe
    50                  55                  60
```

```
Thr Val Thr Glu Leu Val Pro Arg Gly Ser Gly Asn Ser Gly Arg Gly
 65                  70                  75                  80

Gln Gly Gly Tyr Gly Gln Gly Ser Gly Gly Asn Ala Ala Ala Ala Ala
                 85                  90                  95

Ala Ala Ala Ala Ala Ala Ala Ala Ala Gly Gln Gly Gly Gln Gly
            100                 105                 110

Gly Tyr Gly Arg Gln Ser Gln Gly Ala Gly Ser Ala Ala Ala Ala Ala
            115                 120                 125

Ala Ala Ala Ala Ala Ala Ala Ala Gly Ser Gly Gln Gly Gly Tyr
            130                 135                 140

Gly Gly Gln Gly Gln Gly Gly Tyr Gly Gln Ser Gly Thr Gly Val Thr
145                 150                 155                 160

Ser Gly Gly Tyr Gly Tyr Gly Thr Ser Ala Ala Gly Ala Gly Val
                165                 170                 175

Ala Ala Gly Ser Tyr Ala Gly Ala Val Asn Arg Leu Ser Ser Ala Glu
            180                 185                 190

Ala Ala Ser Arg Val Ser Ser Asn Ile Ala Ile Ala Ser Gly Gly
            195                 200                 205

Ala Ser Ala Leu Pro Ser Val Ile Ser Asn Ile Tyr Ser Gly Val Val
            210                 215                 220

Ala Ser Gly Val Ser Ser Asn Glu Ala Leu Ile Gln Ala Leu Leu Glu
225                 230                 235                 240

Leu Leu Ser Ala Leu Val His Val Leu Ser Ser Ala Ser Ile Gly Asn
                245                 250                 255

Val Ser Ser Val Gly Val Asp Ser Thr Leu Asn Val Val Gln Asp Ser
            260                 265                 270

Val Gly Gln Tyr Val Gly
            275

<210> SEQ ID NO 15
<211> LENGTH: 108
<212> TYPE: PRT
<213> ORGANISM: Araneus ventricosus

<400> SEQUENCE: 15

Ala Ala Gly Ala Gly Val Ala Ala Gly Ser Tyr Ala Gly Ala Val Asn
1               5                   10                  15

Arg Leu Ser Ser Ala Glu Ala Ala Ser Arg Val Ser Ser Asn Ile Ala
                20                  25                  30

Ala Ile Ala Ser Gly Gly Ala Ser Ala Leu Pro Ser Val Ile Ser Asn
            35                  40                  45

Ile Tyr Ser Gly Val Val Ala Ser Gly Val Ser Ser Asn Glu Ala Leu
        50                  55                  60

Ile Gln Ala Leu Leu Glu Leu Leu Ser Ala Leu Val His Val Leu Ser
 65                 70                  75                  80

Ser Ala Ser Ile Gly Asn Val Ser Ser Val Gly Val Asp Ser Thr Leu
                85                  90                  95

Asn Val Val Gln Asp Ser Val Gly Gln Tyr Val Gly
            100                 105

<210> SEQ ID NO 16
<211> LENGTH: 98
<212> TYPE: PRT
<213> ORGANISM: Euprosthenops australis
```

<400> SEQUENCE: 16

```
Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Val Ser Ala Ser Ala Pro Gly Ala
        35                  40                  45

Ser Gly Cys Glu Val Ile Val Gln Ala Leu Leu Glu Val Ile Thr Ala
    50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly
```

<210> SEQ ID NO 17
<211> LENGTH: 1296
<212> TYPE: DNA
<213> ORGANISM: Artificial
<220> FEATURE:
<223> OTHER INFORMATION: Chimeric construct

<400> SEQUENCE: 17

```
cccatgggcc atcatcatca tcatcatatg agccatacca ccccgtggac caacccgggc      60
ctggcggaaa actttatgaa cagctttatg cagggcctga gcagcatgcc gggctttacc     120
gcgagccagc tggatgatat gagcaccatt gcgcagagca tggtgcagag cattcagagc     180
ctggcggcgc agggccgtac cagcccgaac aaactgcagg cgctgaacat ggcgtttgcg     240
agcagcatgg cggaaattgc ggcgagcgaa gaaggcggcg cagcctgag caccaaaacc      300
agcagcattg cgagcgcgat gagcaacgcg tttctgcaga ccaccggcgt ggtgaaccag     360
ccgtttatta cgaaaattac ccagctggtg agcatgtttg cgcaggcggg catgaacgat     420
gtgagcgcgg ggaattcggg acgaggtcaa ggaggatatg gtcaaggttc tggaggtaat     480
gctgctgccg cagccgctgc cgccgccgcc gccgctgcag cagccggaca gggaggtcaa     540
ggtggatatg gtagacaaag ccaaggtgct ggttccgctg ctgctgctgc tgctgctgct     600
gccgctgctg ctgctgcagg atctggacaa ggtggatacg gtggacaagg tcaaggaggt     660
tatggtcaga gtgggaattc gggacgaggt caaggaggat atggtcaagg ttctggaggt     720
aatgctgctg ccgcagccgc tgccgccgcc gccgccgctg cagcagccgg acagggaggt     780
caaggtggat atggtagaca agccaaggt gctggttccg ctgctgctgc tgctgctgct      840
gctgccgctg ctgctgctgc aggatctgga caaggtggat acgtggaca aggtcaagga      900
ggttatggtc agagtgggaa ttcggttaca tctggaggtt acggatatgg aaccagtgca     960
gctgcaggag ctggagttgc agcaggttca tatgcaggtg ctgtcaatcg cttgtctagt    1020
gctgaagctg ccagtagagt atcctctaat attgcagcta ttgcatctgg tggtgcttcc    1080
gccctcccca gtgttatttc aaatatttac tcaggtgtcg ttgcttctgg tgtttcttct    1140
aatgaagctc tgattcaagc tctgttggaa ctcctttccg cacttgttca tgtttaagc     1200
agtgcctcta tcggtaatgt tagctcagta ggagtagata gtacattgaa tgttgttcag    1260
gattcagtag gccaatatgt aggttaatga aagctt                              1296
```

-continued

```
<210> SEQ ID NO 18
<211> LENGTH: 427
<212> TYPE: PRT
<213> ORGANISM: Artificial
<220> FEATURE:
<223> OTHER INFORMATION: Chimeric sequence

<400> SEQUENCE: 18

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Ala Ala Gly Gln
                165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Ala Gly Ser Gly
        195                 200                 205

Gln Gly Gly Tyr Gly Gly Gln Gly Gln Gly Gly Tyr Gly Gln Ser Gly
    210                 215                 220

Asn Ser Gly Arg Gly Gln Gly Gly Tyr Gly Gln Gly Ser Gly Gly Asn
225                 230                 235                 240

Ala Ala Ala Ala Ala Ala Ala Ala Ala Ala Ala Ala Ala Ala Gly
                245                 250                 255

Gln Gly Gly Gln Gly Gly Tyr Gly Arg Gln Ser Gln Gly Ala Gly Ser
            260                 265                 270

Ala Ala Ala Ala Ala Ala Ala Ala Ala Ala Ala Ala Ala Gly Ser
        275                 280                 285

Gly Gln Gly Gly Tyr Gly Gly Gln Gly Gln Gly Gly Tyr Gly Gln Ser
    290                 295                 300

Gly Asn Ser Val Thr Ser Gly Gly Tyr Gly Tyr Gly Thr Ser Ala Ala
305                 310                 315                 320

Ala Gly Ala Gly Val Ala Ala Gly Ser Tyr Ala Gly Ala Val Asn Arg
                325                 330                 335

Leu Ser Ser Ala Glu Ala Ala Ser Arg Val Ser Ser Asn Ile Ala Ala
            340                 345                 350

Ile Ala Ser Gly Gly Ala Ser Ala Leu Pro Ser Val Ile Ser Asn Ile
        355                 360                 365
```

Tyr Ser Gly Val Val Ala Ser Gly Val Ser Ser Asn Glu Ala Leu Ile
            370                 375                 380

Gln Ala Leu Leu Glu Leu Leu Ser Ala Leu Val His Val Leu Ser Ser
385                 390                 395                 400

Ala Ser Ile Gly Asn Val Ser Ser Val Gly Val Asp Ser Thr Leu Asn
                405                 410                 415

Val Val Gln Asp Ser Val Gly Gln Tyr Val Gly
            420                 425

<210> SEQ ID NO 19
<211> LENGTH: 97
<212> TYPE: PRT
<213> ORGANISM: Parawixia bistriata

<400> SEQUENCE: 19

Gly Ala Gly Ala Ala Ala Ser Gly Ala Thr Gly Arg Val Ala Asn
1               5                   10                  15

Ser Leu Gly Ala Met Ala Ser Gly Gly Ile Asn Ala Leu Pro Gly Val
            20                  25                  30

Phe Ser Asn Ile Phe Ser Gln Val Ser Ala Ala Ser Gly Gly Ala Ser
            35                  40                  45

Gly Gly Ala Val Leu Val Gln Ala Leu Thr Glu Val Ile Ala Leu Leu
50                  55                  60

Leu His Ile Leu Ser Ser Ala Ser Ile Gly Asn Val Ser Ser Gln Gly
65                  70                  75                  80

Leu Glu Gly Ser Met Ala Ile Ala Gln Gln Ala Ile Gly Ala Tyr Ala
            85                  90                  95

Gly

<210> SEQ ID NO 20
<211> LENGTH: 88
<212> TYPE: PRT
<213> ORGANISM: Tetragnatha kauaiensis

<400> SEQUENCE: 20

Ser Leu Leu Ser Ser Pro Ala Ser Asn Ala Arg Ile Ser Ser Ala Val
1               5                   10                  15

Ser Ala Leu Ala Ser Gly Ala Ala Ser Gly Pro Gly Tyr Leu Ser Ser
            20                  25                  30

Val Ile Ser Asn Val Val Ser Gln Val Ser Ser Asn Ser Gly Gly Leu
            35                  40                  45

Val Gly Cys Asp Thr Leu Val Gln Ala Leu Leu Glu Ala Ala Ala Ala
50                  55                  60

Leu Val His Val Leu Ala Ser Ser Ser Gly Gly Gln Val Asn Leu Asn
65                  70                  75                  80

Thr Ala Gly Tyr Thr Ser Gln Leu
            85

<210> SEQ ID NO 21
<211> LENGTH: 93
<212> TYPE: PRT
<213> ORGANISM: Argiope trifasciata

<400> SEQUENCE: 21

Ala Ala Ala Ser Arg Leu Ser Ser Pro Gln Ala Ser Ser Arg Val Ser
1               5                   10                  15

Ser Ala Val Ser Thr Leu Val Ser Ser Gly Pro Thr Asn Pro Ala Ser
            20                  25                  30

-continued

Leu Ser Asn Ala Ile Ser Ser Val Val Ser Gln Val Ser Ala Ser Asn
            35                  40                  45

Pro Gly Leu Ser Gly Cys Asp Val Leu Val Gln Ala Leu Leu Glu Ile
 50                  55                  60

Val Ser Ala Leu Val His Ile Leu Gly Ser Ser Ile Gly Gln Ile
 65                  70                  75                  80

Asn Tyr Ala Ala Ser Ser Gln Tyr Ala Gln Met Val Gly
                85                  90

<210> SEQ ID NO 22
<211> LENGTH: 101
<212> TYPE: PRT
<213> ORGANISM: Nephila clavipes

<400> SEQUENCE: 22

Ser Ala Ala Ser Arg Leu Ser Ser Pro Glu Ala Ser Ser Arg Val Ser
 1               5                  10                  15

Ser Ala Val Ser Asn Leu Val Ser Ser Gly Pro Thr Asn Ser Ala Ala
                20                  25                  30

Leu Ser Ser Thr Ile Ser Asn Val Val Ser Gln Ile Gly Ala Ser Asn
            35                  40                  45

Pro Gly Leu Ser Gly Cys Asp Val Leu Val Gln Ala Leu Leu Glu Val
 50                  55                  60

Val Ser Ala Leu Ile His Ile Leu Gly Ser Ser Ile Gly Gln Val
 65                  70                  75                  80

Asn Tyr Gly Ser Ala Gly Gln Ala Thr Gln Ile Val Gly Gln Ser Ile
                85                  90                  95

Tyr Gln Ala Leu Gly
            100

<210> SEQ ID NO 23
<211> LENGTH: 101
<212> TYPE: PRT
<213> ORGANISM: Nephila clavipes

<400> SEQUENCE: 23

Ala Ala Ala Ser Arg Leu Ser Ser Pro Gln Ala Ser Ser Arg Val Ser
 1               5                  10                  15

Ser Ala Val Ser Asn Leu Val Ala Ser Gly Pro Thr Asn Ser Ala Ala
                20                  25                  30

Leu Ser Ser Thr Ile Ser Asn Val Val Ser Gln Ile Gly Ala Ser Asn
            35                  40                  45

Pro Gly Leu Ser Gly Cys Asp Val Leu Ile Gln Ala Leu Leu Glu Val
 50                  55                  60

Val Ser Ala Leu Ile His Ile Leu Gly Ser Ser Ile Gly Gln Val
 65                  70                  75                  80

Asn Tyr Gly Ser Ala Gly Gln Ala Thr Gln Ile Val Gly Gln Ser Val
                85                  90                  95

Tyr Gln Ala Leu Gly
            100

<210> SEQ ID NO 24
<211> LENGTH: 101
<212> TYPE: PRT
<213> ORGANISM: Latrodectus Hesperus

```
<400> SEQUENCE: 24

Ala Ala Ala Ser Ala Leu Ala Ala Pro Ala Thr Ser Ala Arg Ile Ser
1               5                   10                  15

Ser His Ala Ser Ala Leu Leu Ser Asn Gly Pro Thr Asn Pro Ala Ser
            20                  25                  30

Ile Ser Asn Val Ile Ser Asn Ala Val Ser Gln Ile Ser Ser Ser Asn
            35                  40                  45

Pro Gly Ala Ser Ala Cys Asp Val Leu Val Gln Ala Leu Leu Glu Leu
        50                  55                  60

Val Thr Ala Leu Leu Thr Ile Ile Gly Ser Ser Asn Ile Gly Ser Val
65                  70                  75                  80

Asn Tyr Asp Ser Ser Gly Gln Tyr Ala Gln Val Val Thr Gln Ser Val
                85                  90                  95

Gln Asn Ala Phe Ala
            100

<210> SEQ ID NO 25
<211> LENGTH: 101
<212> TYPE: PRT
<213> ORGANISM: Latrodectus Hesperus

<400> SEQUENCE: 25

Ser Ala Ala Ser Ala Leu Ser Ser Pro Thr Thr His Ala Arg Ile Ser
1               5                   10                  15

Ser His Ala Ser Thr Leu Leu Ser Ser Gly Pro Thr Asn Ala Ala Ala
            20                  25                  30

Leu Ser Asn Val Ile Ser Asn Ala Val Ser Gln Val Ser Ala Ser Asn
            35                  40                  45

Pro Gly Ser Ser Ser Cys Asp Val Leu Val Gln Ala Leu Leu Glu Ile
        50                  55                  60

Ile Thr Ala Leu Ile Ser Ile Leu Asp Ser Ser Ser Val Gly Gln Val
65                  70                  75                  80

Asn Tyr Gly Ser Ser Gly Gln Tyr Ala Gln Ile Val Gly Gln Ser Met
                85                  90                  95

Gln Gln Ala Met Gly
            100

<210> SEQ ID NO 26
<211> LENGTH: 101
<212> TYPE: PRT
<213> ORGANISM: Latrodectus geometricus

<400> SEQUENCE: 26

Pro Ala Ala

```
Asn Tyr Gly Ser Ser Gly Gln Tyr Ala Gln Met Val Ser Gln Ser Val
                85                  90                  95

Gln Asn Val Phe Gly
            100

<210> SEQ ID NO 27
<211> LENGTH: 101
<212> TYPE: PRT
<213> ORGANISM: Euprosthenops australis

<400> SEQUENCE: 27

Asn Ser Val Ser Arg Leu Ser Ser Pro Ser Ala Val Ser Arg Val Ser
1               5                   10                  15

Ser Ala Val Ser Ser Leu Val Ser Asn Gly Gln Val Asn Met Ala Ala
                20                  25                  30

Leu Pro Asn Ile Ile Ser Asn Ile Ser Ser Val Ser Ala Ser Ala
            35                  40                  45

Pro Gly Ala Ser Gly Cys Glu Val Ile Val Gln Ala Leu Leu Glu Val
        50                  55                  60

Ile Thr Ala Leu Val Gln Ile Val Ser Ser Ser Val Gly Tyr Ile
65                  70                  75                  80

Asn Pro Ser Ala Val Asn Gln Ile Thr Asn Val Val Ala Asn Ala Met
                85                  90                  95

Ala Gln Val Met Gly
            100

<210> SEQ ID NO 28
<211> LENGTH: 98
<212> TYPE: PRT
<213> ORGANISM: Nephila clavipes

<400> SEQUENCE: 28

Pro Gly Ser Pro Gly Gly Ala Tyr Tyr Pro Ser Ser Arg Val Pro Asp
1               5                   10                  15

Met Val Asn Gly Ile Met Ser Ala Met Gln Gly Ser Gly Phe Asn Tyr
                20                  25                  30

Gln Met Phe Gly Asn Met Leu Ser Gln Tyr Ser Ser Gly Ser Gly Thr
            35                  40                  45

Cys Asn Pro Asn Asn Val Asn Val Leu Met Asp Ala Leu Leu Ala Ala
        50                  55                  60

Leu His Cys Leu Ser Asn His Gly Ser Ser Phe Ala Pro Ser Pro
65                  70                  75                  80

Thr Pro Ala Ala Met Ser Ala Tyr Ser Asn Ser Val Gly Arg Met Phe
                85                  90                  95

Ala Tyr

<210> SEQ ID NO 29
<211> LENGTH: 98
<212> TYPE: PRT
<213> ORGANISM: Nephila inaurata madagascariensis

<400> SEQUENCE: 29

Gly Pro Gly Ser Gly Gly Ser Tyr Tyr Pro Ser Ser Arg Val Pro Asp
1               5                   10                  15

Met Val Asn Gly Ile Met Ser Ala Met Gln Gly Ser Gly Phe Asn Tyr
                20                  25                  30

Gln Met Phe Gly Asn Met Leu Ser Gln Tyr Ser Ser Gly Ser Gly Ser
            35                  40                  45
```

```
Cys Asn Pro Asn Asn Val Asn Val Leu Met Asp Ala Leu Ala Ala
        50                  55                  60

Leu His Cys Leu Ser Asn His Gly Ser Ser Phe Ala Pro Ser Pro
65                  70                  75                  80

Thr Pro Ala Ala Met Ser Ala Tyr Ser Asn Ser Val Gly Arg Met Phe
                    85                  90                  95

Ala Tyr

<210> SEQ ID NO 30
<211> LENGTH: 93
<212> TYPE: PRT
<213> ORGANISM: Latrodectus geometricus

<400> SEQUENCE: 30

Ser Ala Ala Ser Ala Leu Ser Ser Pro Thr Thr His Ala Arg Ile Ser
1               5                   10                  15

Ser His Ala Ser Thr Leu Leu Ser Ser Gly Pro Thr Asn Ser Ala Ala
                20                  25                  30

Ile Ser Asn Val Ile Ser Asn Ala Val Ser Gln Val Ser Ala Ser Asn
            35                  40                  45

Pro Gly Ser Ser Cys Asp Val Leu Val Gln Ala Leu Leu Glu Leu
    50                  55                  60

Ile Thr Ala Leu Ile Ser Ile Val Asp Ser Ser Asn Ile Gly Gln Val
65                  70                  75                  80

Asn Tyr Gly Ser Ser Gly Gln Tyr Ala Gln Met Val Gly
                85                  90

<210> SEQ ID NO 31
<211> LENGTH: 101
<212> TYPE: PRT
<213> ORGANISM: Latrodectus geometricus

<400> SEQUENCE: 31

Ala Ala Ala Ser Ala Leu Ala Ala Pro Ala Thr Ser Ala Arg Ile Ser
1               5                   10                  15

Ser His Ala Ser Thr Leu Leu Ser Asn Gly Pro Thr Asn Pro Ala Ser
                20                  25                  30

Ile Ser Asn Val Ile Ser Asn Ala Val Ser Gln Ile Ser Ser Ser Asn
            35                  40                  45

Pro Gly Ala Ser Ser Cys Asp Val Leu Val Gln Ala Leu Leu Glu Leu
    50                  55                  60

Val Thr Ala Leu Leu Thr Ile Ile Gly Ser Ser Asn Val Gly Asn Val
65                  70                  75                  80

Asn Tyr Asp Ser Ser Gly Gln Tyr Ala Gln Val Val Ser Gln Ser Val
                85                  90                  95

Gln Asn Ala Phe Val
            100

<210> SEQ ID NO 32
<211> LENGTH: 96
<212> TYPE: PRT
<213> ORGANISM: Araneus diadematus

<400> SEQUENCE: 32

Gly Ala Val Asn Arg Leu Ser Ser Ala Gly Ala Ala Ser Arg Val Ser
1               5                   10                  15

Ser Asn Val Ala Ala Ile Ala Ser Ala Gly Ala Ala Ala Leu Pro Asn
                20                  25                  30
```

```
Val Ile Ser Asn Ile Tyr Ser Gly Val Leu Ser Ser Gly Val Ser Ser
        35                  40                  45

Ser Glu Ala Leu Ile Gln Ala Leu Leu Glu Val Ile Ser Ala Leu Ile
50                  55                  60

His Val Leu Gly Ser Ala Ser Ile Gly Asn Val Ser Ser Val Gly Val
65                  70                  75                  80

Asn Ser Ala Leu Asn Ala Val Gln Asn Ala Val Gly Ala Tyr Ala Gly
                85                  90                  95

<210> SEQ ID NO 33
<211> LENGTH: 99
<212> TYPE: PRT
<213> ORGANISM: Argiope trifasciata

<400> SEQUENCE: 33

Ser Arg Leu Ser Ser Pro Gly Ala Ala Ser Arg Val Ser Ser Ala Val
1               5                   10                  15

Thr Ser Leu Val Ser Ser Gly Pro Thr Asn Ser Ala Ala Leu Ser
            20                  25                  30

Asn Thr Ile Ser Asn Val Val Ser Gln Ile Ser Ser Asn Pro Gly
        35                  40                  45

Leu Ser Gly Cys Asp Val Leu Val Gln Ala Leu Leu Glu Ile Val Ser
50                  55                  60

Ala Leu Val His Ile Leu Gly Ser Ala Asn Ile Gly Gln Val Asn Ser
65                  70                  75                  80

Ser Gly Val Gly Arg Ser Ala Ser Ile Val Gly Gln Ser Ile Asn Gln
                85                  90                  95

Ala Phe Ser

<210> SEQ ID NO 34
<211> LENGTH: 89
<212> TYPE: PRT
<213> ORGANISM: Cyrtophora moluccensis

<400> SEQUENCE: 34

Ser His Leu Ser Ser Pro Glu Ala Ser Ser Arg Val Ser Ser Ala Val
1               5                   10                  15

Ser Asn Leu Val Ser Ser Gly Ser Thr Asn Ser Ala Ala Leu Pro Asn
            20                  25                  30

Thr Ile Ser Asn Val Val Ser Gln Ile Ser Ser Asn Pro Gly Leu
        35                  40                  45

Ser Gly Cys Asp Val Leu Val Gln Ala Leu Leu Glu Val Val Ser Ala
50                  55                  60

Leu Ile His Ile Leu Gly Ser Ser Ser Ile Gly Gln Val Asn Tyr Gly
65                  70                  75                  80

Ser Ala Gly Gln Ala Thr Gln Ile Val
                85

<210> SEQ ID NO 35
<211> LENGTH: 87
<212> TYPE: PRT
<213> ORGANISM: Nephila inaurata madagascariensis

<400> SEQUENCE: 35

Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
            20                  25                  30
```

```
Thr Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln
                85
```

<210> SEQ ID NO 36
<211> LENGTH: 97
<212> TYPE: PRT
<213> ORGANISM: Argiope amoena

<400> SEQUENCE: 36

```
Arg Leu Ser Ser Pro Gln Ala Ser Ser Arg Val Ser Ser Ala Val Ser
 1               5                  10                  15

Thr Leu Val Ser Ser Gly Pro Thr Asn Pro Ala Ser Leu Ser Asn Ala
            20                  25                  30

Ile Gly Ser Val Val Ser Gln Val Ala Ser Asn Pro Gly Leu Pro
            35                  40                  45

Ser Cys Asp Val Leu Val Gln Ala Leu Leu Glu Ile Val Ser Ala Leu
 50                  55                  60

Val His Ile Leu Gly Ser Ser Ile Gly Gln Ile Asn Tyr Ser Ala
 65                  70                  75                  80

Ser Ser Gln Tyr Ala Arg Leu Val Gly Gln Ser Ile Ala Gln Ala Leu
                85                  90                  95

Gly
```

<210> SEQ ID NO 37
<211> LENGTH: 82
<212> TYPE: PRT
<213> ORGANISM: Argiope aurantia

<400> SEQUENCE: 37

```
Ser Arg Leu Ser Ser Pro Gln Ala Ser Ser Arg Val Ser Ser Ala Val
 1               5                  10                  15

Ser Thr Leu Val Ser Ser Gly Pro Thr Asn Pro Ala Ala Leu Ser Asn
            20                  25                  30

Ala Ile Ser Ser Val Val Ser Gln Val Ser Ala Ser Asn Pro Gly Leu
            35                  40                  45

Ser Gly Cys Asp Val Leu Val Gln Ala Leu Leu Glu Leu Val Ser Ala
 50                  55                  60

Leu Val His Ile Leu Gly Ser Ser Ile Gly Gln Ile Asn Tyr Ala
 65                  70                  75                  80

Ala Ser
```

<210> SEQ ID NO 38
<211> LENGTH: 98
<212> TYPE: PRT
<213> ORGANISM: Argiope trifasciata

<400> SEQUENCE: 38

```
Ser Arg Leu Ser Ser Pro Gln Ala Ser Ser Arg Val Ser Ser Ala Val
 1               5                  10                  15

Ser Thr Leu Val Ser Ser Gly Pro Thr Asn Pro Ala Ser Leu Ser Asn
            20                  25                  30
```

-continued

Ala Ile Ser Ser Val Val Ser Gln Val Ser Ser Asn Pro Gly Leu
            35                  40                  45

Ser Gly Cys Asp Val Leu Val Gln Ala Leu Leu Glu Ile Val Ser Ala
        50                  55                  60

Leu Val His Ile Leu Gly Ser Ser Ile Gly Gln Ile Asn Tyr Ala
65                  70                  75                  80

Ala Ser Ser Gln Tyr Ala Gln Leu Val Gly Gln Ser Leu Thr Gln Ala
            85                  90                  95

Leu Gly

<210> SEQ ID NO 39
<211> LENGTH: 89
<212> TYPE: PRT
<213> ORGANISM: Gasteracantha mammosa

<400> SEQUENCE: 39

Ser Arg Leu Ser Ser Pro Gln Ala Gly Ala Arg Val Ser Ser Ala Val
1               5                   10                  15

Ser Ala Leu Val Ala Ser Gly Pro Thr Ser Pro Ala Ala Val Ser Ser
            20                  25                  30

Ala Ile Ser Asn Val Ala Ser Gln Ile Ser Ala Ser Asn Pro Gly Leu
            35                  40                  45

Ser Gly Cys Asp Val Leu Val Gln Ala Leu Leu Glu Ile Val Ser Ala
        50                  55                  60

Leu Val Ser Ile Leu Ser Ser Ala Ser Ile Gly Gln Ile Asn Tyr Gly
65                  70                  75                  80

Ala Ser Gly Gln Tyr Ala Ala Met Ile
            85

<210> SEQ ID NO 40
<211> LENGTH: 98
<212> TYPE: PRT
<213> ORGANISM: Araneus diadematus

<400> SEQUENCE: 40

Ser Arg Leu Ser Ser Pro Ser Ala Ala Ala Arg Val Ser Ser Ala Val
1               5                   10                  15

Ser Leu Val Ser Asn Gly Gly Pro Thr Ser Pro Ala Ala Leu Ser Ser
            20                  25                  30

Ser Ile Ser Asn Val Val Ser Gln Ile Ser Ala Ser Asn Pro Gly Leu
            35                  40                  45

Ser Gly Cys Asp Ile Leu Val Gln Ala Leu Leu Glu Ile Ile Ser Ala
        50                  55                  60

Leu Val His Ile Leu Gly Ser Ala Asn Ile Gly Pro Val Asn Ser Ser
65                  70                  75                  80

Ser Ala Gly Gln Ser Ala Ser Ile Val Gly Gln Ser Val Tyr Arg Ala
            85                  90                  95

Leu Ser

<210> SEQ ID NO 41
<211> LENGTH: 98
<212> TYPE: PRT
<213> ORGANISM: Araneus diadematus

```
<400> SEQUENCE: 41

Ser Arg Leu Ser Ser Pro Ala Ala Ser Ser Arg Val Ser Ser Ala Val
1               5                   10                  15

Ser Ser Leu Val Ser Ser Gly Pro Thr Lys His Ala Ala Leu Ser Asn
            20                  25                  30

Thr Ile Ser Ser Val Val Ser Gln Val Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val Ser Ile Leu Gly Ser Ser Ile Gly Gln Ile Asn Tyr Gly
65                  70                  75                  80

Ala Ser Ala Gln Tyr Thr Gln Met Val Gly Gln Ser Val Ala Gln Ala
                85                  90                  95

Leu Ala

<210> SEQ ID NO 42
<211> LENGTH: 100
<212> TYPE: PRT
<213> ORGANISM: Deinopis spinosa

<400> SEQUENCE: 42

Ser Ala Val Ser Arg Met Ser Thr Pro Gly Ser Gly Ser Arg Ile Ser
1               5                   10                  15

Asn Ala Val Ser Asn Ile Leu Ser Ser Gly Val Ser Ser Ser Ser Gly
            20                  25                  30

Leu Ser Asn Ala Ile Ser Asn Ile Ser Ser Ser Ile Ser Ala Ser Asn
        35                  40                  45

Pro Gly Leu Ser Gly Cys Asp Val Leu Val Gln Val Leu Leu Glu Val
    50                  55                  60

Ile Ser Ala Leu Val His Ile Leu Gly Ser Ala Ser Val Gly Gln Val
65                  70                  75                  80

Gly Ser Ser Pro Gln Asn Ala Gln Met Val Ala Ala Asn Ala Val Ala
                85                  90                  95

Asn Ala Phe Ser
            100

<210> SEQ ID NO 43
<211> LENGTH: 100
<212> TYPE: PRT
<213> ORGANISM: Deinopis spinosa

<400> SEQUENCE: 43

Ser Ala Val Ser Arg Met Ser Thr Pro Gly Ser Gly Ser Arg Ile Ser
1               5                   10                  15

Asn Ala Val Ser Asn Ile Leu Ser Ser Gly Val Ser Ser Ser Ser Gly
            20                  25                  30

Leu Ser Asn Val Ile Ser Asn Leu Ser Ser Ser Ile Ser Thr Ser Asn
        35                  40                  45

Pro Gly Leu Ser Gly Cys Asp Val Leu Val Gln Val Leu Leu Glu Val
    50                  55                  60

Ile Ser Ala Leu Val His Ile Leu Ser Ser Ala Ser Leu Gly Gln Val
65                  70                  75                  80

Gly Ser Ser Pro Gln Asn Ala Gln Met Val Ala Ala Asn Ala Val Ala
                85                  90                  95

Asn Ala Phe Ser
            100
```

-continued

```
<210> SEQ ID NO 44
<211> LENGTH: 96
<212> TYPE: PRT
<213> ORGANISM: Metepeira grandiosa

<400> SEQUENCE: 44

Gly Ala Val Asn Arg Leu Ser Ser Ala Glu Ala Ser Arg Val Ser
1               5                   10                  15

Ser Asn Val Ala Ala Leu Ala Ser Gly Gly Pro Ala Ala Leu Ala Asn
            20                  25                  30

Val Met Gly Asn Ile Tyr Ser Gly Val Ala Ser Ser Gly Val Ser Ser
            35                  40                  45

Gly Glu Ala Leu Val Gln Ala Leu Leu Glu Val Ile Ser Ala Leu Val
        50                  55                  60

His Leu Leu Ser Asn Ala Ser Ile Gly Asn Val Ser Ser Ala Gly Leu
65                  70                  75                  80

Gly Asn Thr Met Ser Leu Val Gln Ser Thr Val Gly Ala Tyr Ala Gly
                85                  90                  95

<210> SEQ ID NO 45
<211> LENGTH: 101
<212> TYPE: PRT
<213> ORGANISM: Latrodectus hesperus

<400> SEQUENCE: 45

Ser Ala Ala Ser Arg Leu Ser Ser Pro Ser Ser Ser Arg Ile Ser
1               5                   10                  15

Ser Ala Ala Ser Ser Leu Ala Thr Gly Gly Val Leu Asn Ser Ala Ala
            20                  25                  30

Leu Pro Ser Val Val Ser Asn Met Met Ser Gln Val Ser Ala Ser Ser
            35                  40                  45

Pro Gly Met Ser Ser Glu Val Val Ile Gln Ala Leu Leu Glu Leu
        50                  55                  60

Val Ser Ser Leu Ile His Ile Leu Ser Ser Ala Asn Ile Gly Gln Val
65                  70                  75                  80

Asp Phe Asn Ser Val Gly Asn Thr Ala Ala Val Val Gly Gln Ser Leu
                85                  90                  95

Gly Ala Ala Leu Gly
            100

<210> SEQ ID NO 46
<211> LENGTH: 100
<212> TYPE: PRT
<213> ORGANISM: Nephila clavipes

<400> SEQUENCE: 46

Ala Ala Ala Ser Arg Leu Ala Ser Pro Asp Ser Gly Ala Arg Val Ala
1               5                   10                  15

Ser Ala Val Ser Asn Leu Val Ser Ser Gly Pro Thr Ser Ser Ala Ala
            20                  25                  30

Leu Ser Ser Val Ile Ser Asn Ala Val Ser Gln Ile Gly Ala Ser Asn
            35                  40                  45

Pro Gly Leu Ser Gly Cys Asp Val Leu Ile Gln Ala Leu Leu Glu Ile
        50                  55                  60

Val Ser Ala Cys Val Thr Ile Leu Ser Ser Ser Ser Ile Gly Gln Val
65                  70                  75                  80
```

-continued

```
Asn Tyr Gly Ala Ala Ser Gln Phe Ala Gln Val Val Gly Gln Ser Val
                85                  90                  95

Leu Ser Ala Phe
            100

<210> SEQ ID NO 47
<211> LENGTH: 85
<212> TYPE: PRT
<213> ORGANISM: Nephila inaurata madagascariensis

<400> SEQUENCE: 47

Ala Ala Ala Ser Arg Leu Ala Ser Pro Asp Ser Gly Ala Arg Val Ala
1               5                   10                  15

Ser Ala Val Ser Asn Leu Val Ser Ser Gly Pro Thr Ser Ser Ala Ala
                20                  25                  30

Leu Ser Ser Val Ile Ser Asn Ala Val Ser Gln Ile Gly Ala Ser Asn
            35                  40                  45

Pro Gly Leu Ser Gly Cys Asp Val Leu Ile Gln Ala Leu Leu Glu Ile
    50                  55                  60

Val Ser Ala Cys Val Thr Ile Leu Ser Ser Ser Ile Gly Gln Val
65                  70                  75                  80

Asn Tyr Gly Ala Ala
                85

<210> SEQ ID NO 48
<211> LENGTH: 101
<212> TYPE: PRT
<213> ORGANISM: Latrodectus hesperus

<400> SEQUENCE: 48

Ser Ala Ala Ser Arg Leu Ser Ser Pro Ser Ser Ser Arg Ile Ser
1               5                   10                  15

Ser Ala Ala Ser Ser Leu Ala Thr Gly Gly Val Leu Asn Ser Ala Ala
                20                  25                  30

Leu Pro Ser Val Val Ser Asn Ile Met Ser Gln Val Ser Ala Ser Ser
            35                  40                  45

Pro Gly Met Ser Ser Glu Val Val Ile Gln Ala Leu Leu Glu Leu
    50                  55                  60

Val Ser Ser Leu Ile His Ile Leu Ser Ser Ala Asn Ile Gly Gln Val
65                  70                  75                  80

Asp Phe Asn Ser Val Gly Asn Thr Ala Ala Val Val Gly Gln Ser Leu
                85                  90                  95

Gly Ala Ala Leu Gly
            100

<210> SEQ ID NO 49
<211> LENGTH: 100
<212> TYPE: PRT
<213> ORGANISM: Artificial
<220> FEATURE:
<223> OTHER INFORMATION: Consensus sequence

<400> SEQUENCE: 49

Ser Arg Leu Ser Ser Pro Gln Ala Ser Ser Arg Val Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ala Ser Asn Pro Gly Leu
            35                  40                  45
```

```
Ser Gly Cys Asp Val Leu Val Gln Ala Leu Leu Glu Val Val Ser Ala
 50                  55                  60

Leu Val His Ile Leu Gly Ser Ser Ile Gly Gln Val Asn Tyr Gly
 65                  70                  75                  80

Ser Ala Gly Gln Ala Thr Gln Ile Val Gly Gln Ser Val Ala Gln Ala
                 85                  90                  95

Leu Gly Glu Phe
            100

<210> SEQ ID NO 50
<211> LENGTH: 93
<212> TYPE: PRT
<213> ORGANISM: Macrothele holsti

<400> SEQUENCE: 50

Ser His Leu Ser Ser Pro Glu Ala Ser Ser Arg Val Ser Ala Val
 1               5                  10                  15

Ser Asn Leu Val Ser Gly Gly Ser Thr Asn Ser Ala Ala Leu Pro Asn
                 20                  25                  30

Thr Ile Ser Asn Val Val Ser Gln Ile Ser Ser Asn Pro Gly Leu
             35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asp Tyr Gly
 65                  70                  75                  80

Ser Ala Gly Gln Ala Thr Gln Ile Val Gly Gln Ser Ala
                 85                  90

<210> SEQ ID NO 51
<211> LENGTH: 89
<212> TYPE: PRT
<213> ORGANISM: Nephila pilipes

<400> SEQUENCE: 51

Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Asn
                 20                  25                  30

Thr Ile Ser Asn Val Val Ser Gln Ile Ser Ser Asn Pro Gly Leu
             35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln Ile Val
                 85

<210> SEQ ID NO 52
<211> LENGTH: 89
<212> TYPE: PRT
<213> ORGANISM: Octonoba varians

<400> SEQUENCE: 52

Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Asn
                 20                  25                  30
```

```
Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
 50                  55                  60

Pro Ile His Ile Leu Gly Ser Ser Ile Gly Gln Val Asn Tyr Gly
 65                  70                  75                  80

Ser Ala Gly Gln Ala Thr Gln Ile Val
                    85

<210> SEQ ID NO 53
<211> LENGTH: 89
<212> TYPE: PRT
<213> ORGANISM: Psechrus sinensis

<400> SEQUENCE: 53

Ser Arg Leu Ser Ser Pro Glu Ala Ser Ser Arg Val Ser Ala Val
 1               5                  10                  15

Ser Asn Leu Val Ser Ser Gly Pro Thr Asn Ser Ala Ala Leu Pro Asn
                 20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln Ile Val
                    85

<210> SEQ ID NO 54
<211> LENGTH: 88
<212> TYPE: PRT
<213> ORGANISM: Tetragnatha versicolor

<400> SEQUENCE: 54

Ser Arg Leu Ser Ser Pro Ala Ser Asn Ala Arg Ile Ser Ser Ala Val
 1               5                  10                  15

Ser Ala Leu Ala Ser Gly Gly Ala Ser Ser Pro Gly Tyr Leu Ser Ser
                 20                  25                  30

Ile Ile Ser Asn Val Val Ser Gln Val Ser Ser Asn Asn Asp Gly Leu
            35                  40                  45

Ser Gly Cys Asp Thr Val Val Gln Ala Leu Leu Glu Val Ala Ala Ala
 50                  55                  60

Leu Val His Val Leu Ala Ser Ser Asn Ile Gly Gln Val Asn Leu Asn
 65                  70                  75                  80

Thr Ala Gly Tyr Thr Ser Gln Leu
                    85

<210> SEQ ID NO 55
<211> LENGTH: 82
<212> TYPE: PRT
<213> ORGANISM: Nephila senegalensis
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
```

```
<400> SEQUENCE: 55

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
                20                  25                  30

Val Ile Xaa Asn Ala Val Ser Gln Ile Gly Ala Ser Asn Pro Gly Leu
            35                  40                  45

Ser Gly Cys Asp Val Leu Ile Xaa Ala Leu Leu Glu Ile Val Ser Ala
        50                  55                  60

Cys Val Thr Ile Leu Ser Ser Ser Ile Gly Gln Val Asn Tyr Gly
65                  70                  75                  80

Ala Ala

<210> SEQ ID NO 56
<211> LENGTH: 94
<212> TYPE: PRT
<213> ORGANISM: Araneus diadematus

<400> SEQUENCE: 56

Ser Val Tyr Leu Arg Leu Gln Pro Arg Leu Glu Val Ser Ser Ala Val
1               5                   10                  15

Ser Ser Leu Val Ser Ser Gly Pro Thr Asn Gly Ala Ala Val Ser Gly
                20                  25                  30

Ala Leu Asn Ser Leu Val Ser Gln Ile Ser Ala Ser Asn Pro Gly Leu
            35                  40                  45

Ser Gly Cys Asp Ala Leu Val Gln Ala Leu Leu Glu Leu Val Ser Ala
        50                  55                  60

Leu Val Ala Ile Leu Ser Ser Ala Ser Ile Gly Gln Val Asn Val Ser
65                  70                  75                  80

Ser Val Ser Gln Ser Thr Gln Met Ile Ser Gln Ala Leu Ser
                85                  90

<210> SEQ ID NO 57
<211> LENGTH: 99
<212> TYPE: PRT
<213> ORGANISM: Agelenopsis aperta

<400> SEQUENCE: 57

Asn Ser Val Ser Arg Leu Ser Ser Pro Ser Ser Ser Arg Val Ser
1               5                   10                  15

Ser Ala Val Ser Gly Leu Leu Pro Asn Gly Asn Phe Asn Leu Gly Asn
                20                  25                  30

Leu Pro Gly Ile Val Ser Asn Leu Ser Ser Ser Ile Ala Ser Ser Gly
            35                  40                  45

Leu Ser Gly Cys Glu Asn Leu Val Gln Val Leu Ile Glu Val Val Ser
        50                  55                  60

Ala Leu Val His Ile Leu Gly Ser Ala Asn Ile Gly Asn Ile Asn Met
65                  70                  75                  80

Asn Ala Ala Ser Ser Thr Ala Ala Val Gly Gln Ala Ile Val Asn
                85                  90                  95

Gly Leu Tyr

<210> SEQ ID NO 58
<211> LENGTH: 102
<212> TYPE: PRT
<213> ORGANISM: Argiope argentata
```

<400> SEQUENCE: 58

Ala Ser Ser Ser Gly Leu Gly Ser Ser Ala Ser Ala Arg Val Ser
1               5                   10                  15

Ser Leu Ala Asn Ser Val Ala Ser Ala Ile Ser Ser Ser Gly Gly Ser
            20                  25                  30

Leu Ser Val Pro Thr Phe Leu Asn Phe Leu Ser Ser Val Gly Ala Gln
            35                  40                  45

Val Ser Ser Ser Ser Leu Asn Ser Ser Glu Val Thr Asn Glu Val
    50                  55                  60

Leu Leu Glu Ala Ile Ala Ala Leu Leu Gln Val Leu Asn Gly Ala Gln
65                  70                  75                  80

Ile Thr Ser Val Asn Leu Arg Asn Val Pro Asn Ala Gln Gln Ala Leu
                85                  90                  95

Val Gln Ala Leu Ser Gly
                100

<210> SEQ ID NO 59
<211> LENGTH: 100
<212> TYPE: PRT
<213> ORGANISM: Artificial
<220> FEATURE:
<223> OTHER INFORMATION: Artificial construct

<400> SEQUENCE: 59

Ser Arg Leu Ser Ser Pro Glu Ala Ser Arg Val Ser Ser Ala Val
1               5                   10                  15

Ser Asn Leu Val Ser Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
            35                  40                  45

Ser Gly Cys Asp Val Leu Val Gln Ala Leu Leu Glu Val Val Ser Ala
            50                  55                  60

Leu Ile His Ile Leu Gly Ser Ser Ile Gly Gln Val Asn Tyr Gly
65                  70                  75                  80

Ser Ala Gly Gln Ala Thr Gln Leu Val Gly Gln Ser Val Tyr Gln Ala
                85                  90                  95

Leu Gly Glu Phe
                100

<210> SEQ ID NO 60
<211> LENGTH: 87
<212> TYPE: PRT
<213> ORGANISM: Nephila senegalensis

<400> SEQUENCE: 60

Ser Arg Leu Ser Ser Pro Glu Ala Ser Arg Val Ser Ser Ala Val
1               5                   10                  15

Ser Asn Leu Val Ser Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
            50                  55                  60

Leu Val His Ile Leu Gly Ser Ser Ile Gly Gln Val Asn Tyr Gly
65                  70                  75                  80

Ser Ala Gly Gln Ala Thr Gln
                85

<210> SEQ ID NO 61
<211> LENGTH: 97
<212> TYPE: PRT
<213> ORGANISM: Dolomedes tenebrosus

<400> SEQUENCE: 61

Ser Arg Leu Ser Ser Pro Gln Ala Ala Ser Arg Val Ser Ser Ala Val
1               5                   10                  15

Ser Ser Leu Val Ser Asn Gly Gln Val Asn Val Ala Ala Leu Pro Ser
            20                  25                  30

Ile Ile Ser Ser Leu Ser Ser Ser Ile Ser Ala Ser Ser Thr Ala Ala
        35                  40                  45

Ser Asp Cys Glu Val Leu Val Gln Val Leu Leu Glu Ile Val Ser Ala
50                  55                  60

Leu Val Gln Ile Val Ser Ser Ala Asn Val Gly Tyr Ile Asn Pro Glu
65                  70                  75                  80

Ala Ser Gly Ser Leu Asn Ala Val Gly Ser Ala Leu Ala Ala Ala Met
                85                  90                  95

Gly

<210> SEQ ID NO 62
<211> LENGTH: 100
<212> TYPE: PRT
<213> ORGANISM: Uloborus diversus

<400> SEQUENCE: 62

Ala Ala Ser Asn Arg Ile Val Ser Ala Pro Ala Val Asn Arg Met Ser
1               5                   10                  15

Ala Ala Ser Ser Thr Leu Val Ser Asn Gly Ala Phe Asn Val Gly Ala
            20                  25                  30

Leu Gly Ser Thr Ile Ser Asp Met Ala Ala Gln Ile Gln Ala Gly Ser
        35                  40                  45

Gln Gly Leu Ser Ser Ala Glu Ala Thr Val Gln Ala Leu Leu Glu Val
    50                  55                  60

Ile Ser Val Leu Thr His Met Leu Ser Ser Ala Asn Ile Gly Tyr Val
65                  70                  75                  80

Asp Phe Ser Arg Val Gly Asp Ser Ala Ser Ala Val Ser Gln Ser Met
                85                  90                  95

Ala Tyr Ala Gly
            100

<210> SEQ ID NO 63
<211> LENGTH: 102
<212> TYPE: PRT
<213> ORGANISM: Argiope bruennichi

<400> SEQUENCE: 63

Val Ser Ser Ser Gly Leu Gly Ser Ser Ala Ala Thr Ala Arg Val Ser
1               5                   10                  15

Ser Leu Ala Asn Ser Phe Ala Ser Ala Ile Ser Ser Ser Gly Gly Ser
            20                  25                  30

Leu Ser Val Pro Thr Phe Leu Asn Leu Leu Ser Ser Val Gly Ala Gln
        35                  40                  45

Val Ser Ser Ser Ser Ser Leu Ser Ser Leu Glu Val Thr Asn Glu Val
    50                  55                  60

Leu Leu Glu Ala Ile Ala Ala Leu Leu Gln Val Ile Asn Gly Gly Ser
65                  70                  75                  80

```
Ile Thr Ser Val Asp Leu Arg Tyr Val Pro Asn Ala Gln Gln Asp Leu
                85                  90                  95

Val Asn Ala Leu Ser Gly
            100

<210> SEQ ID NO 64
<211> LENGTH: 96
<212> TYPE: PRT
<213> ORGANISM: Araneus ventricosus

<400> SEQUENCE: 64

Gly Ala Val Asn Arg Leu Ser Ser Ala Glu Ala Ala Ser Arg Val Ser
1               5                   10                  15

Ser Asn Ile Ala Ala Ile Ala Ser Gly Gly Ala Ser Ala Leu Pro Ser
            20                  25                  30

Val Ile Ser Asn Ile Tyr Ser Gly Val Ala Ser Gly Val Ser Ser
        35                  40                  45

Asn Glu Ala Leu Ile Gln Ala Leu Leu Glu Leu Leu Ser Ala Leu Val
        50                  55                  60

His Val Leu Ser Ser Ala Ser Ile Gly Asn Val Ser Ser Val Gly Val
65                  70                  75                  80

Asp Ser Thr Leu Asn Val Val Gln Asp Ser Val Gly Gln Tyr Val Gly
                85                  90                  95

<210> SEQ ID NO 65
<211> LENGTH: 101
<212> TYPE: PRT
<213> ORGANISM: Nephila clavipes

<400> SEQUENCE: 65

Ser Thr Thr Ser Arg Leu Ser Ser Ala Glu Ala Ser Ser Arg Ile Ser
1               5                   10                  15

Ser Ala Ala Ser Thr Leu Val Ser Gly Gly Tyr Leu Asn Thr Ala Ala
            20                  25                  30

Leu Pro Ser Val Ile Ser Asp Leu Phe Ala Gln Val Gly Ala Ser Ser
        35                  40                  45

Pro Gly Val Ser Asp Ser Glu Val Leu Ile Gln Val Leu Leu Glu Ile
        50                  55                  60

Val Ser Ser Leu Ile His Ile Leu Ser Ser Ser Ser Val Gly Gln Val
65                  70                  75                  80

Asp Phe Ser Ser Val Gly Ser Ser Ala Ala Ala Val Gly Gln Ser Met
                85                  90                  95

Gln Val Val Met Gly
            100

<210> SEQ ID NO 66
<211> LENGTH: 71
<212> TYPE: PRT
<213> ORGANISM: Dolomedes tenebrosus

<400> SEQUENCE: 66

Ser Arg Leu Ser Ser Pro Glu Ala Ala Ser Arg Val Ser Ala Val
1               5                   10                  15

Ser Ser Leu Val Ser Asn Gly Gln Val Asn Val Asp Ala Leu Pro Ser
            20                  25                  30

Ile Ile Ser Asn Leu Ser Ser Ser Ile Ser Ala Ser Ala Thr Thr Ala
        35                  40                  45
```

```
Ser Asp Cys Glu Val Leu Val Gln Val Leu Leu Glu Val Val Ser Ala
 50                  55                  60

Leu Val Gln Ile Val Cys Ser
 65                  70

<210> SEQ ID NO 67
<211> LENGTH: 102
<212> TYPE: PRT
<213> ORGANISM: Agelenopsis aperta

<400> SEQUENCE: 67

Ser Ser Glu Thr Gly Leu Ser Ser Ala Ser Ala Ser Ser Arg Val Asn
 1               5                  10                  15

Ser Leu Ala Ser Ser Val Ala Ser Ala Ile Ala Ser Gly Gln Ala Leu
                20                  25                  30

Ser Ala Asp Ser Phe Ala Lys Ser Leu Leu Ile Gln Ala Ser Gln Ile
            35                  40                  45

Gln Ser Ser Ala Pro Ser Phe Lys Ala Asp Asp Val Val His Glu Ser
 50                  55                  60

Leu Leu Glu Gly Ile Ser Ala Leu Ile Gln Val Ile Asn Ser Ser Tyr
 65                  70                  75                  80

Gly Ser Pro Leu Ser Leu Ser Asn Ala Gln Thr Val Asn Ala Gly Leu
                85                  90                  95

Val Asn Tyr Phe Leu Val
            100

<210> SEQ ID NO 68
<211> LENGTH: 102
<212> TYPE: PRT
<213> ORGANISM: Nephila clavata

<400> SEQUENCE: 68

Leu Ser Ser Ser Gly Leu Ser Ser Ala Ser Ala Ser Ala Arg Val Gly
 1               5                  10                  15

Ser Leu Ala Gln Ser Leu Ala Ser Ala Leu Ser Thr Ser Arg Gly Thr
                20                  25                  30

Leu Ser Leu Ser Thr Phe Leu Asn Leu Leu Ser Pro Ile Ser Ser Glu
            35                  40                  45

Ile Arg Ala Asn Thr Ser Leu Asp Gly Thr Gln Ala Thr Val Glu Ala
 50                  55                  60

Leu Leu Glu Ala Leu Ala Ala Leu Leu Gln Val Ile Asn Gly Ala Gln
 65                  70                  75                  80

Ile Thr Asp Val Asn Val Ser Ser Val Pro Ser Val Asn Ala Ala Leu
                85                  90                  95

Ala Ser Ala Leu Val Ala
            100

<210> SEQ ID NO 69
<211> LENGTH: 104
<212> TYPE: PRT
<213> ORGANISM: Latrodectus hesperus

<400> SEQUENCE: 69

Leu Ser Pro Ala Gly Leu Ala Ser Thr Ala Ala Thr Ser Arg Ile Asn
 1               5                  10                  15

Asp Ile Ala Gln Ser Leu Ser Ser Thr Leu Ser Ser Gly Ser Gln Leu
                20                  25                  30
```

```
Ala Pro Asp Asn Val Leu Pro Gly Leu Ile Gln Leu Ser Ser Ser Ile
        35                  40                  45

Gln Ser Gly Asn Pro Asp Leu Asp Pro Ala Gly Val Leu Ile Glu Ser
 50                  55                  60

Leu Leu Glu Tyr Thr Ser Ala Leu Leu Ala Leu Leu Gln Asn Ala Gln
 65                  70                  75                  80

Ile Thr Thr Tyr Asp Ala Ala Thr Leu Pro Ala Phe Asn Thr Ala Leu
                 85                  90                  95

Val Asn Tyr Leu Val Pro Leu Val
             100

<210> SEQ ID NO 70
<211> LENGTH: 95
<212> TYPE: PRT
<213> ORGANISM: Argiope argentata

<400> SEQUENCE: 70

Ser Val Ser Arg Leu Ser Ser Ala Glu Ala Val Ser Arg Val Ser Ser
 1               5                  10                  15

Asn Ile Gly Ala Ile Ala Ser Gly Gly Ala Ser Ala Leu Pro Gly Val
             20                  25                  30

Ile Ser Asn Ile Phe Ser Gly Val Ser Ala Ser Ala Gly Ser Tyr Glu
         35                  40                  45

Glu Ala Val Ile Gln Ser Leu Leu Glu Val Leu Ser Ala Leu Leu His
 50                  55                  60

Ile Leu Ser Asn Ser Ser Ile Gly Tyr Val Gly Ala Asp Gly Leu Thr
 65                  70                  75                  80

Asp Ser Leu Ala Val Val Gln Gln Ala Met Gly Pro Val Val Gly
                 85                  90                  95

<210> SEQ ID NO 71
<211> LENGTH: 101
<212> TYPE: PRT
<213> ORGANISM: Nephila antipodiana

<400> SEQUENCE: 71

Ser Thr Thr Ser Arg Leu Ser Thr Ala Glu Ala Ser Ser Arg Ile Ser
 1               5                  10                  15

Thr Ala Ala Ser Thr Leu Val Ser Gly Gly Tyr Leu Asn Thr Ala Ala
             20                  25                  30

Leu Pro Ser Val Ile Ala Asp Leu Phe Ala Gln Val Gly Ala Ser Ser
         35                  40                  45

Pro Gly Val Ser Asp Ser Glu Val Leu Ile Gln Val Leu Leu Glu Ile
 50                  55                  60

Val Ser Ser Leu Ile His Ile Leu Ser Ser Ser Val Gly Gln Val
 65                  70                  75                  80

Asp Phe Ser Ser Val Gly Ser Ser Ala Ala Ala Val Gly Gln Ser Met
                 85                  90                  95

Gln Val Val Met Gly
             100

<210> SEQ ID NO 72
<211> LENGTH: 100
<212> TYPE: PRT
<213> ORGANISM: Nephila clavipes
```

<400> SEQUENCE: 72

Ser Thr Thr Ser Arg Leu Ser Ser Ala Glu Ala Cys Ser Arg Ile Ser
1               5                   10                  15

Ala Ala Ala Ser Thr Leu Val Ser Gly Ser Leu Asn Thr Ala Ala Leu
            20                  25                  30

Pro Ser Val Ile Ser Asp Leu Phe Ala Gln Val Ser Ala Ser Ser Pro
        35                  40                  45

Gly Val Ser Gly Asn Glu Val Leu Ile Gln Val Leu Leu Glu Ile Val
    50                  55                  60

Ser Ser Leu Ile His Ile Leu Ser Ser Ser Val Gly Gln Val Asp
65                  70                  75                  80

Phe Ser Ser Val Gly Ser Ala Ala Val Gly Gln Ser Met Gln
                85                  90                  95

Val Val Met Gly
            100

<210> SEQ ID NO 73
<211> LENGTH: 103
<212> TYPE: PRT
<213> ORGANISM: Deinopis spinosa

<400> SEQUENCE: 73

Ala Ser Thr Ser Arg Leu Ala Ser Gly Gln Ala Thr Asp Arg Val Lys
1               5                   10                  15

Asp Val Val Ser Thr Leu Val Ser Asn Gly Ile Asn Gly Asp Ala Leu
            20                  25                  30

Ser Asn Ala Ile Ser Asn Val Met Thr Gln Val Asn Ala Ala Val Pro
        35                  40                  45

Gly Leu Ser Phe Cys Glu Arg Leu Ile Gln Val Leu Leu Glu Ile Val
    50                  55                  60

Ala Ala Leu Val His Ile Leu Ser Ser Ser Asn Val Gly Ser Ile Asp
65                  70                  75                  80

Tyr Gly Ser Thr Ser Arg Thr Ala Ile Gly Val Ser Asn Ala Leu Ala
                85                  90                  95

Ser Ala Val Ala Gly Ala Phe
            100

<210> SEQ ID NO 74
<211> LENGTH: 352
<212> TYPE: PRT
<213> ORGANISM: Artificial
<220> FEATURE:
<223> OTHER INFORMATION: Artificial construct

<400> SEQUENCE: 74

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Ala Ala Gly Gln
                165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Ala Ala Gly Ser Gly
            195                 200                 205

Gln Gly Gly Tyr Gly Gly Gln Gly Gln Gly Gly Tyr Gly Gln Ser Gly
            210                 215                 220

Ser Val Thr Ser Gly Gly Tyr Gly Tyr Gly Thr Ser Ala Ala Ala Gly
225                 230                 235                 240

Ala Gly Val Ala Ala Gly Ser Tyr Ala Ala Ser Thr Ser Arg Leu Ala
            245                 250                 255

Ser Gly Gln Ala Thr Asp Arg Val Lys Asp Val Val Ser Thr Leu Val
            260                 265                 270

Ser Asn Gly Ile Asn Gly Asp Ala Leu Ser Asn Ala Ile Ser Asn Val
            275                 280                 285

Met Thr Gln Val Asn Ala Ala Val Pro Gly Leu Ser Phe Cys Glu Arg
290                 295                 300

Leu Ile Gln Val Leu Leu Glu Ile Val Ala Ala Leu Val His Ile Leu
305                 310                 315                 320

Ser Ser Ser Asn Val Gly Ser Ile Asp Tyr Gly Ser Thr Ser Arg Thr
            325                 330                 335

Ala Ile Gly Val Ser Asn Ala Leu Ala Ser Ala Val Ala Gly Ala Phe
            340                 345                 350

<210> SEQ ID NO 75
<211> LENGTH: 350
<212> TYPE: PRT
<213> ORGANISM: Artificial
<220> FEATURE:
<223> OTHER INFORMATION: Artificial construct

<400> SEQUENCE: 75

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
            85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Ala Ala Gly Gln
                165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Ala Ala Gly Ser Gly
            195                 200                 205

Gln Gly Gly Tyr Gly Gly Gln Gly Gln Gly Gly Tyr Gly Gln Ser Gly
            210                 215                 220

Ser Val Thr Ser Gly Gly Tyr Gly Tyr Gly Thr Ser Ala Ala Ala Gly
225                 230                 235                 240

Ala Gly Val Ala Ala Gly Ser Tyr Ala Asn Ser Val Ser Arg Leu Ser
                245                 250                 255

Ser Pro Ser Ala Val Ser Arg Val Ser Ser Ala Val Ser Ser Leu Val
            260                 265                 270

Ser Asn Gly Gln Val Asn Met Ala Ala Leu Pro Asn Ile Ile Ser Asn
            275                 280                 285

Ile Ser Ser Ser Val Ser Ala Ser Ala Pro Gly Ala Ser Gly Cys Glu
            290                 295                 300

Val Ile Val Gln Ala Leu Leu Glu Val Ile Thr Ala Leu Val Gln Ile
305                 310                 315                 320

Val Ser Ser Ser Val Gly Tyr Ile Asn Pro Ser Ala Val Asn Gln
                325                 330                 335

Ile Thr Asn Val Val Ala Asn Ala Met Ala Gln Val Met Gly
            340                 345                 350

<210> SEQ ID NO 76
<211> LENGTH: 343
<212> TYPE: PRT
<213> ORGANISM: Artificial
<220> FEATURE:
<223> OTHER INFORMATION: Artificial construct

<400> SEQUENCE: 76

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Ala Ala Gly Gln
                165                 170                 175

Gly Gly Gln Gly Gly Tyr Gly Arg Gln Ser Gln Gly Ala Gly Ser Ala
                180                 185                 190

Ala Ala Ala Ala Ala Ala Ala Ala Ala Ala Ala Ala Ala Gly Ser Gly
                195                 200                 205

Gln Gly Gly Tyr Gly Gly Gln Gly Gln Gly Gly Tyr Gly Gln Ser Gly
210                 215                 220

Ser Val Thr Ser Gly Gly Tyr Gly Tyr Gly Thr Ser Ala Ala Ala Gly
225                 230                 235                 240

Ala Gly Val Ala Ala Gly Ser Tyr Ala Ser Val Tyr Leu Arg Leu Gln
                245                 250                 255

Pro Arg Leu Glu Val Ser Ser Ala Val Ser Ser Leu Val Ser Ser Gly
                260                 265                 270

Pro Thr Asn Gly Ala Ala Val Ser Gly Ala Leu Asn Ser Leu Val Ser
                275                 280                 285

Gln Ile Ser Ala Ser Asn Pro Gly Leu Ser Gly Cys Asp Ala Leu Val
290                 295                 300

Gln Ala Leu Leu Glu Leu Val Ser Ala Leu Val Ala Ile Leu Ser Ser
305                 310                 315                 320

Ala Ser Ile Gly Gln Val Asn Val Ser Ser Val Ser Gln Ser Thr Gln
                325                 330                 335

Met Ile Ser Gln Ala Leu Ser
                340

<210> SEQ ID NO 77
<211> LENGTH: 350
<212> TYPE: PRT
<213> ORGANISM: Artificial
<220> FEATURE:
<223> OTHER INFORMATION: Artificial construct

<400> SEQUENCE: 77

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
                35                  40                  45

Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Gly Gln
            165                 170                 175

Gly Gly Gln Gly Gly Tyr Gly Arg Gln Ser Gln Gly Ala Gly Ser Ala
                180                 185                 190

Ala Ala Ala Ala Ala Ala Ala Ala Ala Ala Ala Gly Ser Gly
            195                 200                 205

Gln Gly Gly Tyr Gly Gly Gln Gly Gly Tyr Gly Gln Ser Gly
    210                 215                 220

Ser Val Thr Ser Gly Gly Tyr Gly Tyr Gly Thr Ser Ala Ala Ala Gly
225                 230                 235                 240

Ala Gly Val Ala Ala Gly Ser Tyr Ala Ser Ala Ala Ser Arg Leu Ser
                245                 250                 255

Ser Pro Ser Ser Ser Arg Ile Ser Ser Ala Ala Ser Ser Leu Ala
                260                 265                 270

Thr Gly Gly Val Leu Asn Ser Ala Ala Leu Pro Ser Val Val Ser Asn
                275                 280                 285

Met Met Ser Gln Val Ser Ala Ser Ser Pro Gly Met Ser Ser Ser Glu
    290                 295                 300

Val Val Ile Gln Ala Leu Leu Glu Leu Val Ser Ser Leu Ile His Ile
305                 310                 315                 320

Leu Ser Ser Ala Asn Ile Gly Gln Val Asp Phe Asn Ser Val Gly Asn
                325                 330                 335

Thr Ala Ala Val Val Gly Gln Ser Leu Gly Ala Ala Leu Gly
                340                 345                 350

<210> SEQ ID NO 78
<211> LENGTH: 346
<212> TYPE: PRT
<213> ORGANISM: Artificial
<220> FEATURE:
<223> OTHER INFORMATION: Artificial construct

<400> SEQUENCE: 78

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
    115                 120                 125

Val Ser Met Phe Ala Gln Ala Gly Met Asn Asp Val Ser Ala Gly Asn
130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Gly Gln
            165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Gly Ser Gly
            195                 200                 205

Gln Gly Gly Tyr Gly Gly Gln Gly Gln Gly Gly Tyr Gly Gln Ser Gly
            210                 215                 220

Asn Ser Val Thr Ser Gly Tyr Gly Tyr Gly Thr Ser Ala Ala Ala
225                 230                 235                 240

Gly Ala Gly Val Ala Ala Gly Ser Tyr Ala Gly Ala Val Asn Arg Leu
            245                 250                 255

Ser Ser Ala Glu Ala Ala Ser Ala Val Ser Ser Asn Ile Ala Ala Ile
            260                 265                 270

Ala Ser Gly Gly Ala Ser Ala Leu Pro Ser Val Ile Ser Asn Ile Tyr
            275                 280                 285

Ser Gly Val Val Ala Ser Gly Val Ser Ser Asn Glu Ala Leu Ile Gln
            290                 295                 300

Ala Leu Leu Glu Leu Leu Ser Ala Leu Val His Val Leu Ser Ser Ala
305                 310                 315                 320

Ser Ile Gly Asn Val Ser Ser Val Gly Val Asp Ser Thr Leu Asn Val
            325                 330                 335

Val Gln Asp Ser Val Gly Gln Tyr Val Gly
            340                 345

<210> SEQ ID NO 79
<211> LENGTH: 346
<212> TYPE: PRT
<213> ORGANISM: Artificial
<220> FEATURE:
<223> OTHER INFORMATION: Artificial construct

<400> SEQUENCE: 79

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
            50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Ser Leu Ser
            85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
            130                 135                 140

Ser Gly Arg Gly Gln Gly Gly Tyr Gly Gln Gly Ser Gly Gly Asn Ala
145                 150                 155                 160

Ala Ala Ala Ala Ala Ala Ala Ala Ala Ala Ala Ala Gly Gln
            165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Ala Ala Gly Ser Gly
            195                 200                 205

Gln Gly Gly Tyr Gly Gly Gln Gly Gln Gly Gly Tyr Gly Gln Ser Gly
            210                 215                 220

Asn Ser Val Thr Ser Gly Gly Tyr Gly Tyr Gly Thr Ser Ala Ala Ala
225                 230                 235                 240

Gly Ala Gly Val Ala Ala Gly Ser Tyr Ala Gly Ala Val Asn Arg Leu
            245                 250                 255

Ser Ser Ala Glu Ala Ala Ser Arg Val Ser Ser Asn Ile Ala Ala Ile
            260                 265                 270

Ala Ser Gly Gly Ala Ser Ala Leu Pro Ser Val Ile Ser Asn Ile Tyr
            275                 280                 285

Ser Gly Val Val Ala Ser Gly Val Ser Ser Asn Glu Ala Leu Ile Gln
            290                 295                 300

Ala Leu Leu Glu Leu Leu Ser Ala Leu Val His Val Leu Ser Ser Ala
305                 310                 315                 320

Ser Ile Gly Asn Val Ser Ser Val Gly Val Ala Ser Thr Leu Asn Val
            325                 330                 335

Val Gln Asp Ser Val Gly Gln Tyr Val Gly
            340                 345

<210> SEQ ID NO 80
<211> LENGTH: 131
<212> TYPE: PRT
<213> ORGANISM: Euprosthenops australis

<400> SEQUENCE: 80

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Asp Met Ser Thr Ile Ala Gln Ser Met Val Gln Ser Ile
            35                  40                  45

Gln Ser Leu Ala Ala Gln Gly Arg Thr Ser Pro Asn Lys Leu Gln Ala
        50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
            85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
            115                 120                 125

Asn Asp Val
        130

<210> SEQ ID NO 81
<211> LENGTH: 127
<212> TYPE: PRT
<213> ORGANISM: Latrodectus geometricus

<400> SEQUENCE: 81

Gln Ala Asn Thr Pro Trp Ser Ser Lys Gln Asn Ala Asp Ala Phe Ile
1               5                   10                  15

Ser Ala Phe Met Thr Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45

Asp Asn Met Gly Gly Arg Ile Thr Pro Ser Lys Leu Gln Ala Leu Asp
50                  55                  60

Met Ala Phe Ala Ser Ser Val Ala Glu Ile Ala Ala Val Glu Gly Gln
65                  70                  75                  80

Asn Ile Gly Val Thr Thr Asn Ala Ile Ser Asp Ala Leu Thr Ser Ala
                85                  90                  95

Phe Tyr Gln Thr Thr Gly Val Val Asn Asn Lys Phe Ile Ser Glu Ile
            100                 105                 110

Arg Ser Leu Ile Asn Met Phe Ala Gln Ala Ser Ala Asn Asp Val
            115                 120                 125

<210> SEQ ID NO 82
<211> LENGTH: 127
<212> TYPE: PRT
<213> ORGANISM: Latrodectus hesperus

<400> SEQUENCE: 82

Gln Ala Asn Thr Pro Trp Ser Ser Lys Ala Asn Ala Asp Ala Phe Ile
1               5                   10                  15

Asn Ser Phe Ile Ser Ala Ala Ser Asn Thr Gly Ser Phe Ser Gln Asp
            20                  25                  30

Gln Met Glu Asp Met Ser Leu Ile Gly Asn Thr Leu Met Ala Ala Met
        35                  40                  45

Asp Asn Met Gly Gly Arg Ile Thr Pro Ser Lys Leu Gln Ala Leu Asp
50                  55                  60

Met Ala Phe Ala Ser Ser Val Ala Glu Ile Ala Ala Ser Glu Gly Gly
65                  70                  75                  80

Asp Leu Gly Val Thr Thr Asn Ala Ile Ala Asp Ala Leu Thr Ser Ala
                85                  90                  95

Phe Tyr Gln Thr Thr Gly Val Val Asn Ser Arg Phe Ile Ser Glu Ile
            100                 105                 110

Arg Ser Leu Ile Gly Met Phe Ala Gln Ala Ser Ala Asn Asp Val
            115                 120                 125

<210> SEQ ID NO 83
<211> LENGTH: 130
<212> TYPE: PRT
<213> ORGANISM: Nephila clavipes

<400> SEQUENCE: 83

Gln Asn Thr Pro Trp Ser Ser Thr Glu Leu Ala Asp Ala Phe Ile Asn
1               5                   10                  15

Ala Phe Met Asn Glu Ala Gly Arg Thr Gly Ala Phe Thr Ala Asp Gln
            20                  25                  30

Leu Asp Asp Met Ser Thr Ile Gly Asp Thr Ile Lys Thr Ala Met Asp
        35                  40                  45

Lys Met Ala Arg Ser Asn Lys Ser Ser Lys Gly Lys Leu Gln Ala Leu
50                  55                  60

Asn Met Ala Phe Ala Ser Met Ala Glu Ile Ala Val Glu Gln
65                  70                  75                  80

Gly Gly Leu Ser Val Asp Ala Lys Thr Asn Ala Ile Ala Asp Ser Leu
            85                  90                  95

Asn Ser Ala Phe Tyr Gln Thr Thr Gly Ala Ala Asn Pro Gln Phe Val
                100                 105                 110

Asn Glu Ile Arg Ser Leu Ile Asn Met Phe Ala Gln Ser Ser Ala Asn
            115                 120                 125

Glu Val
    130

<210> SEQ ID NO 84
<211> LENGTH: 131
<212> TYPE: PRT
<213> ORGANISM: Argiope trifasciata

<400> SEQUENCE: 84

Gln Gly Ala Thr Pro Trp Glu Asn Ser Gln Leu Ala Glu Ser Phe Ile
1               5                   10                  15

Ser Arg Phe Leu Arg Phe Ile Gly Gln Ser Gly Ala Phe Ser Pro Asn
            20                  25                  30

Gln Leu Asp Asp Met Ser Ser Ile Gly Asp Thr Leu Lys Thr Ala Ile
            35                  40                  45

Glu Lys Met Ala Gln Ser Arg Lys Ser Ser Lys Ser Lys Leu Gln Ala
50                  55                  60

Leu Asn Met Ala Phe Ala Ser Ser Met Ala Glu Ile Ala Val Ala Glu
65                  70                  75                  80

Gln Gly Gly Leu Ser Leu Glu Ala Lys Thr Asn Ala Ile Ala Ser Ala
            85                  90                  95

Leu Ser Ala Ala Phe Leu Glu Thr Thr Gly Tyr Val Asn Gln Gln Phe
                100                 105                 110

Val Asn Glu Ile Lys Thr Leu Ile Phe Met Ile Ala Gln Ala Ser Ser
            115                 120                 125

Asn Glu Ile
    130

<210> SEQ ID NO 85
<211> LENGTH: 124
<212> TYPE: PRT
<213> ORGANISM: Latrodectus geometricus

<400> SEQUENCE: 85

Leu Arg Trp Ser Ser Lys Asp Asn Ala Asp Arg Phe Ile Asn Ala Phe
1               5                   10                  15

Leu Gln Ala Ala Ser Asn Ser Gly Ala Phe Ser Ser Asp Gln Val Asp
            20                  25                  30

Asp Met Ser Val Ile Gly Asn Thr Leu Met Thr Ala Met Asp Asn Met
            35                  40                  45

Gly Gly Arg Ile Thr Pro Ser Lys Leu Gln Ala Leu Asp Met Ala Phe
50                  55                  60

Ala Ser Ser Val Ala Glu Ile Ala Val Ala Asp Gly Gln Asn Val Gly
65                  70                  75                  80

Gly Ala Thr Asn Ala Ile Ser Asn Ala Leu Arg Ser Ala Phe Tyr Gln
            85                  90                  95

-continued

Thr Thr Gly Val Val Asn Asn Gln Phe Ile Ser Glu Ile Ser Asn Leu
            100                 105                 110

Ile Asn Met Phe Ala Gln Val Ser Ala Asn Glu Val
        115                 120

<210> SEQ ID NO 86
<211> LENGTH: 127
<212> TYPE: PRT
<213> ORGANISM: Latrodectus hesperus

<400> SEQUENCE: 86

Gln Ala Asn Thr Pro Trp Ser Ser Lys Glu Asn Ala Asp Ala Phe Ile
1               5                   10                  15

Gly Ala Phe Met Asn Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45

Asp Asn Met Gly Gly Arg Ile Thr Gln Ser Lys Leu Gln Ala Leu Asp
    50                  55                  60

Met Ala Phe Ala Ser Ser Val Ala Glu Ile Ala Val Ala Asp Gly Gln
65                  70                  75                  80

Asn Val Gly Ala Ala Thr Asn Ala Ile Ser Asp Ala Leu Arg Ser Ala
                85                  90                  95

Phe Tyr Gln Thr Thr Gly Val Val Asn Asn Gln Phe Ile Thr Gly Ile
            100                 105                 110

Ser Ser Leu Ile Gly Met Phe Ala Gln Val Ser Gly Asn Glu Val
        115                 120                 125

<210> SEQ ID NO 87
<211> LENGTH: 131
<212> TYPE: PRT
<213> ORGANISM: Nephila inaurata madagascariensis

<400> SEQUENCE: 87

Gln Ala Asn Thr Pro Trp Ser Asp Thr Ala Thr Ala Asp Ala Phe Ile
1               5                   10                  15

Gln Asn Phe Leu Gly Ala Val Ser Gly Ser Gly Ala Phe Thr Pro Asp
            20                  25                  30

Gln Leu Asp Asp Met Ser Thr Val Gly Asp Thr Ile Met Ser Ala Met
        35                  40                  45

Asp Lys Met Ala Arg Ser Asn Lys Ser Ser Lys Ser Lys Leu Gln Ala
    50                  55                  60

Leu Asn Met Ala Phe Ala Ser Ser Met Ala Glu Ile Ala Ala Val Glu
65                  70                  75                  80

Gln Gly Gly Gln Ser Met Asp Val Lys Thr Asn Ala Ile Ala Asn Ala
                85                  90                  95

Leu Asp Ser Ala Phe Tyr Met Thr Thr Gly Ser Thr Asn Gln Gln Phe
            100                 105                 110

Val Asn Glu Met Arg Ser Leu Ile Asn Met Leu Ser Ala Ala Ala Val
        115                 120                 125

Asn Glu Val
    130

<210> SEQ ID NO 88
<211> LENGTH: 131
<212> TYPE: PRT
<213> ORGANISM: Nephila clavipes -continued

```
<400> SEQUENCE: 88

Gln Ala Arg Ser Pro Trp Ser Asp Thr Ala Thr Ala Asp Ala Phe Ile
1               5                   10                  15

Gln Asn Phe Leu Ala Ala Val Ser Gly Ser Gly Ala Phe Thr Ser Asp
                20                  25                  30

Gln Leu Asp Asp Met Ser Thr Ile Gly Asp Thr Ile Met Ser Ala Met
            35                  40                  45

Asp Lys Met Ala Arg Ser Asn Lys Ser Ser Gln His Lys Leu Gln Ala
        50                  55                  60

Leu Asn Met Ala Phe Ala Ser Ser Met Ala Glu Ile Ala Ala Val Glu
65                  70                  75                  80

Gln Gly Gly Met Ser Met Ala Val Lys Thr Asn Ala Ile Val Asp Gly
                85                  90                  95

Leu Asn Ser Ala Phe Tyr Met Thr Thr Gly Ala Ala Asn Pro Gln Phe
                100                 105                 110

Val Asn Glu Met Arg Ser Leu Ile Ser Met Ile Ser Ala Ala Ser Ala
            115                 120                 125

Asn Glu Val
    130

<210> SEQ ID NO 89
<211> LENGTH: 129
<212> TYPE: PRT
<213> ORGANISM: Argiope bruennichi

<400> SEQUENCE: 89

Ala Val Pro Ser Val Phe Ser Ser Pro Asn Leu Ala Ser Gly Phe Leu
1               5                   10                  15

Gln Cys Leu Thr Phe Gly Ile Gly Asn Ser Pro Ala Phe Pro Thr Gln
                20                  25                  30

Glu Gln Gln Asp Leu Asp Ala Ile Ala Gln Val Ile Leu Asn Ala Val
            35                  40                  45

Ser Ser Asn Thr Gly Ala Thr Ala Ser Ala Arg Ala Gln Ala Leu Ser
        50                  55                  60

Thr Ala Leu Ala Ser Ser Leu Thr Asp Leu Leu Ile Ala Glu Ser Ala
65                  70                  75                  80

Glu Ser Asn Tyr Ser Asn Gln Leu Ser Glu Leu Thr Gly Ile Leu Ser
                85                  90                  95

Asp Cys Phe Ile Gln Thr Thr Gly Ser Asp Asn Pro Ala Phe Val Ser
                100                 105                 110

Arg Ile Gln Ser Leu Ile Ser Val Leu Ser Gln Asn Ala Asp Thr Asn
            115                 120                 125

Ile

<210> SEQ ID NO 90
<211> LENGTH: 129
<212> TYPE: PRT
<213> ORGANISM: Nephila clavata

<400> SEQUENCE: 90

Pro Val Pro Ser Val Phe Ser Ser Pro Ser Leu Ala Ser Gly Phe Leu
1               5                   10                  15

Gly Cys Leu Thr Thr Gly Ile Gly Leu Ser Pro Ala Phe Pro Phe Gln
                20                  25                  30

Glu Gln Gln Asp Leu Asp Asp Leu Ala Lys Val Ile Leu Ser Ala Val
            35                  40                  45
```

```
Thr Ser Asn Thr Asp Thr Ser Lys Ser Ala Arg Ala Gln Ala Leu Ser
 50                  55                  60

Thr Ala Leu Ala Ser Ser Leu Ala Asp Leu Leu Ile Ser Glu Ser Ser
 65                  70                  75                  80

Gly Ser Ser Tyr Gln Thr Gln Ile Ser Ala Leu Thr Asn Ile Leu Ser
                 85                  90                  95

Asp Cys Phe Val Thr Thr Thr Gly Ser Asn Asn Pro Ala Phe Val Ser
                100                 105                 110

Arg Val Gln Thr Leu Ile Gly Val Leu Ser Gln Ser Ser Ser Asn Ala
                115                 120                 125

Ile
```

<210> SEQ ID NO 91
<211> LENGTH: 128
<212> TYPE: PRT
<213> ORGANISM: Latrodectus hesperus

<400> SEQUENCE: 91

```
Ala Ser Val Asn Ile Phe Asn Ser Pro Asn Ala Ala Thr Ser Phe Leu
  1               5                  10                  15

Asn Cys Leu Arg Ser Asn Ile Glu Ser Ser Pro Ala Phe Pro Phe Gln
                 20                  25                  30

Glu Gln Ala Asp Leu Asp Ser Ile Ala Glu Val Ile Leu Ser Asp Val
                 35                  40                  45

Ser Ser Val Asn Thr Ala Ser Ser Ala Thr Ser Leu Ala Leu Ser Thr
 50                  55                  60

Ala Leu Ala Ser Ser Leu Ala Glu Leu Leu Val Thr Glu Ser Ala Glu
 65                  70                  75                  80

Glu Asp Ile Asp Asn Gln Val Val Ala Leu Ser Thr Ile Leu Ser Gln
                 85                  90                  95

Cys Phe Val Glu Thr Thr Gly Ser Pro Asn Pro Ala Phe Val Ala Ser
                100                 105                 110

Val Lys Ser Leu Leu Gly Val Leu Ser Gln Ser Ala Ser Asn Tyr Glu
                115                 120                 125
```

<210> SEQ ID NO 92
<211> LENGTH: 130
<212> TYPE: PRT
<213> ORGANISM: Nephila clavipes

<400> SEQUENCE: 92

```
Ile Ala Asn Ser Pro Phe Ser Asn Pro Asn Thr Ala Glu Ala Phe Ala
  1               5                  10                  15

Arg Ser Phe Val Ser Asn Ile Val Ser Ser Gly Glu Phe Gly Ala Gln
                 20                  25                  30

Gly Ala Glu Asp Phe Asp Asp Ile Ile Gln Ser Leu Ile Gln Ala Gln
                 35                  40                  45

Ser Met Gly Lys Gly Arg His Asp Thr Lys Ala Lys Ala Lys Ala Met
 50                  55                  60

Gln Val Ala Leu Ala Ser Ser Ile Ala Glu Leu Val Ile Ala Glu Ser
 65                  70                  75                  80

Ser Gly Gly Asp Val Gln Arg Lys Thr Asn Val Ile Ser Asn Ala Leu
                 85                  90                  95

Arg Asn Ala Leu Met Ser Thr Thr Gly Ser Pro Asn Glu Glu Phe Val
                100                 105                 110
```

His Glu Val Gln Asp Leu Ile Gln Met Leu Ser Gln Glu Gln Ile Asn
         115                 120                 125

Glu Val
    130

<210> SEQ ID NO 93
<211> LENGTH: 130
<212> TYPE: PRT
<213> ORGANISM: Nephila inaurata madagascariensis

<400> SEQUENCE: 93

Ile Val Asn Ser Pro Phe Ser Asn Pro Asn Thr Ala Glu Ala Phe Ala
1               5                   10                  15

Arg Ser Phe Val Ser Asn Val Val Ser Ser Gly Glu Phe Gly Ala Gln
            20                  25                  30

Gly Ala Glu Asp Phe Asp Asp Ile Ile Gln Ser Leu Ile Gln Ala Gln
        35                  40                  45

Ser Met Gly Lys Gly Arg His Asp Thr Lys Ala Lys Ala Lys Ala Met
50                  55                  60

Gln Val Ala Leu Ala Ser Ser Ile Ala Glu Leu Val Ile Ala Glu Ser
65                  70                  75                  80

Ser Gly Gly Asp Val Gln Arg Lys Thr Asn Val Ile Ser Asn Ala Leu
                85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Glu Gln Ile Asn
         115                 120                 125

Glu Val
    130

<210> SEQ ID NO 94
<211> LENGTH: 9
<212> TYPE: PRT
<213> ORGANISM: Artificial Sequence
<220> FEATURE:
<223> OTHER INFORMATION: His tag

<400> SEQUENCE: 94

Met Gly His His His His His His Met
1               5

<210> SEQ ID NO 95
<211> LENGTH: 133
<212> TYPE: PRT
<213> ORGANISM: Euprosthenops australis

<400> SEQUENCE: 95

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Asp Met Ser Thr Ile Ala Gln Ser Met Val Gln Ser Ile
        35                  40                  45

Gln Ser Leu Ala Ala Gln Gly Arg Thr Ser Pro Asn Lys Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

```
<210> SEQ ID NO 96
<211> LENGTH: 84
<212> TYPE: PRT
<213> ORGANISM: Euprosthenops australis

<400> SEQUENCE: 96

Gly Asn Ser Gly Arg Gly Gln Gly Gly Tyr Gly Gln Gly Ser Gly Gly
1               5                   10                  15

Asn Ala Ala Ala Ala Ala Ala Ala Ala Ala Ala Ala Ala Ala Ala Ala
            20                  25                  30

Gly Gln Gly Gly Gln Gly Gly Tyr Gly Arg Gln Ser Gln Gly Ala Gly
        35                  40                  45

Ser Ala Ala Ala Ala Ala Ala Ala Ala Ala Ala Ala Ala Ala Ala Gly
    50                  55                  60

Ser Gly Gln Gly Gly Tyr Gly Gly Gln Gly Gln Gly Gly Tyr Gly Gln
65                  70                  75                  80

Ser Gly Asn Ser

<210> SEQ ID NO 97
<211> LENGTH: 120
<212> TYPE: PRT
<213> ORGANISM: Artificial Sequence
<220> FEATURE:
<223> OTHER INFORMATION: CT based on Araneus ventricosus

<400> SEQUENCE: 97

Val Thr Ser Gly Gly Tyr Gly Tyr Gly Thr Ser Ala Ala Ala Gly Ala
1               5                   10                  15

Gly Val Ala Ala Gly Ser Tyr Ala Gly Ala Val Asn Arg Leu Ser Ser
            20                  25                  30

Ala Glu Ala Ala Ser Arg Val Ser Ser Asn Ile Ala Ala Ile Ala Ser
        35                  40                  45

Gly Gly Ala Ser Ala Leu Pro Ser Val Ile Ser Asn Ile Tyr Ser Gly
    50                  55                  60

Val Val Ala Ser Gly Val Ser Ser Asn Glu Ala Leu Ile Gln Ala Leu
65                  70                  75                  80

Leu Glu Leu Leu Ser Ala Leu Val His Val Leu Ser Ser Ala Ser Ile
            85                  90                  95

Gly Asn Val Ser Ser Val Gly Val Asp Ser Thr Leu Asn Val Val Gln
            100                 105                 110

Asp Ser Val Gly Gln Tyr Val Gly
            115                 120
```